(12) United States Patent
Scharschmidt et al.

(10) Patent No.: US 10,668,040 B2
(45) Date of Patent: *Jun. 2, 2020

(54) TREATMENT OF UREA CYCLE DISORDERS IN NEONATES AND INFANTS

(71) Applicant: Horizon Therapeutics, LLC, Lake Forest, IL (US)

(72) Inventors: Bruce Scharschmidt, San Francisco, CA (US); Masoud Mokhtarani, Walnut Creek, CA (US)

(73) Assignee: Horizon Therapeutics, LLC, Lake Forest, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/128,140

(22) Filed: Sep. 11, 2018

(65) Prior Publication Data

US 2019/0076386 A1    Mar. 14, 2019

Related U.S. Application Data

(60) Provisional application No. 62/628,252, filed on Feb. 8, 2018, provisional application No. 62/556,698, filed on Sep. 11, 2017.

(51) Int. Cl.
*A61K 31/216* (2006.01)
*A61K 9/00* (2006.01)
*G01N 33/84* (2006.01)

(52) U.S. Cl.
CPC .......... *A61K 31/216* (2013.01); *A61K 9/0053* (2013.01); *A61K 9/0095* (2013.01); *G01N 33/84* (2013.01); *G01N 2800/52* (2013.01); *G01N 2800/708* (2013.01)

(58) Field of Classification Search
CPC ........................... A61K 31/192; A61K 31/216
See application file for complete search history.

(56) References Cited

U.S. PATENT DOCUMENTS

| | | | |
|---|---|---|---|
| 3,686,238 A | 8/1972 | Alejandro Zaffaroni | |
| 4,284,647 A | 8/1981 | Brusilow | |
| 4,457,942 A | 7/1984 | Brusilow | |
| 5,654,333 A | 8/1997 | Samid | |
| 5,968,979 A | 10/1999 | Brusilow | |
| 6,060,510 A | 5/2000 | Brusilow | |
| 6,083,984 A | 7/2000 | Brusilow | |
| 6,219,567 B1 | 4/2001 | Eggers | |
| 6,825,384 B1 | 11/2004 | Prakash | |
| 8,094,521 B2 | 1/2012 | Levy | |
| 8,404,215 B1 | 3/2013 | Scharschmidt | |
| 8,642,012 B2 | 2/2014 | Scharschmidt | |
| 9,078,865 B2 | 7/2015 | Lee | |
| 9,095,559 B2 | 8/2015 | Scharschmidt | |
| 9,254,278 B2 | 2/2016 | Scharschmidt | |
| 9,289,406 B2 | 3/2016 | Scharschmidt | |
| 9,326,966 B2 | 5/2016 | Scharschmidt | |
| 9,561,197 B2* | 2/2017 | Scharschmidt | A61K 31/192 |
| 9,914,692 B2 | 3/2018 | Chang | |
| 9,962,358 B2 | 5/2018 | Scharschmidt | |
| 9,962,359 B2 | 5/2018 | Scharschmidt | |
| 9,999,608 B2 | 6/2018 | Scharschmidt | |
| 1,004,595 A1 | 8/2018 | Scharschmidt | |
| 10,045,959 B1 | 8/2018 | Scharschmidt | |
| 10,183,002 B2 | 1/2019 | Scharschmidt | |
| 10,183,003 B2 | 1/2019 | Scharschmidt | |
| 10,183,004 B2 | 1/2019 | Scharschmidt | |
| 10,183,005 B2 | 1/2019 | Scharschmidt | |
| 10,183,006 B2 | 1/2019 | Scharschmidt | |
| 10,329,236 B2 | 6/2019 | Chang | |
| 2003/0195255 A1 | 10/2003 | Summar | |
| 2004/0229948 A1 | 11/2004 | Summar | |
| 2005/0273359 A1 | 12/2005 | Young | |
| 2006/0135612 A1 | 6/2006 | Ferrante | |
| 2008/0119554 A1 | 5/2008 | Jalan | |
| 2010/0008859 A1 | 1/2010 | Scharschmidt | |
| 2010/0016207 A1 | 1/2010 | Wurtman | |
| 2012/0022157 A1 | 1/2012 | Scharschmidt | |
| 2012/0220661 A1 | 8/2012 | Lee | |
| 2013/0085179 A1 | 4/2013 | Scharschmidt | |
| 2013/0172543 A1 | 7/2013 | Iwabuchi | |
| 2013/0210914 A1 | 8/2013 | Scharschmidt | |
| 2013/0281530 A1* | 10/2013 | Scharschmidt ...... | A61K 31/192 514/533 |
| 2014/0142186 A1 | 5/2014 | Scharschmidt | |
| 2014/0256807 A1 | 9/2014 | Scharschmidt | |
| 2015/0094278 A1 | 4/2015 | Scharschmidt | |
| 2015/0105469 A1 | 4/2015 | Scharschmidt | |
| 2015/0335605 A1 | 11/2015 | Scharschmidt | |

(Continued)

FOREIGN PATENT DOCUMENTS

| CN | 1778963 | 5/2006 |
|---|---|---|
| CN | 103304402 A | 9/2013 |

(Continued)

OTHER PUBLICATIONS

Berry et al., Mol Genet Metab, 2014, 112(1): 17-24.*
Smith et al., J Pediatr, 2013, 162(6): 1228-34.*
"Program for SIMD annual meeting", Molecular Genetics and Metabolism, (Mar. 1, 2012), vol. 105, No. 3, doi:10.1016/j.ymgme.2012.01.004, ISSN 1096-7192, pp. 273-366, XP055202401.
Ahrens, M. et al. (Jan. 2001). 'Consensus Statement From a Conference for the Management of Patients With Urea Cycle Disorders.' Supp. Journal of Pediatrics 138(1 ):S1-55.
Alfentanil Highlights of Prescribing informmation Dec. 2016 (Year: 2016).
Amara et al., Biochim. Biophys. Acta 1791: 983-990, 2009.
Ambrose, A.M. et al. (1933). 'Further Studies on the Detoxification of Phenylacetic Acid,' J. Bio. Chem. 101:669-675.

(Continued)

*Primary Examiner* — Rei Tsang Shiao
(74) *Attorney, Agent, or Firm* — Chris Marion

(57) ABSTRACT

Nitrogen scavenging drugs such as glycerol phenylbutyrate can be administered safely to infants and toddlers with urea cycle disorders by adjusting the dosage based on one or more biomarkers selected from the group consisting of urinary-PAGN and plasma PAA:PAGN ratio.

12 Claims, 7 Drawing Sheets

(56) References Cited

U.S. PATENT DOCUMENTS

| | | |
|---|---|---|
| 2016/0074356 A1 | 3/2016 | Scharschmidt |
| 2016/0081969 A1 | 3/2016 | Scharschmidt |
| 2016/0199332 A1 | 7/2016 | Scharschmidt |
| 2016/0199333 A1 | 7/2016 | Scharschmidt |
| 2016/0199334 A1 | 7/2016 | Scharschmidt |
| 2016/0202240 A1 | 7/2016 | Scharschmidt |
| 2016/0223520 A1 | 8/2016 | Scharschmidt |
| 2016/0354025 A1 | 12/2016 | Scharschmidt |
| 2017/0266143 A1 | 9/2017 | Scharschmidt |
| 2017/0348269 A1 | 12/2017 | Scharschmidt |
| 2017/0354631 A1 | 12/2017 | Scharschmidt |
| 2017/0354632 A1 | 12/2017 | Scharschmidt |
| 2017/0362160 A1 | 12/2017 | Chang |
| 2018/0015058 A1 | 1/2018 | Scharschmidt |
| 2018/0015064 A1 | 1/2018 | Scharschmidt |
| 2018/0015065 A1 | 1/2018 | Scharschmidt |
| 2018/0017546 A1 | 1/2018 | Scharschmidt |
| 2018/0021291 A1 | 1/2018 | Scharschmidt |
| 2018/0021292 A1 | 1/2018 | Scharschmidt |
| 2018/0021293 A1 | 1/2018 | Scharschmidt |
| 2018/0055807 A1 | 3/2018 | Scharschmidt |
| 2018/0221326 A1 | 8/2018 | Scharschmidt |
| 2018/0221327 A1 | 8/2018 | Scharschmidt |
| 2018/0235920 A1 | 8/2018 | Scharschmidt |
| 2018/0263938 A1 | 9/2018 | Scharschmidt |
| 2018/0263949 A1 | 9/2018 | Scharschmidt |
| 2019/0076383 A1 | 3/2019 | Scharschmidt |
| 2019/0076384 A1 | 3/2019 | Scharschmidt |
| 2019/0125713 A1 | 5/2019 | Scharschmidt |

FOREIGN PATENT DOCUMENTS

| | | |
|---|---|---|
| EP | 2607366 A1 | 6/2013 |
| IT | 1317073 B1 | 5/2003 |
| JP | 2012501329 | 1/2012 |
| WO | 199422494 | 10/1994 |
| WO | 1996024571 | 8/1996 |
| WO | 2005053607 A2 | 6/2005 |
| WO | 2005053607 A3 | 6/2005 |
| WO | 2006056794 A1 | 6/2006 |
| WO | 2007005633 A2 | 1/2007 |
| WO | 2009087474 A2 | 7/2009 |
| WO | 2009087474 A3 | 7/2009 |
| WO | 2009134460 | 11/2009 |
| WO | 2009134460 A1 | 11/2009 |
| WO | 2009145323 | 12/2009 |
| WO | 2010025303 A1 | 3/2010 |
| WO | 2011011781 A1 | 1/2011 |
| WO | 2012028620 A1 | 3/2012 |
| WO | 2013048558 A2 | 4/2013 |
| WO | 2013158145 A1 | 10/2013 |
| WO | 2014081977 | 5/2014 |
| WO | 2015048818 | 4/2015 |
| WO | 2015057747 | 4/2015 |
| WO | 2015063659 | 5/2015 |
| WO | 2015187641 | 12/2015 |
| WO | 2017147193 | 8/2017 |
| WO | 2017205515 | 11/2017 |
| WO | 2019051158 | 3/2019 |

OTHER PUBLICATIONS

Amended Complaint, Horizon Therapeutics, Inc. v. Lupin Ltd. And Lupin Pharmaceuticals Inc. Filed in U.S. District Court for the District of New Jersey, Apr. 6, 2016, 10 pgs.

Ammonul Product Specification, Cangene Biopharma Inc. Feb. 2005.

Amodio, P., et al., "Detection of Minimal Hepatic Encephalopathy: Normalization and Optimization of the Psychometric Hepatic Encephalopathy Score. A Neuropsychological and Quantified EEG Study," J. Hepatol. 49:346-353 (2008).

Anda Notice Letter, Lupin Ltd. to Horizon T herapeutics, Inc.. Re: Notitication of invalidity, Unenforceability, and/or Noninfringement for U.S. Pat. No. 8,404,215 and 8,642,012 Pursuant to 505(j)(2)(B)(ii) and (iv) of the Federal Food, Drug, and Cosmetic Act, Sep. 4, 2015.

Anda Notice Letter, Lupin Ltd. to Horizon Therapeutics, Inc.. Re: Notification of Invalidity, Unenforceability, and/or Noninfringement for U.S. Pat. No. 9,095,559 Pursuant to 505(j)(2)(B)(ii) and (iv) of the Federal Food, Drug, and Cosmetic Act, Nov. 6, 2015, 30 pgs.

Anda Notice Letter, Lupin Ltd. to Horizon Therapeutics, Inc.. Re: Notification of Invalidity, Unenforceability, and/or Noninfringement for U.S. Pat. No. 9,254,278 Pursuant to 505(j)(2)(B)(ii) and (iv) of the Federal Food, Drug, and Cosmetic Act, Apr. 13, 2016, 42 pgs.

Anda Notice Letter, Lupin Ltd. to Horizon Therapeutics, Inc.. Re: Notification of Invalidity, Unenforceability, and/or Noninfringement for U.S. Pat. No. 9,962,359 and 9,999,608 Pursuant to 505(j)(2)(B)(ii) and (iv) of the Federal Food, Drug, and Cosmetic Act, Aug. 6, 2018, 12 pgs.

Anda Notice Letter, Par Pharmaceutical, Inc. To Horizon Therapeutics, LLC.. Re: Glycerol Phenylbutyrate oral liquid 1.1 gm/ml; U.S. Pat. No. 9,962,359 and Notice of Paragraph IV Certification Jul. 23, 2018, 20 pgs.

Anda Notice Letter, Par Pharmaceutical, Inc. to Hyperion Therapeutics, inc.. Re: Glycerol Phenylbutyrate 1.1 gm/ml oral liquid; U.S. Pat. No. 8,404,215 and 8,642,012 Notice of Paragraph IV Certification Mar. 12, 2014, 27 pgs.

Andersson et al., Biochim. Biophys. Acta 1302: 236-240, 1996.

Anonymous, "Application No. 20-645 Medical Review FDA", (Feb. 15, 2005), pp. 1 55, URL: http://www.accessdata.fda.gov/drugsatfda_docs/nda/2005/020645s000_MedR.pdf, (Mar. 22, 2016), XP055260195.

Bajaj, J. S., et al., 'Review Article: The Design of Clinical Trials in Hepatic Encephalopathy—An International Society for Hepatic Encephalopathy and Nitrogen Metabolism (ISHEN) Consensus Statement,' Aliment Pharmacol Ther. 33 (7):739-747 (2011).

Barsotti, 'Measurement of Ammonia in Blood', 138 J. Pediatrics, S11-S20 (2001).

Batshaw M.L. et al. (Jun. 10, 1982) 'Treatment of Inborn Errors of Urea Synthesis: Activation of Alternative Pathways of Waste Nitrogen Synthesis and Excretion,' N Engl J Med 306(23):1387-1392.

Batshaw, M. L. et. al., Alternative Pathway Therapy for Urea Cycle Disorder: Twenty Years Later, 138 J. Pediatrics S46 (2001).

Batshaw, M.L. (1984). 'Hyperammonemia,' in Current Problems in Pediatrics, Lockhart, J.D. ed.: Year Book Medical Publishers, pp. 2-69.

Batshaw, M.L. et al. (Aug. 1981) 'New Approaches to the Diagnosis and Treatment of Inborn Errors of Urea Synthesis,' Pediatrics 68(2):290-297.

Batshaw, M.L. et al. (Dec. 1980). 'Treatment of Hyperammonemic Coma Caused by Inborn Errors of Urea Synthesis,' J. Pediatr. 97(6):893-900.

Batshaw, M.L. et al., Treatment of Carbamyl Phosphate Synthetase Deficiency with Keto Analogues of Essential Amino Acids, 292 The New England J. Medicine, 1085-1090 (1975).

Berry et al., Mol. Gen. and Metab. 122: 46-53, 2017.

Berry et al., Poster titled "Pharmacokinetics of glycerol phenylbutyrate in pediatric patients 2 months to 2 years of age with urea cycle disorder" presented at American Society of Human Genetics Meeting, Oct. 17-21, 2017.

Berry SA et al., Glycerol phenylbutyrate treatment in children with urea cycle disorders: pooled analysis of short and long-term ammonia control and outcomes, Mol Genet Metab. May 2014;112(1):17-24.

Berry, G. T., et al., 'Long-Term Management of Patients with Urea Cycle Disorders,' J. Pediatrics (2001) 138:S56-S61.

Blau, Duran, Blaskovics, Gibson (editors), Physcian's Guide to the Laboratory Diagnosis of Metabolic Diseases, 261-276 (2d ed. 1996).

Blei, A. T., et al., 'Hepatic Encephalopathy,' Am. J. Gastroenterol. 96(7): 1968-1976 (2001).

Brahe, C., et al., (2005) 'Phenylbutyrate Increases SMN Gene Expression in Spinal Muscular Atrophy Patients,' Eur J Hum Genet 13:256-259.

(56) References Cited

OTHER PUBLICATIONS

Brendan Lee et al, 'Blood ammonia and glutamine as predictors of hyperammonemic crises in patients with urea cycle disorder', Genetics in Medicine, US, (Dec. 11, 2014), vol. 17, No. 7, doi:10.1038/gim.2014.148, ISSN 1098-3600, pp. 561-568, XP055260189.
Brunetti-Pierri, N., et al., (2011) Phenylbutyrate Therapy for Maple Syrup Urine Disease, Hum Mol Genet 20(4):631-640.
Brusilow et al., Metabolism, vol. 42, No. 10 Oct. 1993, pp. 1336-1339, 'Restoration of Nitrogen Homeostasis in a Man with Ornithine Transcarbamylase Deficiency'.
Brusilow, S. W., 'Phenylacetylglutamine May Replace Urea as a Vehicle for Waste Nitrogen Excretion,' Ped. Res. 29(2):147-150(1991).
Brusilow, S.W. (1995). 'Urea Cycle Disorders: Clinical Paradigm of Hyperammonemic Enecphalopathy,' Chapter 12 in Progress in Liver Diseases pp. 293-309.
Brusilow, S.w. (Jun. 21, 1984). 'Treatment of Episodic Hyperammonemia in Children With Inborn Errors of Urea Synthesis,' N. Engl. J. Med. 310(25):1630-1634.
Brusilow, S.W. et al. (1995). 'Urea Cycle Enzymes,' Chapter 32 in the Metabolic and Molecular bases of Inherited Diseases, Scriver, C.R. et al. eds., McGraw-Hill, Inc. New York, pp. 1187-1232.
Brusilow, S.W., 'Protocols for Management of Intercurrent Hyperammonemia in Patients with Urea Cycle Disorders', FDA Application to Market a New Drug for Human Use or an Antibiotic Drug for Human Use, Fourteen pages (Amendment Dated Jul. 25, 1994).
Brusilow, S.W., et al. (Sep. 1, 1979) 'New Pathways of Nitrogen Excretion in Inborn Errors of Urea Synthesis,' Lancet 2(8140):452-454.
Brusilow, S.W., et al. (Feb. 8, 1980) 'Amino Acid Acylation: A Mechanism of Nitrogen Excretion in Inborn Errors of Urea Synthesis,' Science 207:659-661.
Brusilow, S.W., et al. (1991) 'Treatment of Urea Cycle Disorders,' Chapter 5 in Treatment of Genetic Diseases, Desnik, R.J. et al. eds, Churchill Livingstone, New York, New York, pp. 79-94.
Brusilow, S.W., et al. (1996) 'Urea Cycle Disorders: Diagnosis, Pathophysiology, and Therapy,' Adv Pediatr 43:127-170.
Burlina, A.B. et al., 'Long-Term Treatment with Sodium Phenylbutyrate in Ornithine Transcarbamylase-Deficient Patients', 72 Molecular Genetics and Metabolism 351-355 (2001).
Calloway, D.H. et al. (1971) 'Sweat and Miscellaneous Nitrogen Losses in Human Balance Studies,' J Nutrition 101:775-786.
Calloway, D.H. et al. (1971). 'Variation in Endogenous Nitrogen Excretion and Dietary Nitrogen Utilization as Determinants of Human Protein Requirements,' J. Nutrition 101:205-216.
Camacho, L.H. et al., Phase I Dose Escalation Clinical Trial of Phenylbutyrate Sodium Administered Twice Daily to Patients With Advanced Solid Tumors, 25 Invest. New Drugs 131-138 (2007, e-pub. Oct. 20, 2006).
Carducci, M., Phenylbutyrate Induces Apoptosis in Human Prostate Cancer and is More Potent Than Phenylacetate, 2 Clinical Cancer Research 379-387 (1996).
Carducci, M.A. et al., A Phase I Clinical and Pharmacological Evaluation of Sodium Phenylbutyrate on an 120-h Infusion Schedule, 7 Clin. Cancer Res. 3047-3055 (2001).
Center for Drug Evaluation and Research, Clinical Pharmacology and Biopharmaceutics Review for New Drug Application No. 20-645 (Ammonul) (2005), 34 pgs.
Center for Drug Evaluation and Research, Labeling for New Drug Application No. 20-645 (Ammonul.RTM.) (2005).
Center for Drug Evaluation and Research, Medical Review for New Drug Application No. 20-645 (Ammonul) (2005), 55 pgs.
Chang J.-G., et al., 'Treatment of Spinal Muscular Atrophy by Sodium Butyrate,' PNAS USA (2001) 98(17):9808-9813.
Chang, C.-S.; Wu, P.-L. 'Synthesis of triglycerides of phenybutyric acid by lipase', J. Molecular Catalysis B: Enzymatic 61, 117-122 (2009).
Chang, C.-S.; Wu, P.-L. 'Synthesis of triglycerides of phenylalkanoic acids by lipase-catalyzed esterification in a solvent-free system', J. Biotech. 127, 694-702 (2007).
Chem. abstr. vol. 123, No. 15, Oct. 9, 1995(Columbus, 4 OH, USA), p. 131 5, col. 1, the abstract No. 199405x, Degrado, WF. Preparation of radiolabeled platelet GPIIb/IIIa receptor antagonist as imaging agents for the diagnosis of thromboembolic disorders. WO 94-22494.
Chemical Abstract, vol. 116, No. 46308, Seiki et al, 'Homogenous Pharmaceutical Emulsions Containing Nonsteriodal Analogesics and Inflammation Inhibitors'. 1999.
Chemical Abstracts, vol. 112, No. 25, Jun. 18, 1990, (Columbus, Ohio, USA), p. 270, Abstract No. 231744t, Walsh J.P., "SN-1,2-Diacylglycerol Kinase of *Escherichia Coli*. Diacylglycerol Analogs Define Specificity and Mechanism"; Journal of Biological Chemistry, 1990, 265(8), (ENG).
Chen et al., 'Tributyrin: A Prodrug of Butyric Acid for Potential Clinical Applicaitn in Differentiation Therapy', Cancer Res., 54:3494-3499(1994).
Chung, Y.L., et al., (2000) "A Novel Approach for Nasopharyngeal Carcinoma Treatment Uese Phenylbutyrate as a Protein Kinase C Modulator: Implications for Radiosensitization and EBV-Targeted Therapy," Clin Cancer Res 6:1452-1458.
Clay, A. et. al, Hyperammonemia in the ICU, 132 Chest 1368-1378 (2007).
ClinicalTrials.Gov/Archive View of NCT00551200 on Dec. 11, 2007 'Dose-Escalation Safety Study of Glyceryl Tri (4-Phenylbutyrate)(GT4P) to Treat Urea Cycle Disorders' [accessed Oct. 5, 2009], 4 pages.
Collins, A.F. et al., Oral Sodium Phenylbutyrate Therapy in Homozygous Beta Thalassemia: A Clinical Trial, 85 Blood 43-49 (1995).
Combined Search and Examination Report dated Oct. 9, 2009 for Great Britain Patent Application No. GB0915545.8, filed on Aug. 27, 2009, eight pages.
Combined Search and Examination Report dated Sep. 9, 2010, for Great Britian Patent Application No. 1013468.2, filed on Aug. 27, 2009, six pages.
Complaint for Patent Infringement, Horizon Therapeutics, Inc. v. Lupin Ltd. and Lupin Pharmaceuticals Inc. Filed in U.S. District Court for the District of New Jersey, Oct. 19, 2015, 104 pgs.
Complaint for Patent Infringement, Horizon Therapeutics, LLC v. Par Pharmaceutical, Inc. and Par Pharmaceutical Companies, Inc., Filed in U.S. District Court for the District of Delaware, Aug. 10, 2018, 15 pgs.
Complaint for Patent Infringement, Hyperion Therapeutics, Inc. v. Par Pharmaceuticals, Inc. Filed in U.S. District Court for the Eastern District of Texas, Apr. 23, 2014, 14 pgs.
Complaint', Horizon Therapeutics, Inc. v. Lupin Ltd. et al.; U.S. District Court for the District of New Jersey; Civ. Action No. 1:16-cv-00438-RBK-JS; Filed Jul. 21, 2016.
Complaint', Horizon Therapeutics, Inc. v. Lupin Ltd. et al.; U.S. District Court for the District of New Jersey; Civ. Action No. 2:17-cv-05900-KM-MAH; Filed Aug. 8, 2017.
Complaint', Horizon Therapeutics, Inc. v. Par Pharmaceutical, Inc.; U.S. District Court for the District of New Jersey; Civ. Action No. 1:16-cv-03910-RBK-JS; Filed Jun. 30, 2016.
Complaint', Horizon Therapeutics, Inc. v. Par Pharmaceutical, Inc.; U.S. District Court for the District of New Jersey; Civ. Action No. 2:17-cv-05901-KM-MAH; Filed Aug. 8, 2017.
Comte, B. et al. (2002, e-pub. May 7, 2002). 'Identification of Phenylbutyrylglutamine, A New Metabolite of Phenylbutyrate Metabolism in Humans,' Journal of Mass Spectrometry 37(6):581-590.
Conn, H. O., et al., "Liver Physiology and Disease: Comparison of Lactulose and Neomycin in the Treatment of Chronic Portal-Systemic Encephalopathy. A Double Blind Controlled Trial," Gastroenterology 72(4):573-583 (1977).
Cordoba, J., "New assessment of hepatic encephalopathy", Journal of Hepatology, (2011), vol. 54, p. 1030, 1032, 1038, XP028192163.
Cudkowicz (2009) Phase 2 Study of Sodium Phenylbutyrate in ALS,—Amyotrophic Lateral Sclerosis 10:99-106.
Darmaun, D. et al., 'Phenylbutyrate-Induced Glutamine Depletion in Humans: Effect on Leucine Metabolism', 5 Am. J. of Physiology: Endocrinology and Metabolism E801 (1998).
Darzens, G. et al.: 'Preparation de quelques glycerides phenylaliphatiques et leur reduction en alcools . . .', Comptes Rendus Hebdomadaires Des Seances De L'Academie Des Sciences., vol. 205, 18 Oct. 1937, pp. 682-684.

(56) References Cited

OTHER PUBLICATIONS

Declaration of Bruce F. Scharschmidt, MD, executed on Dec. 5, 2017, 10 pages.
Declaration of Bruce F. Scharschmidt, MD, executed on Dec. 5, 2017, 9 pages.
Declaration of Bruce F. Scharschmidt, MD, executed on Jan. 3, 2018, 10 pages.
Deferrari, G. et al. (1981). 'Brain Metabolism of Amino Acids and Ammonia in Patients with Chronic Renal Insufficiency,' Kidney International 20:505-510.
Diaz G.A.et al, 'Ammonia (NH3) control and improved neurocognitive outcome among urea cycle disorder (UCD) patients treated with glycerol phenylbutyrate (GPB).' Mol. Genet. Metab. 2012,105, 311, SIMD Abstract 24.
Diaz, G. A., et aL., Ammonia control anD Neurocognitive Outcome Among urea Cycle Disorder Patients Treated with Glycerol Phenylbutyrate, Hepatology 57(6):2171-2179 (2013).
Diaz, G.A., et al., 'Phase 3 Blinded, Randomized, Crossover Comparison of Sodium Phenylbutyrate (NaPBA) and Glycerol Phenylbutyrate (GPB): Ammonia (NH3) Control in Adults with Urea Cycle Disorders (UCDs),' Mol. Genet. Metab. 102:276, Society of Inherited Metabolic Disease (SMID) Abstract, (2011).
Dixon, M. A. and Leonard, J.V., Intercurrent Illness in Inborn Errors of Intermediary Metabolism, 67 Archives of Disease in Childhood, 1387-1391 (1992).
Doi, et al., "Development of an Azanoradamantane-Type Nitroxyl Radical Catalyst for Class-Selective Oxidation of Alcohols," J Org Chem 80 (1), 401-413. Dec. 16, 2014.
Dover, G. et al, Induction of Fetal Hemoglobin Production in Subjects with Sickle Cell Anemia by Oral Sodium Phenylbutyrate, 84(1) Blood 339-343.
DSM Method of Analysis: Assay of Impurities in PERU 1 by HPLC (Oct. 21, 2011).
Endo, F. et al., Clinical Manifestations of Inborn Errors of the Urea Cycle and Related Metabolic Disorders During Childhood, 134 J. Nutrition 1605S (2004).
Enns et al., 'Survival after Treatment with Phenylacetate and Benzoate for Urea-Cycle Disorders', N Engl J Med., vol. 356, No. 22, (May 31, 2007), pp. 2282-2292, URL: http://www.nejm.org, XP055148817.
Enns GM (Author),Edited by Jess G. Thoene, Alternative waste nitrogen disposal agents for urea cycle disorders (Chapter 10), Small Molecule Therapy for Genetic Disease, Cambridge University Press., 2010, pp. 135-152.
European Medicines Agency, Annex I: Summary of Product Characteristics for Ammonaps, 1-33.
European Medicines Agency, European Public Assessment Report: Summary for the Public for Ammonaps (2009), 2 pgs.
European Medicines Agency, Scientific Discussion for Ammonaps (2005), 12 pgs.
European Medicines Agency, Scientific Discussion for Carbaglu (2004), 19 pgs.
European Patent Office, Extended European Search Report for EP09739263 completed Nov. 2, 2011, 6 pgs.
European Patent Office, International Search Report and Written Opinion for PCT/US2009/055256 completed Dec. 18, 2009 and dated Dec. 30, 2009, 13 pgs.
Examination Report for British Patent Application No. GB0915545.8 dated Oct. 27, 2010.
Examination Report for British Patent Application No. GB1013468.2 dated Oct. 28, 2011, 2 pgs.
Examination Report dated Feb. 5, 2010, for United Kingdom Patent Application No. GB0915545.8, filed on Aug. 27, 2009, two pages.
Examination Report dated May 11, 2010, for United Kingdom Patent Application No. GB0915545.8 filed on Aug. 27, 2009, one page.
Eydoux et al., J. Lipid. Res. 48: 1539-1549, 2007.
FDA Label for Ammonul, sixteen pages {Feb. 2005).
FDA Label for Carbagiu, seven pages. (Mar. 2010).
FDA. 'Buphenyl (Sodium Phenylbutyrate) Label' nine pages (Aug. 2003).
FDA. (Jul. 2007). 'Label for Buphenyl,' 6 pages.
Feillet, F. and Leonard, J.V., Alternative Pathway Therapy for Urea Cycle Disorders, 21 J. Inher. Metab. Dis. 101-111 (1998).
Feoli-Fonseca, M. L., Sodium Benzoate Therapy in Children with Inborn Errors of Urea Synthesis: Effect on Carnitine Metabolism and Ammonia Nitrogen Removal, 57 Biochemical and Molecular Medicine 31-36 (1996).
Ferenci, P., et al., 'Hepatic EncephalopathyDefinition, Nomenclature, Diagnosis, and Quantification: Final Report of the Working Party at the 11th World Congresses of Gastroenterology, Vienna, 1998,' Hepatology 35:716-721 (2002).
Fernandes, Saudubray, Berghe (editors), 'Inborn Metabolic Diseases Diagnosis and Treatment', 219-222 (3d ed. 2000).
Fey, et al., "Silica-Supported TEMPO Catalysts: Synthesis and Application in the Anelli Oxidation of Alcohols," J. Org. Chem., 2001, 66 (24), pp. 8154-8159.
Gargosky, S. 'Improved Survival of Neonates Following Administration of Ammonul (Sodium Phenyl acetate & Sodium Benzoate) 10% 110% Injection', SSIEM Poster, six pages (Aug. 2, 2005).
Gargosky, S. et al., 'Results of a Twenty-two Year Clinical Irial: Acute, Adjunctive Pharmacological Treatment of Hyperammonemic Episodes in Patients with Deficiencies in Enzymes of the Urea Cycle', poster, Ucyclyd Pharma, Inc., one page (Oct. 14, 2005).
Gargosky, s., High Ammonia Levels Are Associated with Increased Mortality and Coma , Ucyclyd Pharma, Inc., one page (2006).
Geraghty, M.T. and Brusilow, S.W., Disorders of the Urea Cycle, in Liver Disease in Children 827-842 (F.J. Suchy et al., eds. 2001).
Ghabril, M. et al., Glycerol Phenylbutyrate (GPB) Administration in Patients with Cirrhosis and Episodic Hepatic Encephalopathy {HE), accepted for presentation at Digestive Disease Week (2012).
Ghabril, M., et al., 'Glycerol Phenylbutyrate in Patients With Cirrhosis and Episodic Hepatic Encephalopathy: A Pilot Study of Safety and Effect on Venous Ammonia Concentration,' Clinical Pharmacology in Drug Development 2 (3):278-284 (2013).
Gilbert, J. et al., A Phase I Dose Escalation and Bioavailability Study of Oral Sodium Phenylbutyrate in Patients with Refractory Solid Tumor Malignancies, 7 Clin. Cancer Research 2292-2300 (2001).
Gore, S. et al., 'Impact or the Putative Differentiating Agent sodium Phenylbutyrate on Myelodysplastic Syndromes and Acute Myeloid Leukemia', 7 Clin. Cancer Res. 2330 (2001).
Gropman, A. (2010) "Brain Imaging in Urea Cycle Disorders," Mol Genet Metab 100:S20-S30.
Gropman, A.L. et al. (2008) '1H MRS Identifies Symptomatic and Asymptomatic Subjects With Partial Ornithine Transcarbamylase Deficiency,' Mol. Genet. Metab. 95(1-2):21-30 (Sep.-Oct. 2008, e-pub. Jul. 26, 2008).
Gropman, A.L. et al., Neurological Implications of Urea Cycle Disorders, 30 J. Inherit Metab Dis. 865-879 (2007).
Gropman, A.L., et al., (2008) '1H MRS Allows Brain Phenotype Differentiation in Sisters with Late Onset Ornithine Transcarbamylase Deficiency (OTCD) and Discordant Clinical Presentations,' Mol Genet Metab 94(1):52-60.
Guidance for Industry, Jul. 2005 cited by applicantt o show proper dosage calculation. (Year 2005).
Häberle J etal., Suggested guidelines for the diagnosis and management of urea cycle disorders, Orphanet J Rare Dis. May 29, 2012;7:32.
Hassanein, T. I., et al., "Introduction to the Hepatic Encephalopathy Scoring Algorithm (HESA)," Dig. Dis. Sci. 53:529-538 (2008).
Hassanein, T. I., et al., "Randomized Controlled Study of Extracorporeal Albumin Dialysis for Hepatic Encephalopathy in Advanced Cirrhosis," Hepatology 46:1853-1862 (2007).
Hassanein, T., et al., 'Performance of the Hepatic Encephalopathy Scoring Algorithm in a Clinical Trial of Patients With Cirrhosis and Severe Hepatic Encephalopathy,' Am. J. Gastroenterol. 104:1392-1400 (2009).
Helsinn Advanced Synthesis, Analytical Method, 03-GLIO Related Substances (Sep. 2011).

(56) References Cited

OTHER PUBLICATIONS

Helsinn Summary Report of Analytical Methods Validation (May 23, 2011).
Hines, P., et al., (2008) 'Pulsed-Dosing with Oral Sodium Phenylbutyrate Increases Hemoglobin F in a Patient with Sickle Cell Anemia,' Pediatr Blood Cancer 50:357-359.
Hogarth, P., et al., (2007) 'Sodium Phenylbutyrate in Huntington's Disease: A Dose-Finding Study,' Mov Disord 22(13):1962-1964.
Honda, S. et al., Successful Treatment of Severe Hyperammonemia Using Sodium Phenylacetate Power Prepared in Hospital Pharmacy, 25 Biol. Pharm. Bull. 1244-1246 (2002).
Huang, H.H., et al., (2012) "Cannabinoid Receptor 2 Agonist Ameliorates Mesenteric Angiogenesis and Portosystemic Collaterals in Cirrhotic Rats," Hepatology 56:248-258.
Hyperion Therapeutics. 'Hyperion Therapeutics Announces Enrollment of First Patient in Phase 1/2 Clinical Trial of GT4P in Patients with Urea Cycle Disorders' Announcement, 1 page (Oct. 23, 2007).
Hyperion Therapeutics. 'Hyperion Therapeutics Announces Results for Phase II Study in Urea Cycle Disorders,' located at <http://www.hyperiontx.com/press/release/pr1238518388,> last visited on Apr. 27, 2011, three pages (Mar. 30, 2009).
Hyperion Therapeutics. "Hyperion Therapeutics Announces Presentation of Long Term Data on Ammonia Control in Pediatric Patients Treated with Ravicti® at the 12th International Congress of Inborn Errors of Metabolism and the Urea Cycle Disorder Satellite Symposium", Press Release, Sep. 3, 2013.
Hyperion Therapeutics. (Jun. 2, 2009.) Hyperion Therapeutics Announces Results of Phase I Study in Patients with Liver Cirrhosis, located at <http://www.hyperiontx.com/press/release/pr_1243891161>, last visited on Apr. 27, 2011, three pages.
International Application No. PCT/US1996/000940, International Search Report, dated Aug. 15, 1996, 1 page.
International Application No. PCT/US2009/030362, International Preliminary Report on Patentability, dated Mar. 1, 2011, filed on Jan. 7, 2009, seven pages.
International Application No. PCT/US2009/030362, International Search Report and Written Opinion, dated Mar. 2, 2009, filed on Jan. 7, 2009, 9 pages.
International Application No. PCT/US2012/028620, International Preliminary Report on Patentability (Ch I), completed Jun. 4, 2012 and dated Apr. 10, 2014, 7 pgs.
International Application No. PCT/US2012/028620, International Preliminary Report on Patentability (Ch II), completed Aug. 22, 2013 and dated Sep. 4, 2013, 16 pgs.
International Application No. PCT/US2012/028620; International Search Report and Written Opinion dated Jun. 4, 2012.
International Application No. PCT/US2012/54673, International Preliminary Report on Patentability (Ch II), dated Apr. 20, 2016.
International Application No. PCT/US2012/54673, International Search Report and Written Opinion, dated Nov. 20, 2012, 8 pgs.
International Application No. PCT/US2013/71333, International Preliminary Report on Patentability (Ch II), dated May 21, 2016, 17 pages.
International Application No. PCT/US2013/71333, International Search Report and Written Opinion, dated May 30, 2014, 8 pgs.
International Application No. PCT/US2014/058489, International Preliminary Report on Patentability (Ch I), dated Apr. 5, 2016. 7 pages.
International Application No. PCT/US2014/058489, International Search Report and Written Opinion dated Apr. 2, 2015, 8 pgs.
International Application No. PCT/US2014/060543, International Preliminary Report on Patentability (Ch I), dated Apr. 19, 2016 8 pages.
International Application No. PCT/US2014/060543, International Search Report and Written Opinion, dated Apr. 23, 2015, 9 pages.
International Application No. PCT/US2015/033700, International Preliminary Report on Patentability (Ch I), dated. Dec. 6, 2016, 8 pages.
International Application No. PCT/US2015/033700, International Search Report and Written Opinion dated Aug. 19, 2015, 10 pgs.
International Application No. PCT/US2017/018958, International Search Report and Written Opinion dated Aug. 31, 2017, 10 pages.
International Application No. PCT/US2017/018958; International Preliminary Report on Patentability, dated Sep. 7, 2018; 8 pages.
International Application No. PCT/US2017/034286, International Search Report and Written Opinion dated Nov. 30, 2017, 6 pages.
International Preliminary Report on Patentability dated Mar. 1, 2011, for PCT Application No. PCT/US2009/055256, filed on Aug. 27, 2009, six pages.
International Search Report and Written Opinion for PCT Application No. PCT/US2009/055256, dated Dec. 30, 2009, filed on Aug. 27, 2008, 13 pages.
IPR2015-01117, Inter Partes Review of U.S. Pat. No. 8,642,012, Petition, 186 pgs, dated Apr. 29, 2015.
IPR2015-01117, Inter partes review of U.S. Pat. No. 8,642,012, Final written decision 35 U.S.C. § 318 and 37 C.F.R. § 42.73.
IPR2015-01127, Inter Partes Review of U.S. Pat. No. 8,404,215 Petition dated Apr. 29, 2015.
IPR2015-01127, Inter partes review of U.S. Pat. No. 8,404,215, Final written decision 35 U.S.C. § 318 and 37 C.F.R. § 42.73.
IPR2016-00283, Inter partes review of U.S. Pat. No. 8,642,012, Final written decision 35 U.S.C. § 318 and 37 C.F.R. § 42.73.
IPR2016-00283, Inter partes review of U.S. Pat. No. 8,642,012, Petition, pursuant to §§ 35 U.S.C. 311-319 and 37 C.F.R. § 42, dated Dec. 4, 2015.
IPR2016-00284, Inter partes review of U.S. Pat. No. 8,404,215, Final written decision 35 U.S.C. § 318 and 37 C.F.R. § 42.73.
IPR2016-00284, Inter partes review of U.S. Pat. No. 8,404,215, Petition, pursuant to §§ 35 U.S.C. 311-319 and 37 C.F.R. § 42, dated Dec. 4, 2015.
IPR2016-00829, Inter partes review of U.S. Pat. No. 9,095,559, Patent owner response.
IPR2016-00829, Inter partes review of U.S. Pat. No. 9,095,559, Petition, pursuant to §§ 35 U.S.C. 311-319 and 37 C.F.R. § 42, dated Apr. 1, 2016.
IPR2017-01159, Inter partes review of U.S. Pat. No. 9 9,254,278, Petition, pursuant to §§ 35 U.S.C. 311-319 and 37 C.F.R. § 42.
IPR2017-01159, Inter partes review of U.S. Pat. No. 9 9,254,278, Preliminary Patent Owner Response.
IPR2017-01160, Inter partes review of U.S. Pat. No. 9,326,966, Petition, pursuant to §§ 35 U.S.C. 311-319 and 37 C.F.R. § 42.
IPR2017-01160, Inter partes review of U.S. Pat. No. 9,326,966, Preliminary Patent Owner Response.
IPR2017-01767, Inter partes review of U.S. Pat. No. 9,254,278, Petition, pursuant to §§ 35 U.S.C. 311-319 and 37 C.F.R. § 42.
IPR2017-01768, Inter partes review of U.S. Pat. No. 9,095,559, Petition, pursuant to §§ 35 U.S.C. 311-319 and 37 C.F.R. § 42.
IPR2017-01769, Inter partes review of U.S. Pat. No. 9,326,966, Petition, pursuant to §§ 35 U.S.C. 311-319 and 37 C.F.R. § 42.
IPR2018-01550, Inter partes review of U.S. Pat. No. 9,561,197, Petition, pursuant to §§ 35 U.S.C. 311-319 and 37 C.F.R. § 42, dated Aug. 16, 2018, 60 pages.
James, M.O. et al. (1972). 'The Conjugation of Phenylacetic Acid in Man, Sub-Human Primates and Some Other Non-Primates Species,' Proc. R. Soc. London 182:25-35.
John, B.A., et al., 'The Disposition of HPN-100, A Novel Pharmaceutical Under Development for Potential Treatment of Hyperammonemia, in Cynomolgus Monkeys', ADMG 2009 ADME, poster, two pages (Mar. 2009).
John, Ba et al. (Mar. 2009). 'The Disposition of HPN-100, A Novel Pharmaceutical Under Development for Potential Treatment of Hyperammonemia, in Cynomologus Monkeys,' abstract presented at ACMG 2009, one page.
Jon P. R. Monteleone et al, 'Population Pharmacokinetic Modeling and Dosing Simulations of Nitrogen-Scavenging Compounds: Disposition of Glycerol Phenylbutyrate and Sodium Phenylbutyrate in Adult and Pediatric Patients with Urea Cycle Disorders', Journal of Clinical Pharmacology., US, (Jun. 15, 2013), vol. 53, No. 7, doi:10.1002/jcph.92, ISSN 0091-2700, pp. 699-710, XP055244763.
Kasumov, T. et al. (2004). 'New Secondary Metabolites of Phenylbutyrate in Humans and Rats,' Drug Metabolism and Disposition 32(1 ):10-19.

(56) References Cited

OTHER PUBLICATIONS

Khungar V et al, 'Management of Overt Hepatic Encephalopathy', Clinics in Liver Disease 2012 W.B. Saunders USA, (Feb. 2012), vol. 16, No. 1, ISSN 1089-3261, pp. 73-89, XP008179943.
Kleppe, S. et al., 'Urea Cycle Disorders', 5 Current Treatment Options in Neurology 309-319 (2003).
Koya, Toshinari et al., Poster Session, Liver P-397, A study of administration of granular preparations of branched chain amino acids during transcatheter arterial chemoembolisation for hepatocellular carcinoma, Department of Gastrointestinal Medicine, Anjo Kosei Hospital, 2017, p. A775.
Kubota, K. and Ishizaki, T., Dose-Dependent Pharmacokinetics of Benzoic Acid Following Oral Administration of Sodium Benzoate to Humans, 41 Eur. J. Clin. Pharmacol. 363-368 (1991).
Lea et al., 'Butyramide and Monobutyrin: Growth Inhibitory and Differentiating Agents', Anticancer Res., 13: 145-150 (1993).
Lee, B. and Goss, J., Long-Term Correction of Urea Cycle Disorders, 138 J. Pediatrics S62-S71 (2001).
Lee, B. et al. (2009) 'Dosing and Therapeutic Monitoring of Ammona Scavenging Drugs and Urinary Phenylacetylglutamine (PAGN) as a Biomarker: Lessons From A Phase 2 Comparison of a Novel Ammonia Scavenging Agent with Sodium Phenylbutyrate (NAPBA),' "abstract" presented at ICIEM 2009, San Diego, CA, poster, one page.
Lee, B. et al. (2009) 'Dosing and Therapeutic Monitoring of Ammona Scavenging Drugs and Urinary Phenylacetylglutamine (PAGN) as a Biomarker: Lessons From a Phase 2 Comparison of a Novel Ammonia Scavenging Agent with Sodium Phenylbutyrate (NAPBA),' presented at ICIEM 2009, San Diego, CA, poster, one page.
Lee, B. et al. (2009) 'Phase 2 Study of A Novel Ammonia Scavenging Agent in Adults With Urea Cycle Disorders (UCDs),' abstract presented at ACMG 2009, one page.
Lee, B. et al. (Aug. 2008). 'Preliminary Data on Adult Patients with Urea Cycle Disorders (UCD) in an Open-Label, Swirch-Over, Dose Escalation Study Comparing a New Ammonia Scavenger, Glyceryl Tri (4-Phenylbutyrate) [HPN-100], to Buphenyl (Sodium Phenylbutyrate [PBA])', abstract presented at SSSIEM 2008, Lisbon, Portugal, one page.
Lee, B. et al., "Phase 2 Study of a Novel Ammonia Scavenging Agent in Adults with Urea Cycle Disorders (UCDs)", presented at ACMG 2009, seventeen pages (Mar. 2009).
Lee, B. et al., "Preliminary Data on Adult Patients with Urea Cycle Disorders (UCD) in an Open-Label, Switch-Over, Dose Escalation Study Comparing a New Ammonia Scavenger, Glyceryl Tri (4-Phenylbutyrate) [HPN-100], to Buphenyl® (Sodium Phenylbutyrate [PBA])", presented at SSIEM 2008, Lisbon, Portugal, Poster, one page (Sep. 2008).
Lee, B. et al., Considerations in the Difficult-to-Manage Urea Cycle Disorder Patient, 21 Crit. Care Clin. S19-S25 (2005).
Lee, B., et al., 'Optimizing Ammonia (NH3) Control in Urea Cycle Disorder (UCD) Patients: A Predictive Model,' Oral Abstract Platform Presentations, Biochemical Genetics, Phoenix, AZ, Mar. 22, 2013, 2 pgs.
Lee, B., et al., 'Phase 2 Comparison of a Novel Ammonia Scavenging Agent with Sodium Phenylbutyrate in Patients with Urea Cycle Disorders: Safety, Pharmacokinetics and Ammonia Control,' Mol. Genet. Metab. 100(3):221-228 (2010).
Lee, B., et al., "Preliminary Data on Adult Patients with Urea Cycle Disorders (UCD) in an Open-Label, Switch-Over, Dose-Escalation Study Comparing a New Ammonia Scavenger, Glyceryl Tri(4-Phenylbutyrate) (HPN-100), to Buphenyl (Sodium Phenylbutyrate [PBA])", 31 J. Inherit. Metab. Dis. 91 (2008).
Leonard, J.V., Urea Cycle Disorders, 7 Semin. Nenatol. 27-35 (2002).
Levin, B. et al. "Hyperammonaemia: A Variant Type of Deficiency of Ornithinine Transcarbamylase." Arch. Dis. Childhd. 1969, 44, 162-169.

Lewis, H.B. (1914). 'Studies in the Synthesis of Hippuric Acid in the Animal Organism. II. The Synthesis and Rate of Elimination of Hippuric Acid After Benzoate Ingestion in Man,' J. Biol. Chem. 18:225-231.
Liang, K.Y., et al., 'Longitudinal Data Analysis Using Generalized Linear Models,' Biometrika 73(1):13-22 (1986).
Lichter-Konecki, U., et al., 'Ammonia Control in Children with Urea Cycle Disorders (UCDs); Phase 2 Comparison of Sodium Phenyl butyrate and Glycerol Phenylbutyrate,' Mol Genet Metab 103:323-329 (2011).
Lindquist and Hernell, Curr Opin Clin Nutr Metab Care 13: 314-320, 2010.
Lizardi-Cervera, J. et al, 'Hepatic Encephalopathy: A Review', 2 Annals of Hepatology 122-120 (2003).
MacArthur, R. B., et al., 'Pharmacokinetics of sodium phenylacetate and soium benzoate following intravenous administrtion as both a bolus and continuous infusion to healthy adult volunteers.' Mol Genet Metab 81 :(1 ):S67-S73 (2004).
Maestri NE, et al., Prospective treatment of urea cycle disorders. J Paediatr 1991 ;119:923-928.
Maestri, N.E. et al., 'Plasma Glutamine Concentration: A Guide in the Management of Urea Cycle Disorders', 121 J. Pediatrics 259 (1992).
Maestri, N.E., et al., Long-Term Survival of Patients with Argininosuccinate Synthetase Deficiency, 127 J. Pediatrics 929-935 (1993).
Maestri, N.E., Long-Term Treatment of Girls with Ornithine Transcarbamylase Deficiency, 355 N. Engl. J. Med. 855-859 (1996).
Majeed, K., Hyperammonemia, eMedicine.com (Dec. 2001), 12 pgs.
Mansour, A. et al. (Oct. 1997). 'Abdominal Operations in Patients with Cirrhosis: Still a Major Surgical Challenge,' Surgery 122(4):730-735. (Abstract Only.).
Marini, J.C. et al., Phenylbutyrate Improves Nitrogen Disposal via an Alternative Pathway without Eliciting an Increase in Protein Breakdown and Catabolism in Control and Ornithine Transcarbamylase-Deficient Patients, 93 Am. J. Clin. Nutr. 1248-1254 (2011).
Mas et al., Biochem J. 289: 609-615, 1993.
Mas et al., Methods Enzymol. 284: 340-353, 1997.
Matsuda, I., Hyperammonemia in Pediatric Clinics: A Review of Ornithine Transcarbamylase Deficiency (OTCD) Based on our Case Studies, 47 JMAJ 160-165 (2004).
McGuire et al, Hepatology Jun. 2010; 51(6): 2077-2085.
McGuire, B. et al. (2009) 'Pharmacokinetic (PK) and Safety Analyses of a Novel Ammonia-Reducing Agent in Healthy Adults and Patients with Cirrhosis,' abstract presented at DDW, two pages.
McGuire, B. et al. (2009) 'Pharmacokinetic (PK) and Safety Analyses of a Novel Ammonia-Reducing Agent in Healthy Adults and Patients with Cirrhosis,' Hyperion Therapeutics, poster, one page.
McGuire, B. et al., 'Pharmacokinetic <PK) Safety Study of Sodium Phenylacetate and Sodium Benzoate Administered to Subjects with Hepatic Impairment', abstract of The 13th International Symposium, Abano (Padova), Italy, Apr. 28-May 1, 2008, two pages (Apr. 2008).
McGuire, B. et al., "Pharmacokinetic Safety Study of Sodium Phenylacetate and Sodium Benzoate Administered to Subjects With Hepatic Impairments", 28 Liver International 743 (2008) (Abstract Only), 1 page.
McGuire, B. et al., (2010) 'Pharmacology and Safety of Glycerol Phenylbutyrate in Healthy Adults and Adults with Cirrhosis,' Hepatology 51:2077-2085.
McQuade, P.S., Analysis and the Effects of Some Drugs on the Metabolism of Phenylethylamine and Phenylacetic Acid, 8 Neuropsychopharmacol. Bio. Psychiat.607-614 (1984).
MedCalc: Body Surface Area, Body Mass Index (BMI), Jan. 15, 2000.
Mercuri, E, et al, (2004) 'Pilot Trial of Phenylbutyrate in Spinal Muscular Atrophy,' Neuromuscul Disord 14:130-135.
Mizutani, N. et al., Hyperargininemia: Clinical Course and Treatment with Sodium Benzoate and Phenylacetic Acid, 5 Brain and Development 555-563 (1983).
Mokhtarani et al., (2012) 'Urinary phenylacetylglutamine appears to be a more useful marker than metabolite blood levels for

(56) References Cited

OTHER PUBLICATIONS therapeutic monitoring of phenylacetic acid (PAA) prodrugs.' Mol Genet Metab 105, 341-342, SIMD Abstract 78.
Mokhtarani, M, et al, (2012) 'Elevated Phenylacetic Acid (PAA) Levels Appear Linked to Neurological Adverse Events in Healthy Adults But Not in Urea Cycle Disorder (UCD) Patients,' Mol Genet Metab 105:342.
Mokhtarani, M., et al., 'Elevated Phenylacetic Acid Levels do not Correlate with Adverse Events in Patients with Urea Cycle Disorders or Hepatic Encephalopathy and Can Be Predicted Based on the Plasma PAA to PAGN Ratio,' Mol. Genet. Metab. 110(4):446-53 (2013).
Mokhtarani, M., et al., 'Urinary Phenylacetylglutamine as Dosing Biomarker for Patients with Urea Cycle Disorders,' Mol. Genet. Metab. 107(3):308-314 (2012).
Moldave, K, et al, (1957) 'Synthesis of Phenylacetylglutamine by Human Tissue,' J. Biol. Chem. 229:463-476.
Monteleone, JPR, et al., (2012) 'Population pk Analysis of Glycerol Phenylbutyrate (GPB) and Sodium Phenylbutyrate(NAPBA) in Adult and Pediatric Patients with Urea Cycle Discarders,' Mol Genet Metab 105:343-344.
Munoz, S. J, 'Hepatic Encephalopathy,' Med. Clin. N. Am. 92:795-812 (2008).
Nagazumi Atsushi et al., Use experience of Monilac for hepatic encephalopathy, Journal of New Remedies & Clinics, vol. 24, No. 8, Aug. 1975, pp. (1271-1274) 41-44.
Nakamura, I., Ammonia (NH3), Japan Clinical (Extra Published) Extensive Blood and Urinalysis Test, Immunological Test (7th Edition) 1, 2009, vol. 67 (Newly cited document; document showing well-known technology).
Nassogne, M.C., Urea Cycle Defects: Management and Outcome, 28 J. Inherit. Metab. Dis. 407 (2005), 407-414.
National Center for Biotechnology Information. PubChem Compound Database; CID=10482134, https://pubchem.ncbi.nlm.nih.gov/compound/10482134 (accessed Jun. 8, 2018; create date: Oct. 25, 2006). (Year: 2006).
NCT00947297, Clinical Trial.gov archive, May 3, 2011.
NCT01347073 Clinical Trial.gov archive, May 3, 2011, Study of the safety, Pharmacokinetics and Efficacy of HPN-100, in Pediatric Subjects with Urea Cycle Dosorders (UCDs) 2011, 8 pages.
New England Consortium of Metabolic Programs, Acute Illness Protocol: Urea Cycle Disorders: The Infant/Child with Argininosuccinate Lyase Deficiency, adapted from Summar, M and Tuchman, M, Proceedings of a Consensus Conference for the Management of Patients with Urea Cycle Disorders, 138 J. Peds. Suppl. (2001), 7 pgs.
New England Consortium of Metabolic Programs, Acute Illness Protocol: Urea Cycle Disorders: The Infant/Child with Citrullinemia, adapted from Summar, M and Tuchman, M, Proceedings of a Consensus Conference for the Management of Patients with Urea Cycle Disorders, 138 J. Peds. Suppl. (2001), 7 pgs.
Newmark et al., 'Butyrate and Phenylacetate as Differentiating Agents: Practical Problems and Opportunities', Jour. of Cell. Biochem., Supplement 22: 247-253(1995).
Ong, J. P., et al., (2003) 'Correlation Between Ammonia Levels and the Severity of Hepatic Encephalopathy,' Am. J. Med. 114:188-193.
Ortiz, M., et al., "Development of a Clinical Hepatic Encephalopathy Staging Scale," Aliment Pharmacol Ther 26:859-867 (2007).
Par Pharmaceutical, Inc.S Initial Invalidity Contentions and Non-Infringement Contentions for U.S. Pat. No. 8,404,215 and 8,642,012, dated Nov. 13, 2014, 93. Pgs.
Parsons-Smith, B. G., et al., "The Electroencephalograph in Liver Disease," Lancet 273:867-871 (1957).
Perrine, S. P., (2008) 'Fetal Globin Stimulant Therapies in the Beta-Hemoglobinopathies: Principles and Current Potential,' Pediatr Ann 37(5):339-346.
Phuphanich, S. et al., Oral Sodium Phenylbutyrate in Patients with Recurrent Malignant Gliomas: A Dose Escalation and Pharmacologic Study, Neuro-Oncology 177 (2005).

Piscitelli, S.C. et al. (1995). 'Disposition of Phenyl butyrate and its Metabolites, Phenylacetete and Phenylacetylglutamine,' J. Clin. Pharmacal. 35:368-373.
Praphanproj, V. et al., Three Cases of Intravenous Sodium Benzoate and Sodium Phenylacetate Toxicity Occurring in the Treatment of Acute Hyperammonemia, 23 J. Inherited Metabolic Disease 129-136 (2000).
Priester, T. et al., "Hyperammonemia from a Urea Cycle Disorder Presenting in Adulthood", Open Critical Care Medicine Journal, 2009; 2:9-12.
Product Monograph including patient medication information RAVICTI; Mar. 16, 2016 (Year: 2016), 28 pages.
Propst, A. et al, 'Prognosis and Lite Expectancy in Chronic Liver Disease', 40 Dig Dis Sci 1805 (1995) (Abstract Only).
RAVICTI (glycerol phenylbutyrate) oral liquid, US Prescribing Information 2013.
RAVICTI (glycerol phenylbutyrate) oral liquid, US Prescribing Information 2016.
Riley, T.R. et al. (Nov. 15, 2001). 'Preventive Strategies in Chronic Liver Disease: Part II. Cirrhosos,' Am. Fam. Physician 64(10):1735-1740. (Abstract Only).
Rockey, D. C., et al., 'Randomized, Controlled, Double Blind Study of Glycerol Phenylbutyrate in Patients with Cirrhosis and Episodic Hepatic Encephalopathy,' Hepatology 56:248(a) (2012), 1 pge.
Rose CF, Ammonia-lowering strategies for the treatment of hepatic encephalopathy, Clin Pharmacol Ther. Sep. 2012;92(3):321-31.
Rudman, D., et al., Maximal Rates of Excretion and Synthesis of Urea in Normal and Cirrhotic Subjects, 52 J. Clin. Invest. 2241-2249 (1973).
Ruvoen-Clouet et al., Biochem J. 393: 627-634, 2006.
Ryu, H, et al, (2005) 'Sodium Phenylbutyrate Prolongs Survival and Regulates Expression of Anti-Apoptotic Genes in Transgenic Amyotrophic Lateral Sclerosis Mice,' J Neurochem 93:1087-1098.
Salam, M, et al, 'Modified-Orientation Log to Assess Hepatic Encephalopathy,' Aliment Pharmacol Ther. 35(8):913- 920 (2012).
Scientific Discussion for Ammonaps, EMEA 2005, available at http://www.ema.europa.eu/docs/enGB/document_library/EPAR-ScientificDiscussion/human/000219/WC500024748.pdf, 12 pgs.
Scottish Medicines Consortium, Carglumic Acid 200 mg Dispersible Tablets (Carbaglu) No. 299/06 (Sep. 8, 2006), 5 pgs.
Seakins, J.W.T., The Determination of Urinary Phenylacetylglutamine as Phenylacetic Acid: Studies on its Origin in Normal Subjects and Children with Cystic Fibrosis, 35 Clin. Chim. Acta.121-131 (1971).
Search and Examination Report for British Patent Application No. GB 0915545.8, dated Oct. 8, 2009, 5 pages.
Sherwin, C. et al., The Maximum Production of Glutamine by the Human Body as Measured by the Output of Phenylacetylglutamine, 37 J. Biol. Chem. 113(1919).
Shibuya, et al, "Nitroxyl Radical/Phl(OAc)2: One-Pot Oxidative Cleavage of Vicinal Diols to (Di)Carboxylic Acids," 2012, Org. Lett., vol. 14, No. 19, pp. 5010-5013.
Shin Jang-Woo etal., Interpretation of Animal Dose and Human Equivalent Dose for Drug Development, The Journal of Korean Oriental Medicine, vol. 31. No. 3., 2010, pp. 1-7.
Shiple, G.J. et al., Synthesis of Amino Acids in Animal Organisms. I. Synthesis of Glycocoll and Glutamine in the Human Organism, 44 J. Am. Chem. Soc. 618-624 (1922).
Sias et al., Biochemistry 43: 10138-10148, 2004.
Simell, O et al: 'Waste nitrogen excretion via amino acid acylation: Benzoate and phenylacetate in lysinuric protein intolerance' Pediatric Research, Williams and Wilkins, Baltimore, MD, US, vol. 20, No. 11, Jan. 1, 1986 (Jan. 1, 1986), pp. 1117-1121, XP009127277 ISSN: 0031-3998.
Singh, "Consensus Statement from a Conference for the Management of Patients with Urea Cycle Disorders", 138 J. Pediatrics S1-S5 (2001).
Smith, W. et al., Ammonia (NH3) Control in Children Ages 2 Months through 5 Years with Urea Cycle Disorders (UCDs): Comparison of Sodium Phenylbutyrate and Glycerol Phenylbutyrate, Poster Abstract 774W from American Society of Human Genetics 62nd Annual Meeting, Nov. 6-10, 2012, San Francisco, CA.

(56) References Cited

OTHER PUBLICATIONS

Smith, W., et al., "Ammonia Control in Children Ages 2 Months through 5 Years with Urea Cycle Disorders: Comparison of Sodium Phenylbutyrate and Glycerol Phenylbutyrate," J Pediatr. 162(6):1228-1234.e1 (2013).
South San et al, 'Hyperion Therapeutics Announces Presentation of Long Term Data on Ammonia Control in Pediatric Patients Treated With RAVICTI(R) at the 12th International Congress of Inborn Errors of Metabolism and the Urea Cycle Disorder Satellite Symposium', (Sep. 3, 2013), URL: http://files.shareholder.com/downloads/AMDA-1412CE/0x0x688110/4e684e9d-6c54-4963-a993-72c90f308802/HPTX_News_2013_9_3_General_Releases.pdf, (Mar. 21, 2016), XP055260208.
Spreadsheet showing impurity levels for various batches of RAVICTI®.
Stauch et al., 'Oral L-ornithine-L-aspartate therapy of chronic hepatic encephalopathy: results of a placebo-controlled double-blind study', Journal of Hepatology, vol. 28, No. Issue, (May 1998), pp. 856-864, URL: http://www.sciencedirect.com, XP055250053.
Summar, M. and Tuchman, M., Proceedings of a Consensus Conference for the Management of Patients with Urea Cycle Disorders, 138 J. Pediatrics S6-S10 (2001).
Summar, M. et al., 'Description and Outcomes of 316 Urea Cycle Patients From a 21-Year, Multicenter Study of Acute Hyperammonemic Episodes', Abstract, presented at Annual Symposium CCH-Congress Centre Hamburg, Sep. 4-7, 2007, GSSIEM 2007, two pages.
Summar, M. et al., Unmasked Adult-Onset Urea Cycle Disorders in the Critical Care Setting, 21 Crit. Care Clin. S1-S8 (2005).
Summar, M., Current Strategies for the Management of Neonatal Urea Cycle Disorders, 138 J. Pediatrics S30-S39 (2001).
Summar, M., Urea Cycle Disorders Overview, Gene Reviews, www.genetests.org (Apr. 2003), 15 pgs.
Summar, M.L. et al., Diagnosis, Symptoms, Frequency and Mortality of 260 Patients with Urea Cycle Disorders From a 21-Year, Multicentre Study of Acute Hyperammonemic Episodes, 97 Acta Paediatr. 1420-1425 (Oct. 2008, e-pub. Jul. 17, 2008).
Sushma, S. et al., 'Sodium Benzoate in the Treatment of Acute Hepatic Encephalopathy: A Randome Double-blind Trial,' Hepatology, 16 (1992), 138-144.
Swedish Orphan International, 'Urea Cycle Disorders an International Perspective', Poster, Symposium Swedish Orphan International, Barcelona, Spain, Jan. 12, 2007, one page. (2007).
Tanner, L. M., et al., Nutrient Intake in Lysinuric Protein Intolerance, 30 J. Inherit. Metab. Dis. 716 (2007), 716-721.
The National Organization for Rare Disorders (2012). The Physician's Guide to Urea Cycle Disorders, at http://nordphysicianguides.org/wp-content/uploads/2012/02/NORD_Physician_Guide_to_Urea_Cycle_Disorders.pdf, 28 pgs.
Thibault, A., et al., 'A Phase I and Pharmacokinetic Study of Intravenous Phenylacetate in Patients with Cancer,' Cancer Res. 54:1690-1694 (1994).
Thibault, A., et al., 'Phase I Study of Phenylacetate Administered Twice Daily to Patients with Cancer,' Cancer 75:2932-2938 (1995).
Thompson, P. 'Pharmacokinetics of phenyacetate administered as a 30-min infusion in children with refractory cancer', Cancer Chemother. Pharmacol. 2003, 52: 417-423.
Todo, S. et al., Orthotopic Liver Transplantation for Urea Cycle Enzyme Deficiency, 15 Hepatology 419-422 (1992).
Tuchman, M. et al. (2008, e-pub. Jun. 17, 2008). 'Cross-Sectional Multicenter Study of Patients With Urea Cycle Disorders in the United States,' Malec. Genetics Metab. 94:397-402.
Tuchman, M., and Yudkoff, M., Blood Levels of Ammonia and Nitrogen Scavenging Amino Acids in Patients with Inherited Hyperammonemia, 66 Molecular Genetics and Metabolism 10-15 (1999).
U.S. Appl. No. 16/057,335; Non-Final Office Action dated Oct. 19, 2018; 67 pages.
UMass Memorial Medical Center, Lab Updates, 'Measurement of Ammonia in Blood.' Feb. 2007. Accessed at www.ummlabs.org/News/07Feb.pdf, 3 pgs.
Uribe, M. et al., "Hyperammonemic Hepatic Encypholopathy Treated with Sodium Benzoate, Final report of double blind evaluation", Instituto Nacional de la Nutricion, Mexico D.F., Hepatology, 10(4):589, (1989).
U.S. Appl. No. 15/074,625, Non-Final Office Action, dated Aug. 8, 2016, 19 pages.
U.S. Appl. No. 15/074,666, Non-Final Office Action, dated Aug. 30, 2016, 20 pages.
U.S. Appl. No. 09/006,432, Non-Final Office Action, dated Oct. 13, 1998, 4 pages.
U.S. Appl. No. 09/006,432, Notice of allowance, dated Feb. 2, 1999, 3 pages.
U.S. Appl. No. 12/350,111, Applicant Initiated Interview Summary, dated Dec. 12, 2012.
U.S. Appl. No. 12/350,111, Examiner Initiated Interview Summary dated Sep. 30, 2013.
U.S. Appl. No. 12/350,111, Final Office Action, dated Nov. 18, 2011, 15 pages.
U.S. Appl. No. 12/350,111, Non-Final Office Action, dated Jun. 18, 2012, 16 pages.
U.S. Appl. No. 12/350,111, Non-Final Rejection, dated Jul. 21, 2011.
U.S. Appl. No. 12/350,111, Notice of allowance, dated Sep. 30, 2013.
U.S. Appl. No. 13/417,137, Non-Final Office Action, dated Nov. 21, 2012, 11 pages.
U.S. Appl. No. 13/417,137, Notice of allowance,dated Jan. 2, 2013, 8 pages.
U.S. Appl. No. 13/610,580, Final Office Action, dated May 19, 2016, 13 pages.
U.S. Appl. No. 13/610,580, Non-Final Office Action, dated Feb, 27, 2015, 13 pages.
U.S. Appl. No. 14/086,870, Examiner Initiated Interview Summary dated Jun. 23, 2015, 1 page.
U.S. Appl. No. 14/086,870, Final Office Action, dated Apr. 7, 2015, 10 pages.
U.S. Appl. No. 14/086,870, Non-Final Office Action, dated Nov. 7, 2014, 11 pages.
U.S. Appl. No. 14/086,870, Notice of allowance, dated Jun. 23, 2015, 7 pages.
U.S. Appl. No. 14/135,318, Non-Final Office Action, dated Aug. 20, 2014, 9 pages.
U.S. Appl. No. 14/503,261, Final Office Action, dated May 5, 2016, 12 pages.
U.S. Appl. No. 14/503,261, Non-Final Office Action, dated Nov. 4, 2015, 16 pages.
U.S. Appl. No. 14/514,334, Appeal Brief filed, dated Apr. 4, 2018, 16 pages.
U.S. Appl. No. 14/514,334, Appeal Brief filed, dated Nov. 2, 2017, 17 pages.
U.S. Appl. No. 14/514,334, Examiner Answer to Appeal Brief, dated May 17, 2018, 19 pages.
U.S. Appl. No. 14/514,334, Final Office Action, dated Mar. 28, 2016, 8 pages.
U.S. Appl. No. 14/514,334, Final Office Action, dated Nov. 2, 2016, 10 pages.
U.S. Appl. No. 14/514,334, Non-Final Office Action, dated Aug. 14, 2015, 7 pages.
U.S. Appl. No. 14/514,334, Non-Final Office Action, dated Jan. 29, 2018, 9 pages.
U.S. Appl. No. 14/514,334, Non-Final Office Action, dated Jul. 15, 2016, 11 pages.
U.S. Appl. No. 14/816,674, Non-Final Office Action, dated Nov. 3, 2015, 9 pages.
U.S. Appl. No. 14/816,674, Notice of allowance, dated Dec. 23, 2015, 9 pages.
U.S. Appl. No. 14/939,127, Examiner Initiated Interview Summary, dated Mar. 11, 2016, 1 page.
U.S. Appl. No. 14/939,127, Non-Final Office Action, dated Mar. 11, 2016, 13 pages.
U.S. Appl. No. 14/958,259, Non-Final Office Action, dated Feb. 5, 2016, 11 pages.

(56) References Cited

OTHER PUBLICATIONS

U.S. Appl. No. 14/958,259, Notice of allowance, dated Mar. 8, 2016, 8 pages.
U.S. Appl. No. 15/043,859, Non-Final Office Action, dated Feb. 8, 2017, 11 pages.
U.S. Appl. No. 15/074,691, Non-Final Office Action, dated Sep. 14, 2016, 18 pages.
U.S. Appl. No. 15/074,716, Non-Final Office Action, dated Jul. 28, 2016, 18 pages.
U.S. Appl. No. 15/164,126, Non-Final Office Action, dated Aug. 24, 2017, 10 pages.
U.S. Appl. No. 15/164,126, Notice of Allowance, dated Aug. 24, 2017, 5 pages.
U.S. Appl. No. 15/238,149, Non-Final Office Action, dated May 17, 2018, 41 pages.
U.S. Appl. No. 15/316,049, Non-Final Office Action, dated Apr. 9, 2018, 8 pages.
U.S. Appl. No. 15/457,643, Examiner initiated interview summary, dated Apr. 4, 2018, p. 1.
U.S. Appl. No. 15/457,643, Non-Final Office Action, dated Feb. 2, 2018, 17 pages.
U.S. Appl. No. 15/457,643, Notice of allowance, dated Apr. 4, 2018, 9 pages.
U.S. Appl. No. 15/639,171, Non-Final Office Action, dated Apr. 12, 2018, 12 pages.
U.S. Appl. No. 15/672,196, Non-Final Office Action, dated Mar. 5, 2018, 15 pages.
U.S. Appl. No. 15/684,876, Non-Final Office Action, dated Mar. 9, 2018, 23 pages.
U.S. Appl. No. 15/687,118, Non-Final Office Action, dated Dec. 7, 2017, 16 pages.
U.S. Appl. No. 15/687,118, Notice of Allowance, dated Mar. 9, 2018, 8 pages.
U.S. Appl. No. 15/687,132, Non-Final Office Action, dated Dec. 11, 2017, 18 pages.
U.S. Appl. No. 15/687,132, Notice of Allowance, dated Mar. 7, 2018, 9 pages.
U.S. Appl. No. 15/687,136, Non-Final Office Action, dated Apr. 20, 2018, 31 pages.
U.S. Appl. No. 15/687,136, Non-Final Office Action, dated Nov. 3, 2017, 10 pages.
U.S. Appl. No. 15/687,141, Applicant Initiated Interview Summary, dated Jun. 12, 2018, 2 pages.
U.S. Appl. No. 15/687,141, Examiner Interview Summary Record, dated Jan. 19, 2018, 2 pages.
U.S. Appl. No. 15/687,141, Non-Final Office Action, dated, Jan. 19, 2018, 11 pages.
U.S. Appl. No. 15/687,144, Applicant Initiated Interview Summary, dated Jun. 12, 2018, 2 pages.
U.S. Appl. No. 15/687,144, Final Office Action, dated Jul. 10, 2018, 17 pages.
U.S. Appl. No. 15/687,144, Non-Final Office Action, dated Jan. 23, 2018, 16 pages.
U.S. Appl. No. 15/696,448 , Non-Final Office Action, dated Jun. 14, 2018, 37 pages.
U.S. Appl. No. 15/699,188, Preinterview first office action, dated Dec. 12, 2017, 6 pages.
U.S. Appl. No. 15/699,209, Final Office Action, dated Apr. 2, 2018, 15 pages.
U.S. Appl. No. 15/699,209, Non-Final Office Action, dated Dec. 17, 2017, 21 pages.
U.S. Appl. No. 15/816,711, Application as filed, filed Nov. 17, 2017, 31 pages.
U.S. Appl. No. 15/816,711, Non-Final Office Action, dated Jun. 18, 2018, 34 pages.
U.S. Appl. No. 15/944,398, Application as filed, filed Mar. 29, 2018, 38 pages.
U.S. Appl. No. 15/944,398, Non-Final Office Action, dated May 25, 2018, 40 pages.
U.S. Appl. No. 15/944,398, Notice of Allowance, dated Jun. 26, 2018, 10 pages.
U.S. Appl. No. 15/944,411, Examiner Initiated Interview Summary, dated Jun. 26, 2018, 2 pages.
U.S. Appl. No. 15/944,411, Non-Final Office Action, dated Jun. 26, 2018, 33 pages.
U.S. Appl. No. 15/944,416, Application as filed, filed Mar. 29, 2018, 38 pages.
U.S. Appl. No. 15/944,416, Non-Final Office Action, dated May 25, 2018, 39 pages.
U.S. Appl. No. 15/944,416, Notice of Allowance, dated Jun. 29, 2018, 10 pages.
U.S. Appl. No. 15/944,422, Non-Final Office Action, dated Jun. 22, 2018, 40 pages.
U.S. Appl. No. 15/944,428, Non-Final Office Action, dated Jun. 22, 2018, 40 pages.
U.S. Appl. No. 15/944,432, Application as filed, filed Mar. 29, 2018, 38 pages.
U.S. Appl. No. 15/316,049, Non-Final Office Action, dated Aug. 28, 2018, 35 pages.
U.S. Appl. No. 15/402,780; Non-Final Office Action dated Aug. 23, 2018; 74 pages.
U.S. Appl. No. 15/684,876; Final Office Action dated Sep. 26, 2018; 44 pages.
U.S. Appl. No. 15/687,136; Advisory Action dated Sep. 25, 2018; 7 pages.
U.S. Appl. No. 15/687,136; Final Office Action dated Sep. 4, 2018; 31 pages.
U.S. Appl. No. 15/687,141; Advisory Action dated Aug. 30, 2018; 2 pages.
U.S. Appl. No. 15/687,144; Advisory Action dated Aug. 30, 2018; 3 pages.
U.S. Appl. No. 15/944,411, Notice of allowance, dated Sep. 19, 2018.
U.S. Appl. No. 15/944,422, Notice of allowance, dated Sep. 20, 2018.
U.S. Appl. No. 15/944,428, Notice of allowance, dated Sep. 21, 2018.
U.S. Appl. No. 15/944,432, Notice of allowance, dated Sep. 20, 2018.
U.S. Appl. No. 15/980,376, Non-Final Office Action, dated Aug. 16, 2018, 144 pages.
U.S. Appl. No. 15/980,431; Non-Final Office Action dated Aug. 3, 2018; 92 pages.
U.S. Appl. No. 16/057,335, Application as filed, filed Aug. 7, 2018, 31 pages.
U.S. Appl. No. 16/121,854; Application as filed, dated Sep. 5, 2018; 45 pages.
Vierling JM etal., Fasting Blood Ammonia Predicts Risk and Frequency of Hepatic Encephalopathy Episodes in Patients With Cirrhosis, Clin Gastroenterol Hepatol. Jun. 2016;14(6):903-906.
Vilstrup, H, et al, 'Hepatic Encephalopathy in Chronic Liver Disease: 2014 Practice Guideline by the American Association for the Study of Liver Diseases and the European Association for the Study of the Liver,' Hepatology 60 (2):715-735 (2014).
Walsh et al., Chemical Abstract vol. 112, No. 231744, 1990, 1 pge.
Walsh et al., The Journal of Biological Chemistry, vol. 265, No. 8, pp. 4374-4381 (1990), sn-1,2-Diacylglycerol Kinase of *Escherichia coli*.
Waterlow, J.C., The Partition of Nitrogen in the Urine of Malnourished Jamaican Infants, 12 Am. J. of Clin. Nutrition 235-240 (1963).
Welbourne, T. et al., 'The Effect of Glutamine Administration on Urinary Ammonium Excretion in Normal Subjects and Patients with Renal Disease', 51 J. Clin. Investigation 1852 {1972).
Wilcken, B, 'Problems in the Management of Urea Cycle Disorders', 81 Molecular Genetics and Metabolism 85 (2004).
Wilson, C.J, et al, 'Plasma Glutamine and Ammonia Concentrations in Ornithine Carbamoyltransferase Deficiency and Citrullinaemia', 24 J. Inherited Metabolic Disease 691 (2001).
Wright, G., et al., Management of Hepatic Encephalopathy, 2011 International Journal of Hepatology 1 (2011), 11 pgs.
Wright, P., Review: Nitrogen Excretion: Three End Products, Many Physiological Roles, 198 J. Experimental Biology 273-281 (1995).

(56) References Cited

OTHER PUBLICATIONS

Xiao et al., J Biol Chem. 286(30): 26353-26363, 2011.
Xie, G, et al, (2012) 'Role of Differentiation of Liver Sinusoidal Endothelial Cells in Progression and Regression of Hepatic Fibrosis in Rats,' Gastroenterology 142:S918.
Yajima, et al. 'Diurnal Fluctuations of Blood Ammonia Levels in Adult-Type Citrullinemia', 137 Tokohu J. Ex/ Med, 213-220 (1982).
Yu, Ryan and Potter, Murray, 'Diagnosis of Urea Cycle Disorders in Adulthood: Late-Onset Carbamyl Phosphate Synthetase 1 Deficiency', 7 MUMJ 30 (2010).
Yudkoff, M. et al., In Vivo Nitrogen Metabolism in Ornithine Transcarbamylase Deficiency, 98 J. Clin. Invest. 2167-2173 (1996).
Yurdaydin C., Blood ammonia determination in cirrhosis: Still confusing after all these years? Hepatology 38 (5) Nov. 2003, pp. 1307-1310.
Zeitlin, P., Novel Pharmacologic Therapies for Cystic Fibrosis, 103 J. Clinical Investigation 447 (1999).
Zeitlin, P.L. et al. (2002) 'Evidence of CFTR Function in Cystic Fibrosis After System Administration of 4-Phenylbutyrate,' Mol Therapy 6(1 ):119-126.
Zhao, et al., "Oxidation of Primary Alcohols to Carboxylic Acids with Sodium Chlorite Catalyzed by TEMPO and Bleach," J. Org. Chem., 1999, 64 (7), pp. 2564-2566.
Boulieu, R. et al., "Pharmacokinetics of Midazolam and its main metabolite 1-hydroxymidazolam in intensive care patients", Eur J Drug Metab Pharmacokinet., 23(2):255-8, (1998).
International Application No. PCT/US2017/034286; International Preliminary Report on Patentability, dated Nov. 27, 2018; 6 pages.
MedCalc: Body Surface Area Calculator, BSA of 21.65 Kg and 9832 cm is 0.769 m2 using the Mostellar method, 2 pages. (Year: 2010).
MedCalc: Body Surface Area Calculator, BSA of 41/9 Kg and 133.66 cm is 1.246 m2 using the Mostellar method, 2 pages. (Year: 2010).
MedCalc: Body Surface Area Calculator, BSA of 61.93 Kg and 169 cm is 1.705 m2 using the Mostellar method, 2 pages. (Year: 2010).
Peeters, M. et al., "Pharmacokinetics and Pharmacodynamics of Midazolam and Metabolites in Nonventilated Infants After Craniofacial Surgery", Anesthesiology, 105(6):1135-46, (2006).
The Doctors Company webpage; retreived Oct. 4, 2018 (Year: 2018); 2 pages.
U.S. Appl. No. 14/514,334; Non-Final Office Action, dated Mar. 5, 2019; 26 pages.
U.S. Appl. No. 15/316,049; Advisory Action dated Mar. 29, 2019; 3 pages.
U.S. Appl. No. 15/316,049; Final Office Action, dated Dec. 21, 2018; 12 pages.
U.S. Appl. No. 15/402,780; Final Office Action. dated Mar. 7, 2019; 38 pages.
U.S. Appl. No. 15/639,171,;Final Office Action, dated Oct. 16, 2018; 43 pages.
U.S. Appl. No. 15/639,171; Advisory Action, dated Nov. 29, 2018; 3 pages.
U.S. Appl. No. 15/639,171; Non-Final Office Action, dated Dec. 13, 2018; 20 pages.
U.S. Appl. No. 15/684,876; Advisory Action, dated Nov. 15, 2018; 3 pages.
U.S. Appl. No. 15/684,876; Non-Final Office Action. dated Mar. 7, 2019; 14 pages.
U.S. Appl. No. 15/687,141; Applicant-Initiated Interview summary, dated May 10, 2019; 2 pages.
U.S. Appl. No. 15/687,141; Non-Final Office Action, dated May 10, 2019; 19 pages.
U.S. Appl. No. 15/687,144; Final Office Action. dated Feb. 28, 2019; 20 pages.
U.S. Appl. No. 15/687,144; Pre-Interview First office action, dated Oct. 1, 2018; 8 pages.
U.S. Appl. No. 15/696,448; Final Office Action, dated Dec. 18, 2018; 40 pages.
U.S. Appl. No. 15/696,448; Notice of Allowance. dated Mar. 14, 2019; 5 pages.
U.S. Appl. No. 15/816,711; Final Office Action, dated Oct. 29, 2018; 43 pages.
U.S. Appl. No. 15/980,376; Notice of Allowability, dated Nov. 13, 2018; 6 pages.
U.S. Appl. No. 15/980,376; Notice of Allowance, dated Nov. 7, 2018; 14 pages.
U.S. Appl. No. 15/980,431; Final Office Action. dated Mar. 6, 2019; 29 pages.
VKM Report 2016:66 used as evidentiary reference (Year: 2016).
Bigot, A. et al., "Liver Involvement in Urea Cycle Disorders: A Review of the Literature", J Inherit Metab Dis., (Abstract only), 40(6):757-69, (2017).
U.S. Appl. No. 15/316,049; Non-Final Office Action, dated May 31, 2019; 9 pages.
U.S. Appl. No. 15/687,141; Final Office Action, dated Aug. 30, 2019; 11 pages.
U.S. Appl. No. 15/980,431; Non-Final Office Action, dated Oct. 2, 2019; 25 pages.
U.S. Appl. No. 16/194,061; Non-Final Office Action, dated Aug. 14, 2019; 32 pages.
U.S. Appl. No. 16/405,523; Application as filed, dated May 7, 2019; 12 pages.

\* cited by examiner

| PATIENT PRESENTATION | | CONTRIBUTORS OF MISDIAGNOSIS | DELAYED DIAGNOSIS |
|---|---|---|---|
| Symptomatic Early-Onset | Neonatal | Symptoms can mimic neonatal sepsis<br>• Ammonia is not part of routine sepsis laboratory workup, so providers may not check | Often presents when the newborn is home, resulting in a delayed diagnosis |
| Symptomatic Late-Onset | Acute or chronic presentations of UCDs can appear at any age | Subtle and nonspecific symptoms, including:<br>• Neurological: headaches, lethargy, confusion, and behavioral abnormalities<br>• Gastrointestinal: vomiting and loss of appetite | Diagnosis may be delayed for months or years after neurological damage begins |
| "Asymptomatic" | Damage from silent hyperammonemia is not always apparent and may be progressive | Subclinical symptoms may not be apparent to patients/HCPs and nonspecific symptoms may be misdiagnosed as psychiatric disorders or food poisoning | Typically remains undiagnosed unless a hyperammonemic crisis occurs or an immediate family member is diagnosed |

FIG. 5

TREATMENT OF UREA CYCLE DISORDERS IN NEONATES AND INFANTS

This application claims priority to U.S. Provisional Application No. 62/556,698, filed Sep. 11, 2017, and U.S. Provisional Application No. 62/628,252, filed Feb. 8, 2018, each of which is incorporated by reference in its entirety for all purposes.

BACKGROUND

Urea cycle disorders (UCD) are inborn errors of metabolism caused by a deficiency in one of six enzymes or two mitochondrial transport proteins involved in the production of urea, resulting in accumulation of toxic levels of ammonia in the blood (hyperammonemia). UCD subtypes include those caused by an X-linked mutation and corresponding deficiency in ornithine transcarbamylase (OTC) and those caused by autosomal recessive mutations with corresponding deficiencies in argininosuccinate synthetase (ASS), carbamyl phosphate synthetase (CPS), argininosuccinate lyase (ASL), arginase (ARG), N-acetylglutamate synthetase (NAGS), ornithine translocase (HHH), and aspartate glutamate transporter (CITRIN). These are rare diseases, with an overall estimated incidence in the United States of approximately 1 in every 35,000 live births. UCD is suspected when a subject experiences a hyperammonemic event with an ammonia level >100 µmol/L accompanied by signs and symptoms compatible with hyperammonemia in the absence of other obvious causes and generally confirmed by genetic testing.

The severity and timing of UCD presentation vary according to the severity of the deficiency, which may range from minor to extreme depending on the specific enzyme or transporter deficiency, and the specific mutation in the relevant gene. UCD patients may present in the early neonatal period with a catastrophic illness, or at any point in childhood, or even adulthood, after a precipitating event such as infection, trauma, surgery, pregnancy/delivery, or change in diet. Acute hyperammonemic episodes at any age carry the risk of encephalopathy and resulting neurologic damage, sometimes fatal, but even chronic, sub-critical hyperammonemia can result in impaired cognition. UCDs are therefore associated with a significant incidence of neurological abnormalities and intellectual and developmental disabilities over all ages. UCD patients with neonatal-onset disease are especially likely to suffer cognitive impairment and death compared with patients who present later in life.

Management of acute hyperammonemic crises may require hemodialysis and/or intravenous (IV) administration of sodium phenylacetate (NaPAA) and sodium benzoate (NaBz) (the admixture is marketed in the U.S. as AMMONUL®). Orthotopic liver transplantation may also be considered for patients with severe disease that manifests itself in the neonatal period. Long-term UCD management is directed toward prevention of hyperammonemia and includes restriction of dietary protein; arginine and citrulline supplementation, which can enhance waste nitrogen excretion for certain UCDs; and oral, ammonia-scavenging drug therapy that provides an alternate path for waste nitrogen removal (RAVICTI® (glycerol phenylbutyrate, GPB) Oral Liquid or sodium phenylbutyrate (NaPBA; marketed in the U.S. as BUPHENYL® and in the European Union (EU) as AMMONAPS®)).

RAVICTI®, formerly HPN-100, a prodrug of PBA and a pre-prodrug of the active compound phenylacetate (PAA), has been approved in the U.S. for use as a nitrogen-binding agent for chronic management of adult and pediatric patients ≥2 years of age with UCDs who cannot be managed by dietary protein restriction and/or amino acid supplementation alone. RAVICTI® is glycerol phenylbutyrate, a triglyceride containing 3 molecules of PBA linked to a glycerol backbone, the chemical name of which is benzenebutanoic acid, 1',1"-(1,2,3-propanetriyl) ester.

Glycerol phenylbutyrate is used with dietary protein restriction and, in some cases, dietary supplements (e.g., essential amino acids, arginine, citrulline, protein-free calorie supplements). RAVICTI® is not indicated for the treatment of acute hyperammonemia in patients with UCDs, and the safety and efficacy of RAVICTI® for the treatment of NAGS deficiency has not been established. The RAVICTI® Package Insert states the drug is contraindicated in patients less than 2 months of age, stating that children less than 2 months of age may have immature pancreatic exocrine function, which could impair hydrolysis of RAVICTI®, leading to impaired absorption of phenylbutyrate and hyperammonemia; and in patients with known hypersensitivity to phenylbutyrate (signs include wheezing, dyspnea, coughing, hypotension, flushing, nausea, and rash).

While the U.S. approval of RAVICTI® was based on its evaluation in 6 clinical trials involving over 100 adult and pediatric UCD patients aged 2 months old and above, only 7 patients aged 2 months to 2 years were enrolled in these studies. Among the 4 patients aged 2 months to 2 years who participated in an open label, fixed-sequence switch-over comparison of RAVICTI® to NaPBA, mean ammonia exposure assessed at 24-hour area under the curve was non-inferior on RAVICTI®. PAA exposure, also assessed as 24-hour area under the curve, was very similar. However, the number of patients in this age group studied at the time of RAVICTI's approval was small and considerable patient-to-patient variability was observed.

Children less than 2 months of age may have immature pancreatic exocrine function, which could impair hydrolysis of glycerol phenylbutyrate leading to impaired absorption of PBA and potentially hyperammonemia. While the limited data available suggest that pancreatic enzymes present in newborns include pancreatic lipase-related protein and bile salt-stimulated lipase (which digest triglycerides present in human breast milk), both of which hydrolyze glycerol phenylbutyrate in vitro, it is not known whether pancreatic function in newborns is sufficiently mature to digest glycerol phenylbutyrate. In addition, the metabolism of PAA is known to vary with body size, and given that body size changes dramatically during the first two years of life, there has been significant uncertainty how glycerol phenylbutyrate or NaPBA could be used in these patient populations from birth to two years of age.

Dosing of UCD patients less than 2 years of age is particularly difficult. In contrast to patients detected based on The Newborn Screen who may be mildly affected, patients less than 2 years of age presumably have little to no endogenous urea cycle activity. That is, patients less than 2 years of age presenting in crisis presumably have little or no 'innate' ability to convert ammonia to urea, such that they may be totally dependent on the drug to rid the body of waste nitrogen (including ammonia) via the alternate pathway. Thus there is little to no room for error since there is no endogenous capacity to buffer drug 'underdosing'. Patients less than 2 years of age are also particularly susceptible to overdosing because of their slower clearance of PAA.

There is a significant, unmet need for a nitrogen scavenging drug that can be used in UCD patients less than 2 years of age. Further, for the purposes of dose monitoring, frequent blood draws are difficult in neonates and children under two years of age and a non-invasive measure is needed. The present disclosure meets these needs.

SUMMARY

Provided is the use of glycerol phenylbutyrate as a nitrogen-binding agent for chronic management of pediatric patients with a UCD under 2 years in age.

Also provided is a method of treating a UCD in a patient under 2 years of age comprising administering glycerol phenylbutyrate to said patient at an initial daily dose which is administered at an initial frequency of administration; and if after said administration, said patient exhibits a urinary phenylacetylglutamine (PAGN) ≥9000 µg/mL and a ratio of plasma PAA to plasma PAGN of ≤2.5, then administering said glycerol phenylbutyrate to said patient at an increased daily dose while maintaining said initial frequency of administration. In some embodiments, the patient exhibits elevated blood ammonia levels. In some embodiments, the compliance and effectiveness of drug delivery by the patients' parent(s), guardian(s), or health care provider(s) is also assessed. In some embodiments, urinary PAGN concentration is measured using a filter paper-type test. In some embodiments, urinary PAGN concentration is measured from urine collected directly from a diaper or via the blood-spot technology commonly used for The Newborn Screen (NBS).

Also provided is a method of treating a UCD in a patient under 2 years of age comprising administering glycerol phenylbutyrate to said patient at an initial daily dose which is administered at an initial frequency of administration; and if after said administration, said patient exhibits a urinary PAGN ≥9000 µg/mL and a ratio of plasma PAA to plasma PAGN of >2.5, then administering said glycerol phenylbutyrate to said patient at a lower dose or an increased frequency of administration while maintaining said daily dose. In some embodiments, the patient exhibits elevated blood ammonia levels. In some embodiments, the compliance and effectiveness of drug delivery by the patients' parent(s), guardian(s), or health care provider(s) is also assessed. In some embodiments, urinary PAGN concentration is measured using a filter paper-type test. In some embodiments, urinary PAGN concentration is measured from urine collected directly from a diaper or via the blood-spot technology commonly used for the NBS.

Also provided is a method of treating a UCD in a patient under 2 years of age comprising administering glycerol phenylbutyrate to said patient at an initial daily dose which is administered at an initial frequency of administration; and if after said administration, said patient exhibits a ratio of plasma PAA to plasma PAGN of >2.5 or a level of plasma PAA of >500 µg/mL, then administering said glycerol phenylbutyrate to said patient at a reduced daily dose while maintaining said initial frequency of administration. In some embodiments, the patient exhibits neurological symptoms such as vomiting, headache, lethargy, and/or somnolence. In some embodiments, the patient exhibits normal blood ammonia levels. In some embodiments, the compliance and effectiveness of drug delivery by the patients' parent(s), guardian(s), or health care provider(s) is also assessed. In some embodiments, urinary PAGN concentration is measured using a filter paper-type test. In some embodiments, urinary PAGN concentration is measured from urine collected directly from a diaper or via the blood-spot technology commonly used for the NBS.

Also provided is a method of treating a UCD in a patient under 2 years of age comprising administering glycerol phenylbutyrate to said patient at an initial daily dose which is administered at an initial frequency of administration; and if after said administration, said patient exhibits a ratio of plasma PAA to plasma PAGN of >2.5 or a level of plasma PAA of >500 µg/mL, then administering said glycerol phenylbutyrate to said patient at a lower dose or an increased frequency of administration while maintaining said daily dose. In some embodiments, the patient exhibits neurological symptoms. In some embodiments, the patient exhibits normal blood ammonia levels. In some embodiments, the compliance and effectiveness of drug delivery by the patients' parent(s), guardian(s), or health care provider(s) is also assessed. In some embodiments, urinary PAGN concentration is measured using a filter paper-type test. In some embodiments, urinary PAGN concentration is measured from urine collected directly from a diaper or via the blood-spot technology commonly used for the NBS.

Also provided is a method of treating a UCD in a patient under 2 years of age comprising administering glycerol phenylbutyrate to said patient at an initial daily dose which is administered at an initial frequency of administration; and if after said administration said patient exhibits neurological symptoms, normal ammonia levels, and a ratio of plasma PAA to plasma PAGN of <2.5, then said glycerol phenylbutyrate to said patient should continue to be administered at the same dose and frequency and the patient evaluated for other causes of his or her neurological symptoms. In some embodiments, the patient exhibits neurological symptoms. In some embodiments, the patient exhibits normal blood ammonia levels. In some embodiments, the compliance and effectiveness of drug delivery by the patients' parent(s), guardian(s), or health care provider(s) is also assessed. In some embodiments, urinary PAGN concentration is measured using a filter paper-type test. In some embodiments, urinary PAGN concentration is measured from urine collected directly from a diaper or via the blood-spot technology commonly used for the NBS.

Also provided is a method of treating a UCD in a patient under 2 years of age comprising administering glycerol phenylbutyrate to said patient at an initial daily dose which is administered at an initial frequency of administration; and if after said administration, said patient exhibits elevated ammonia levels, a urinary PAGN <9000 µg/mL, a ratio of plasma PAA to plasma PAGN of ≤2.5, and compliance with initial daily dosing is confirmed, then administering said glycerol phenylbutyrate to said patient at an increased dose while maintaining frequency of administration. In some embodiments, the patient exhibits elevated blood ammonia levels. In some embodiments, the compliance and effectiveness of drug delivery by the patients' parent(s), guardian(s), or health care provider(s) is also assessed. In some embodiments, urinary PAGN concentration is measured using a filter paper-type test. In some embodiments, urinary PAGN concentration is measured from urine collected directly from a diaper or via the blood-spot technology commonly used for the NBS.

Also provided is a method of treating a UCD in a patient under 2 years of age comprising administering glycerol phenylbutyrate to said patient at an initial daily dose which is administered at an initial frequency of administration; and if after said administration, said patient exhibits elevated ammonia levels, a urinary PAGN <9000 µg/mL, and a ratio of plasma PAA to plasma PAGN of >2.5, then administering said glycerol phenylbutyrate to said patient at an increased dose frequency while maintaining the said daily dose. In some embodiments, the patient exhibits elevated blood ammonia levels. In some embodiments, the compliance and effectiveness of drug delivery by the patients' parent(s), guardian(s), or health care provider(s) is also assessed. In some embodiments, urinary PAGN concentration is measured using a filter paper-type test. In some embodiments, urinary PAGN concentration is measured from urine collected directly from a diaper or via the blood-spot technology commonly used for the NBS.

These and other embodiments of the disclosure are described in detail below.

BRIEF DESCRIPTION OF THE DRAWINGS

FIG. 5 shows a chart with UCD patient information relating to patient presentation and contributors of delayed- and mis-diagnosis.

DETAILED DESCRIPTION

Figure 1:
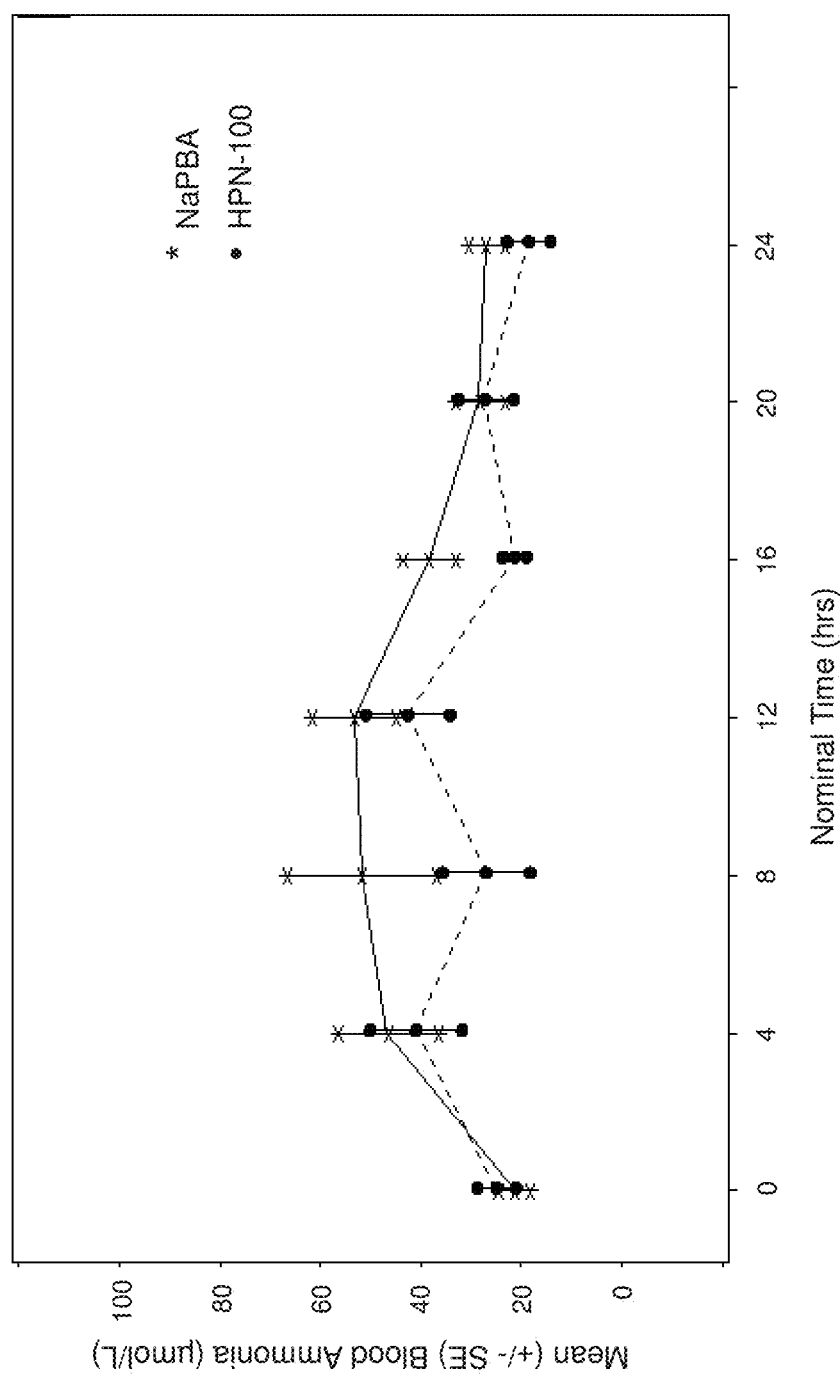
FIG. 1 shows mean±SE blood ammonia values for a 24-hour period following 7 days of treatment with NaPBA and HPN-100 in pediatric UCD subjects (N=11).

As used in this specification and the appended claims, the singular forms "a," "an" and "the" include plural referents unless the context clearly dictates otherwise. Thus, for example, "an active agent" refers not only to a single active agent but also to a combination of two or more different active agents, "a dosage form" refers to a combination of dosage forms as well as to a single dosage form, and the like.

Unless defined otherwise, all technical and scientific terms used herein have the meaning commonly understood by one of ordinary skill in the art to which the disclosure pertains. Specific terminology of particular importance to the description of the present disclosure is defined below.

The terms "treating" and "treatment" as used herein refer to reduction in severity and/or frequency of symptoms, elimination of symptoms and/or underlying cause, and improvement or remediation of damage. In certain aspects, the term "treating" and "treatment" as used herein refer to the prevention of the occurrence of symptoms. In other aspects, the term "treating" and "treatment" as used herein refer to the prevention of the underlying cause of symptoms associated with obesity, excess weight, and/or a related condition. The phrase "administering to a patient" refers to the process of introducing a composition or dosage form into the patient via an art-recognized means of introduction.

By the terms "effective amount" and "therapeutically effective amount" of an agent, compound, drug, composition or combination means that nontoxic and effective for producing some desired therapeutic effect upon administration to a subject or patient (e.g., a human subject or patient).

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, "subject" or "individual" or "patient" refers to any patient for whom or which therapy is desired, and generally refers to the recipient of the therapy.

With regards to "patients under 2 years of age", the International Conference on Harmonisation (ICH) categorizes the pediatric population as follows: newborn (birth to 1 month), infants/toddlers (1 month to <24 months), children (2 years to <12 years), and adolescents (12 years to <16 years).

As used herein, the term "normal ammonia levels" refers to a patient's blood plasma ammonia concentration less than 35 μmon. As used herein, the term "elevated ammonia levels" refers to refers to a patient's blood plasma ammonia concentration equal to or greater than 35 μmon. In some embodiments, the ULN is normalized to 35 μmon in blood plasma. To this effect, ULN can vary based on testing methodology (e.g., enzymatic versus colorimetric, μmol/L versus μg/mL) and from laboratory to laboratory. Two units, μmol/L and μg/dL, can be used for the ammonia data. The conversion formula is μg/dL×0.5872=μmol/L. Ammonia values from different labs can be normalized to 9-35 μmol/L.

Collection and measurement of a patient's blood plasma ammonia levels are known to those of skill in the art. Notably, fasting blood plasma ammonia levels demonstrate the least variability and offer a practical means for predicting the risk and frequency of an HA crisis. In some embodiments, the patient's blood plasma ammonia levels are assayed after fasting. In some embodiments, a patient's blood plasma ammonia level is assayed using venous blood samples. However, for the purposes of this disclosure, additional, standardized methods of blood plasma ammonia collection and measurement, such as by finger prick, may also be suitable.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range.

Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Provided is a method of treating a UCD in a patient under 2 years of age comprising administering glycerol phenylbutyrate to said patient at an initial daily dose which is administered at an initial frequency of administration; and if after said administration, said patient exhibits a urinary PAGN ≥9000 µg/mL and a ratio of plasma PAA to plasma PAGN of ≤2.5, then administering said glycerol phenylbutyrate to said patient at an increased daily dose while maintaining said initial frequency of administration.

Also provided is a method of treating a UCD in a patient under 2 years of age comprising administering glycerol phenylbutyrate to said patient at an initial daily dose which is administered at an initial frequency of administration; and if after said administration, said patient exhibits a urinary PAGN ≥9000 µg/mL and a ratio of plasma PAA to plasma PAGN of >2.5, then administering said glycerol phenylbutyrate to said patient at an increased frequency of administration while maintaining said daily dose.

Also provided is a method of treating a UCD in a patient under 2 years of age comprising administering glycerol phenylbutyrate to said patient at an initial daily dose which is administered at an initial frequency of administration; and if after said administration, said patient exhibits a ratio of plasma PAA to plasma PAGN of >2.5 or a level of plasma PAA of >500 µg/mL, then administering said glycerol phenylbutyrate to said patient at a reduced daily dose while maintaining said initial frequency of administration.

Also provided is a method of treating a UCD in a patient under 2 years of age comprising administering glycerol phenylbutyrate to said patient at an initial daily dose which is administered at an initial frequency of administration; and if after said administration, said patient exhibits a ratio of plasma PAA to plasma PAGN of >2.5 or a level of plasma PAA of >500 µg/mL, then administering said glycerol phenylbutyrate to said patient at a lower dose or an increased frequency of administration while maintaining said daily dose.

Also provided is a method of treating a UCD in a patient under 2 years of age comprising administering glycerol phenylbutyrate to said patient at an initial daily dose which is administered at an initial frequency of administration; and if after said administration said patient exhibits neurological symptoms, normal ammonia levels, and a ratio of plasma PAA to plasma PAGN of <2.5, then said glycerol phenylbutyrate to said patient should continue to be administered at the same dose and frequency and the patient evaluated for other causes of his or her neurological symptoms.

Also provided is a method of treating a UCD in a patient under 2 years of age comprising administering glycerol phenylbutyrate to said patient at an initial daily dose which is administered at an initial frequency of administration; and if after said administration, said patient exhibits elevated ammonia levels, a urinary PAGN <9000 µg/mL, a ratio of plasma PAA to plasma PAGN of ≤2.5, and compliance with initial daily dosing is confirmed, then administering said glycerol phenylbutyrate to said patient at an increased dose while maintaining frequency of administration.

Also provided is a method of treating a UCD in a patient under 2 years of age comprising administering glycerol phenylbutyrate to said patient at an initial daily dose which is administered at an initial frequency of administration; and if after said administration, said patient exhibits elevated ammonia levels, a urinary PAGN <9000 µg/mL, and a ratio of plasma PAA to plasma PAGN of >2.5, then administering said glycerol phenylbutyrate to said patient at an increased dose frequency while maintaining the said daily dose.

The methods disclosed herein presume that the patient is effectively receiving all of the prescribed dose. Some parents have difficult delivering a liquid drug to newborns and, therefore, in some embodiments, the compliance and effectiveness of drug delivery by the patients' parent(s), guardian(s), or health care provider(s) can also be assessed.

In some embodiments, neurological symptoms include headache, confusion, vomiting, lethargy, or any combination thereof.

In some embodiments, the UCD is any subtype. In some embodiments, the UCD is not N-acetyl glutamate synthetase deficiency.

In some embodiments, the patient is a newborn, i.e., from birth to one month of age. In some embodiments, the patient is an infant/toddler, i.e., from 1 month to two years of age.

In some embodiments, the patient is treated for at least one month. In some embodiments, the patient is treated for at least six months. In some embodiments, the patient is treated for up to 24 months. In some embodiments, the patient is treated for more than 24 months. In some embodiments, the patient is treated for the rest of the patient's life. In some embodiments, the patient treated with the glycerol phenylbutyrate on a relatively continuous daily basis for at least 6 months or longer. In some embodiments, the patient receives a liver transplant and the treatment is terminated.

In some embodiments, the glycerol phenylbutyrate is administered orally. In some embodiments, the glycerol phenylbutyrate is administered via oral syringe. In some embodiments, the glycerol phenylbutyrate is administered via a gastric or nasogastric tube.

In some embodiments, the glycerol phenylbutyrate is administered just prior to breastfeeding or intake of formula or food.

In some embodiments, the patient is not being treated with carglumic acid.

In some embodiments, the patient is in a hyperammonemic crisis and the initial daily dose is 11.2 mL/m$^2$/day. In some embodiments, the patient is not in a hyperammonemic crisis and said initial daily dose is 8.5 mL/m$^2$/day.

In some embodiments, the patient previously had been administered NaPBA or NaBz and said initial daily dose is equal to 0.81 times the total number of grams of NaPBA powder the patient was receiving, or 0.86 times the total number of grams of in NaPBA tablet form the patient was receiving, or 0.5 times the total number of grams of in NaBz the patient was receiving.

In some embodiments, the initial frequency of administration is 3 to 6 times daily.

In some embodiments, if the initial frequency of administration is 3 times a day, then the increased frequency of administration is 4, 5, or 6 times a day. In some embodiments, if the initial frequency of administration is 3 times a day, then the increased frequency of administration is 4 times a day. In some embodiments, if the initial frequency of administration is 3 times a day, then the increased frequency of administration is 5 times a day. In some embodiments, if the initial frequency of administration is 3 times a day, then the increased frequency of administration is 6 times a day.

In some embodiments, if the initial frequency of administration is 4 times a day, then the increased frequency of administration is 5 or 6 times a day. In some embodiments, if the initial frequency of administration is 4 times a day, then the increased frequency of administration is 5 times a day. In some embodiments, if the initial frequency of administration is 4 times a day, then the increased frequency of administration is 6 times a day.

In some embodiments, if the initial frequency of administration is 5 times a day, then the increased frequency of administration is 6 times a day.

In some embodiments, the patient is less than about one month of age.

In some embodiments, the patient is from 1 month to two years of age.

Figure 3:
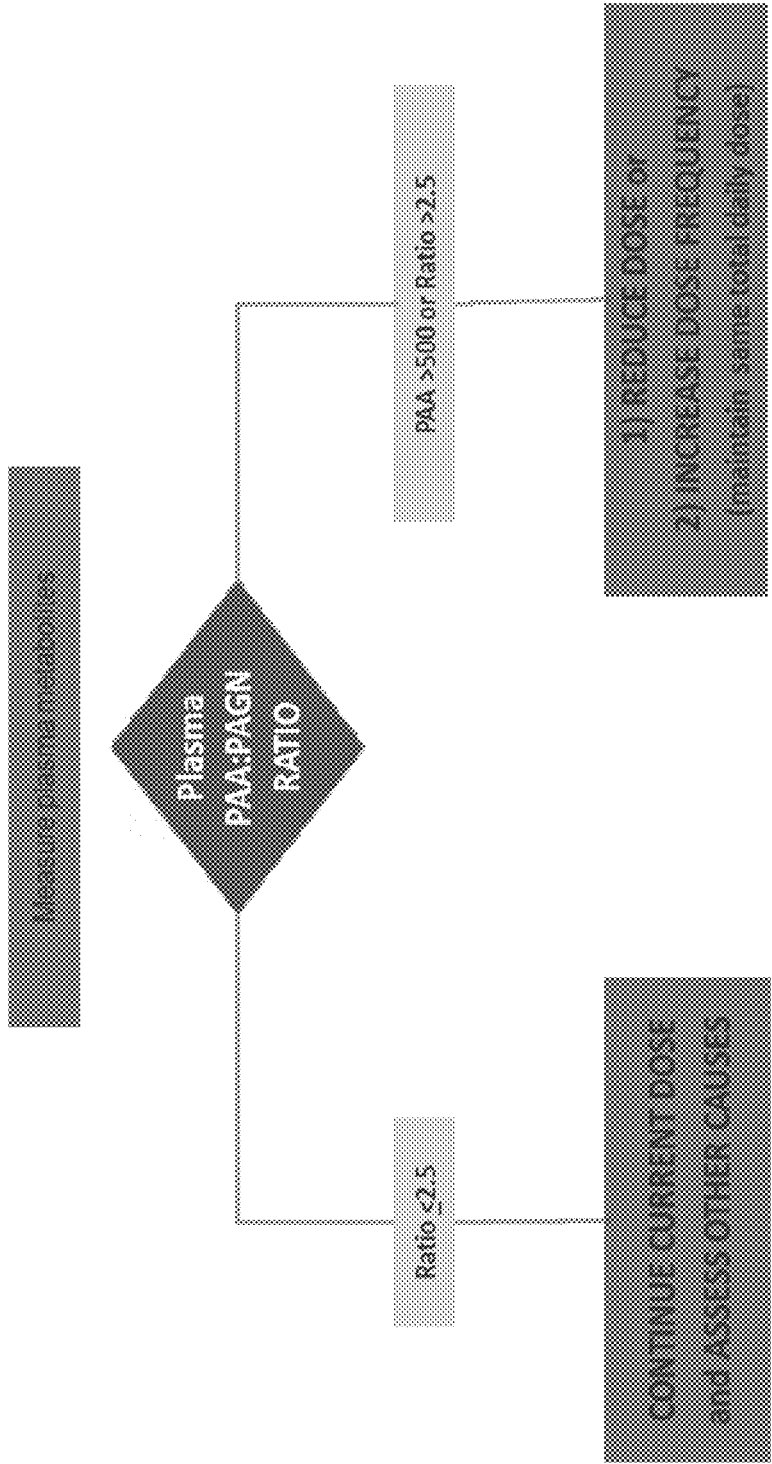
FIG. 3 shows a flow chart for dosing based on PAA:PAGN ratio in infants and toddlers presenting with neurological symptoms and normal ammonia levels.
Figure 4:
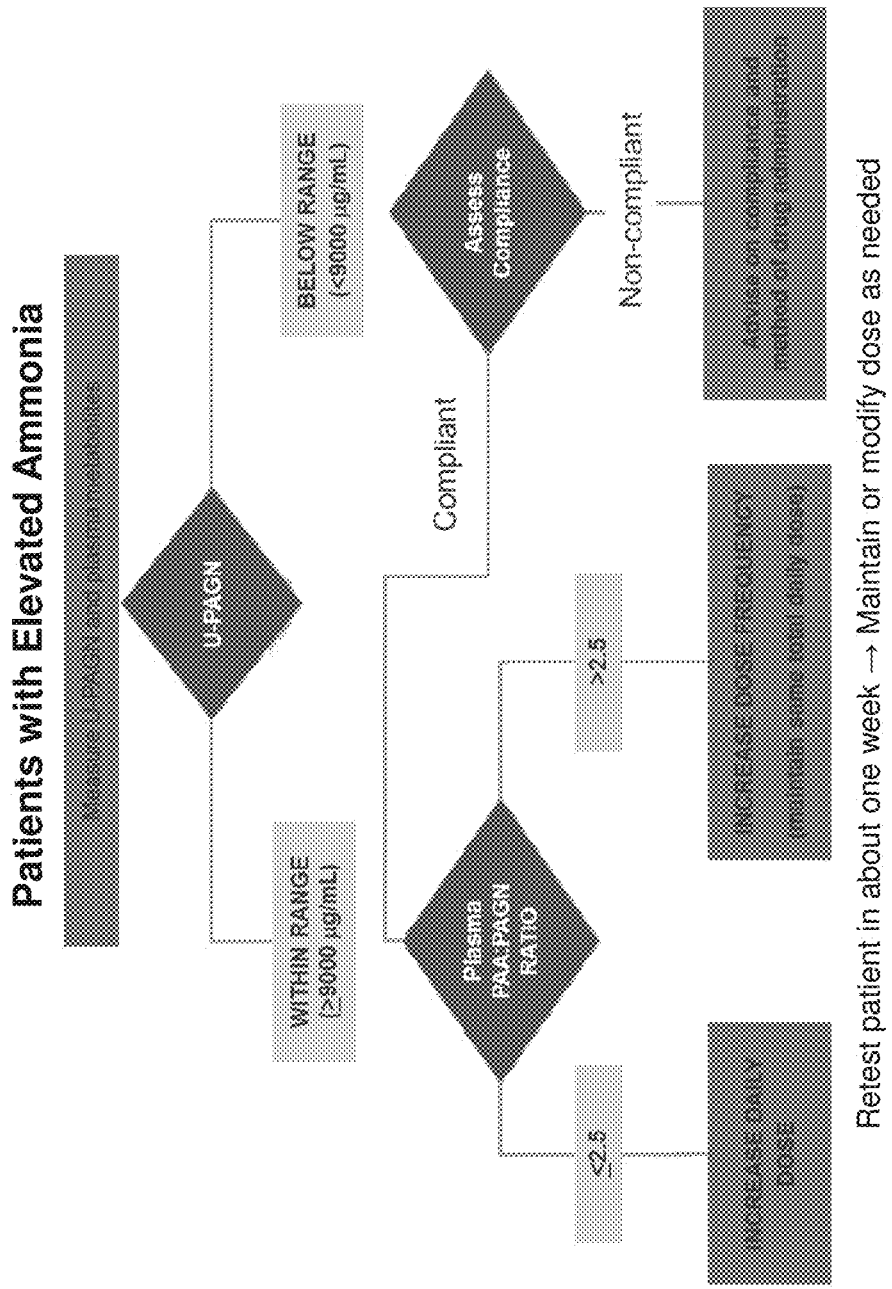
FIG. 4 shows a flow chart for dosing based on U-PAGN ratio and plasma PAA:PAGN ratio in infants and toddlers with elevated ammonia.
Figure 6:
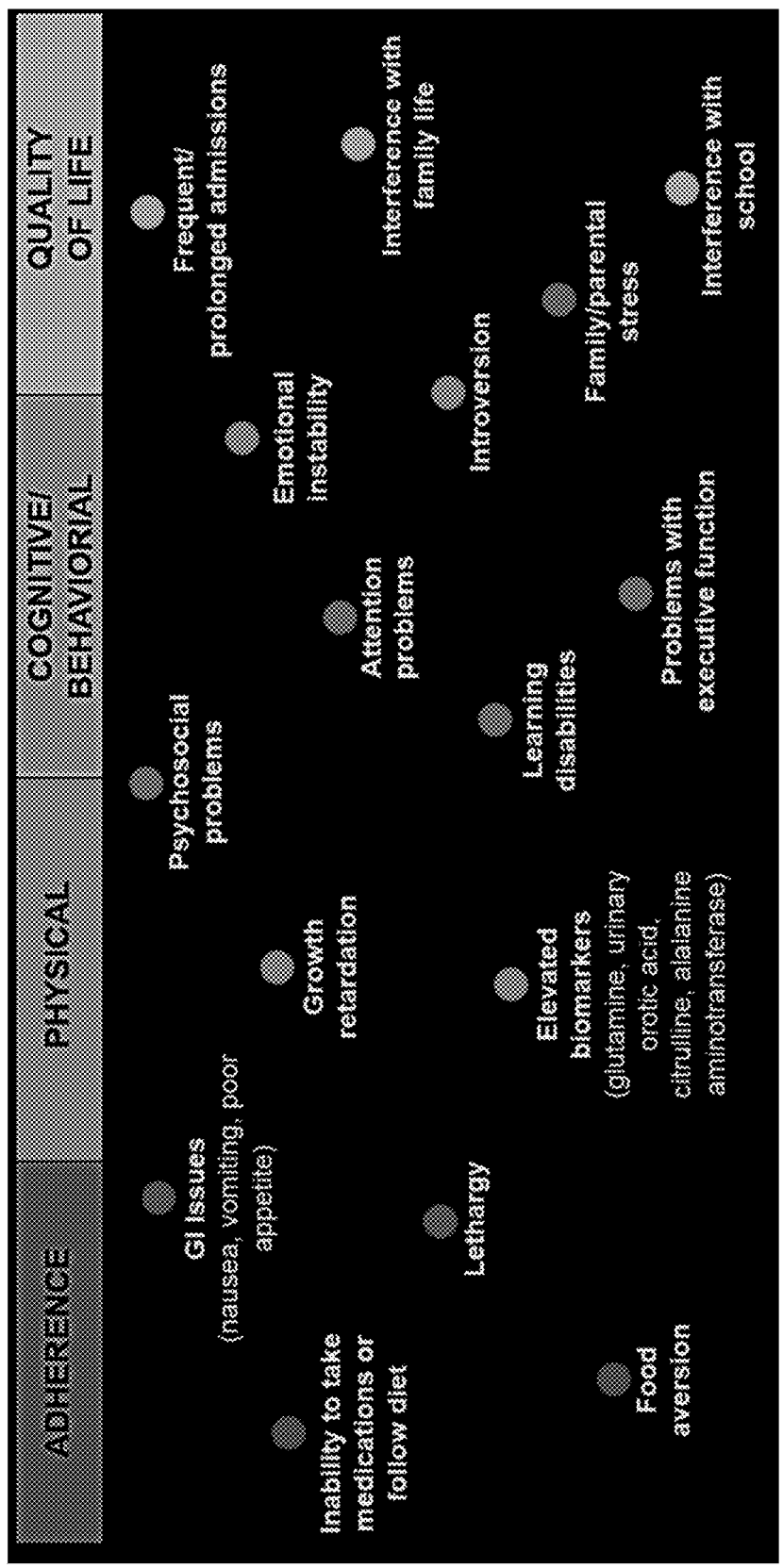
FIG. 6 shows a chart with the spectrum of UCD signs and symptoms beyond hyperammonemic (HA) crises.
Figure 7:
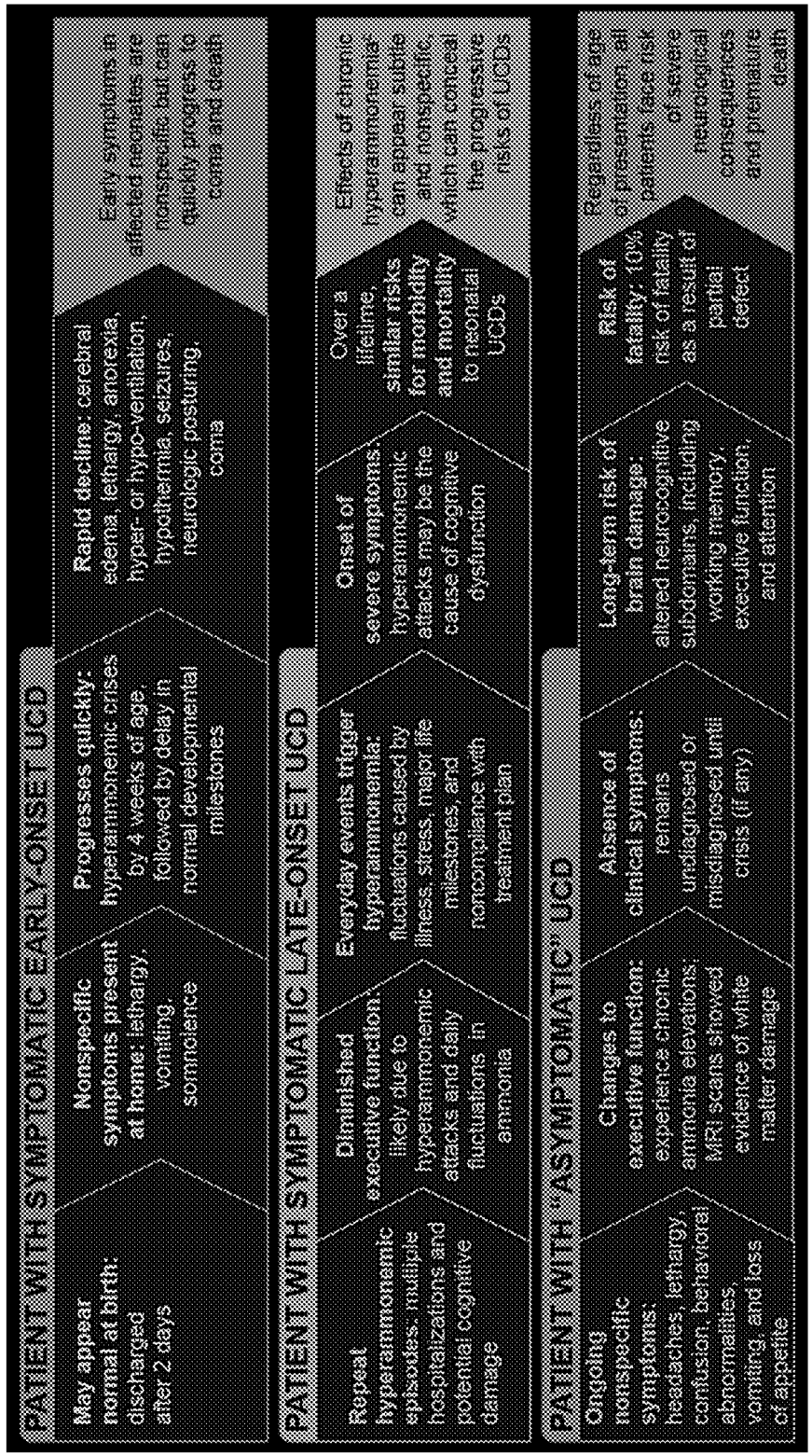
FIG. 7 shows a chart with UCD patient symptom and disease progression information.

In some embodiments, patient compliance with dosing is checked if U-PAGN is less than 9000 μg/mL and the patient experiences hyperammonemia. See FIGS. 3 and 4.

In some embodiments, the glycerol phenylbutyrate is provided as RAVICTI® product.

In some embodiments, the method further comprises restricting dietary protein, including amino acids and protein formula/supplements. The diet prescribed for each individual depends on developmental needs, age and residual enzyme activity.

In some embodiments, the method further comprises sampling the patient's urine and/or plasma.

In some embodiments, the method further comprises determining the effectiveness of intestinal hydrolysis of the glycerol phenylbutyrate.

In some embodiments, the method further comprises determining the rate at which the patient converts PBA to urinary PAGN.

In some embodiments, the method further comprises determining the efficiency of conjugation of PAA and glutamine.

In some embodiments, the daily dose or frequency of administration is selected and/or adjusted based at least in part on plasma ammonia level, ratio of PAA:PAGN and/or U-PAGN level.

A morning ammonia level less than half the upper limit of normal (the upper limit of normal (ULN) is 35 μmon in blood plasma) increases the likelihood that the average daily ammonia will be within normal limits and is associated with a decreased risk and frequency of hyperammonemic crises. In some embodiments, satisfactory ammonia control is defined as: no signs and symptoms of hyperammonemia and blood plasma ammonia values <100 μmon. In some embodiments, patient dosing is maintained at an initial dose so long as the patient's blood plasma ammonia level is less than half the ULN (i.e., 35 μmol/L). In some embodiments, the ULN is normalized to 35 μmon in blood plasma. To this effect, ULN can vary based on testing methodology and from laboratory to laboratory.

In some embodiments, the samples are collected prior to the first dose of the day.

In some embodiments, the duration of ammonia monitoring will vary depending on the patient's age and their presenting conditions, as shown below. Patients less than 2 months of age will in some embodiments have ammonia levels monitored for a total of 72 hours (including 48 hours after the first full dose of glycerol phenylbutyrate) prior to the physician making the judgment that the patient has recovered (no signs and symptoms of hyperammonemia and ammonia <100 μmon); patients aged 2 months and older following a hyperammonemic crisis will in some embodiments have ammonia levels monitored for a total of 48 hours (including 24 hours after their first full dose of glycerol phenylbutyrate); and patients aged 2 months and older who are newly diagnosed and stable or are already stable on NaPBA or NaBz will initiate or transition to glycerol phenylbutyrate and have their ammonia levels monitored in some embodiments for 24 hours. A monitoring period of 48-72 hours, depending on the age of the patient, may in some embodiments involve evaluations of ammonia levels at a minimum of every 12 hours.

TABLE 1

Determination of duration for ammonia monitoring period.

| Age of Patient | HA Crisis | Ammonia Monitoring Period |
| --- | --- | --- |
| <2 months | Yes | 72 hours |
|  | No* | 72 hours |
| ≥2 months | Yes | 48 hours |
|  | No* | 24 hours |

*Stable Patient: defined as patients not in HA crisis who are diagnosed through newborn screening or patients currently on NaPBA or NaBz.

Population pharmacokinetic (PK) modeling and dosing simulations have demonstrated that body surface area is a determinant of the rate at which patients convert PAA to PAGN for both NaPBA and RAVICTI®. Very young patients are more likely than older patients to experience elevated PAA levels (i.e., in the range associated with generally reversible adverse events among cancer patients receiving PAA intravenously (nausea, vomiting, sweating, headache)). Measuring the plasma ratio of PAA to PAGN (the ratio of precursor to product, both in μg/mL) is clinically useful in that it represents an inherent measure of the efficiency with which PAA is converted to PAGN in an individual patient. A PAA:PAGN concentration ratio ≤2.5 indicates efficient conversion of PAA to PAGN and suggests that the dose of NaPBA or GPB phenylbutyrate could be increased, if necessary.

Among all populations and doses studied, a ratio greater than 2.5, when both PAA and PAGN are expressed in μg/mL, is associated with probabilities of PAA levels exceeding 400 μg/mL ranging from approximately 25% to 36%, whereas a ratio less than or equal to 2.5 is associated with an approximately 1% risk of a PAA value >400 μg/mL. Thus, a PAA to PAGN ratio >2.5 in a patient with unexplained neurological symptoms and normal ammonia provides guidance that cautious changes to dose or dosing regimen should be considered while maintaining the same daily dose. Neurological symptoms commonly associated with UCD are known to those of skill in the art and can include somnolence, headaches, lethargy, and confusion. Gastrointestinal symptoms commonly associated with UCD are also known to those of skill in the art and can include vomiting and loss of appetite.

U-PAGN measurements are used to help guide RAVICTI® dosing. Each gram of U-PAGN excreted over 24 hours covers waste nitrogen generated from 1.4 grams of dietary protein. Urinary PAGN has been shown to correlate directly and strongly with the dose of PBA administered, either as RAVICTI® or NaPBA, and the conversion of PBA to U-PAGN is generally between 60-75%. In young pediatric patients, even where complete urine collection is not possible, use of U-PAGN concentration is useful as a marker of compliance/effective drug delivery. Based on analysis of data obtained from all patients in RAVICTI® clinical trials and using the lower 25 percentile as a cutoff, the patient's caretaker should assess compliance and/or effectiveness of drug administration if the U-PAGN is <9000 µg/mL for patients under 2 years of age who exhibit unexplained hyperammonemia during treatment with glycerol phenylbutyrate.

In some embodiments, the patient's desired growth and development and/or body surface area (BSA) is also considered. For example, if the patient's weight/BSA, metabolic needs and/or dietary protein intake have increased, the RAVICTI® dose may be increased accordingly; each additional gram of daily protein can be covered by 0.6 mL/day of additional RAVICTI®.

Because plasma/urine PK results may not be available for real-time dose adjustment decisions, i.e. until after the patient's visit for sampling to be done, the present methods can also be practiced so as to guide dosing by providing a way to evaluate retrospectively dose adjustments already made based on ammonia levels and determine whether further adjustment is appropriate and what it should be, if so. Generally, samples for measurements of PAA and PAGN (plasma) and PAGN (urine) are collected at the time of each dose adjustment (in the retrospective mode; alternatively, samples can be taken and evaluated, and the dose adjustment, if any, implemented after the evaluation results are considered and used to guide dose adjustment, as provided herein).

EXAMPLES

Examples of embodiments of the present disclosure are provided in the following examples. The following examples are presented only by way of illustration and to assist one of ordinary skill in using the disclosure. The examples are not intended in any way to otherwise limit the scope of the disclosure.

Example 1

HPN-100-012 was an open-label, fixed sequence, switch-over study of the safety, PK and efficacy of HPN-100 compared to NaPBA in patients with UCDs, with a 12-month safety extension part. The switch-over part of the study and the 12-month safety extension are complete. The switch-over part was conducted at 7 U.S. centers and enrolled 15 pediatric UCD patients between 29 days and <6 year of age, all of whom completed the study. After review of all the safety data by the DSMB, 8 additional subjects were enrolled in the study after the switch-over phase was completed. The primary efficacy endpoint was the 24-hour AUC (area under the curve) for blood ammonia on Day 1 compared with Day 10. Results of this analysis demonstrated that HPN-100 was effective and non-inferior to NaPBA in controlling blood ammonia in pediatric patients with UCDs aged 29 days to <6 years (upper 90% CI of 1.002 and 95% CI of 1.055 based on the original scale, both well below the predefined non-inferiority upper margin of 1.25). The mean ammonia AUC was lower on HPN-100 than on NaPBA (median difference between treatments of −37.84 µmol/L*h); the corresponding p-value was 0.075 using the paired t-test and 0.033 using the nonparametric Wilcoxon rank-sum test.

Figure 2:
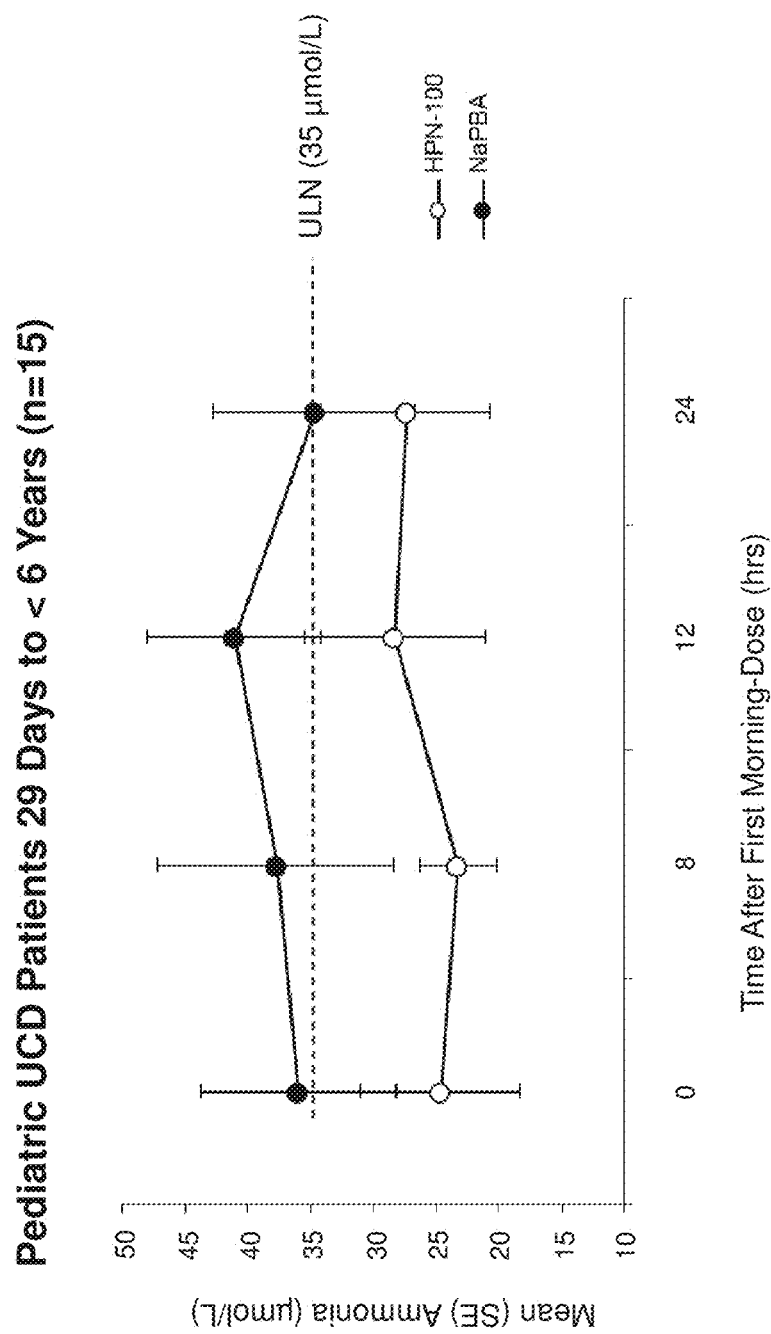
FIG. 2 shows mean blood ammonia over 24-h after treatment with NaPBA or HPN-100 (ITT Population). HPN-100=glycerol phenylbutyrate; ITT=intent-to-treat; NaPBA=sodium phenylbutyrate; SE=standard error; UCD=urea cycle disorder; ULN=upper limit of normal.

Mean blood ammonia levels following an overnight fast were normal at pre-dose and 24 hours post dose after treatment with NaPBA and HPN-100. See FIG. 2. At any given time point postprandially, blood ammonia levels were directionally lower during treatment with HPN-100 (Day 10) than with NaPBA (Day 1). Mean blood ammonia values were highest for both treatments at the 12-hour time point (28.24 µmol/L on HPN-100 and 41.03 µmol/L on NaPBA) and were lowest for HPN-100 treatment at the 8-h time point (23.20 µmol/L) and 24-hour time point on NaPBA (34.66 µmol/L).

Pooled ammonia analyses from short term studies were also conducted. In the pooled analyses, 24 hour ammonia was significantly lower on HPN-100 vs. NaPBA (mean [SD] $AUC_{0-24}$: 627 [302] vs. 872 [516] µmon; p=0.008) with significantly fewer abnormal values (15% on GPB vs. 35% on NaPBA; p=0.02).

The pharmacokinetics of the short term studies can be summarized as follows. Mean exposure levels of HPN-100 metabolites PBA, PAA, and PAGN after doses of HPN-100 and NaPBA with meals (TID) in pediatric (29 days to 17 years of age) UCD patients in HPN-100-005 and HPN-100-012 studies are summarized below. The mean exposure to PBA, the parent metabolite, and mean exposure to PAGN, the terminal metabolite, show no systematic variation across age groups, while PAA exposure tended to decrease with increasing age, a finding consistent with those from population PK modeling which indicate that the rate of clearance/metabolism of PAA varies directly with body size. While systemic metabolite exposure, assessed as peak plasma concentration ($C_{max}$) or AUC, is generally similar for HPN-100 and NaPBA, the minimum concentration ($C_{min-ss}$) was higher—and/or percent-fluctuation less—for plasma PAGN, a finding consistent with slower gastrointestinal absorption of PBA when administered orally as HPN-100.

TABLE 2

Pharmacokinetics of HPN-100 and NaPBA in pediatric patients with UCDs.

| | Pediatric UCD Patients (29 days-17 years) | | | |
|---|---|---|---|---|
| | HPN-100-005 (N = 11) | | HPN-100-012 (N = 15) | |
| PK Variable[a] | HPN-100 | NaPBA | HPN-100 | NaPBA |
| Mean (SD) Dose | 11.04 (3.859) | 10.94 (3.873) | 5.16 (2.316) | 5.27 (2.453) |
| Plasma PBA | | | | |
| $AUC_{0-24}$ (µg · h/mL) | 631 (44.9) | 236 (105.2) | 255 (54.5) | 483 (146.0) |
| $C_{max-ss}$ (µg/mL) | 95.6 (42.0) | 37.4 (101.6) | 36.8 (59.0) | 60.4 (128.3) |

TABLE 2-continued

Pharmacokinetics of HPN-100 and NaPBA in pediatric patients with UCDs.

Pediatric UCD Patients (29 days-17 years)

| PK Variable[a] | HPN-100-005 (N = 11) | | HPN-100-012 (N = 15) | |
|---|---|---|---|---|
| | HPN-100 | NaPBA | HPN-100 | NaPBA |
| $C_{min-ss}$ (µg/mL) | 1.50 (99.8) | 0.37 (171.3) | 0.750 (192.7) | 0.993 (227.3) |
| $T_{max-ss}$ (h)[b] | 12.00 | 12.00 | 8.00 | 8.30 |
| | (3.82, 15.90) | (8.00, 13.58) | (0.00, 12.00) | (7.33-12.17) |
| CLss/F (mL/min) | 20545 (47.2) | 145463 (123.4) | 22610 (48.6) | 112093 (136.4) |
| % Fluctuation | 5690 (56.8) | 1979 (123.7) | 1781 (84.6) | 5102 (75.9) |
| Plasma PAA | | | | |
| $AUC_{0-24}$ (µg·h/mL) | 964 (63.6) | 773 (73.3) | 1096 (214.0) | 1458 (211.3) |
| $C_{max-ss}$ (µg/mL) | 90.5 (69.1) | 75.1 (64.4) | 84.7 (148.3) | 98.0 (152.1) |
| $C_{min-ss}$ (µg/mL) | 2.99 (122.1) | 0.674 (130.5) | 26.1 (360.8) | 49.2 (287.2) |
| $T_{max-ss}$ (h) | 11.92 | 12.00 | 8.00 | 8.00 |
| | (7.75, 23.83) | (8.00, 12.02) | (7.42, 12.00) | (6.50-12.17) |
| CLss/F (mL/min) | 15082 (101.4) | 34391 (162.5) | 25538 (116.8) | 94249 (243.7) |
| % Fluctuation | 3483 (51.5) | 3931 (85.1) | 2141 (145.0) | 1289 (102.8) |
| Plasma PAGN | | | | |
| $AUC_{0-24}$ (µg·h/mL) | 1378 (40.2) | 1015 (44.7) | 1131 (71.2) | 946 (75.5) |
| $C_{max-ss}$ (µg/mL) | 105 (33.5) | 74.8 (37.3) | 85.5 (53.7) | 74.4 (61.3) |
| $C_{min-ss}$ (µg/mL) | 13.1 (64.9) | 4.6 (66.4) | 19.9 (173.4) | 17.7 (159.6) |
| $T_{max-ss}$ (h) | 12.00 | 12.00 | 7.92 | 8.00 |
| | (7.75, 23.83) | (7.73, 12.25) | (0.00, 12.00) | (0.00-12.17) |
| CLss/F (mL/min) | 14237 (36.8) | 19739 (44.3) | 10830 (85.6) | 14360 (93.0) |
| % Fluctuation | 1001 (84.5) | 1917 (54.8) | 907 (116.7) | 1459 (74.1) |
| U-PAGN | | | | |
| Ae (µg) | 12501037 (56.9) | 12512426 (51.3) | NA[c] | NA[c] |
| $Ae_{0-12}$ (µg) | 5611719 (74.7) | 7098020 (47.5) | NA[c] | NA[c] |
| $Ae_{12-24}$ (µg) | 6889318 (50.1) | 5414406 (71.9) | NA[c] | NA[c] |
| Fe % dose | 66.4 (23.9) | 69.0 (23.9) | NA[c] | NA[c] |
| $Fe_{0-12}$ (%) | 28.9 (42.1) | 39.6 (30.0) | NA[c] | NA[c] |
| $Fe_{12-24}$ (%) | 37.4 (32.3) | 29.3 (52.8) | NA[c] | NA[c] |

[a]Unless otherwise noted, data shown are arithmetic mean (coefficient of variation %).
[b]Median (minimum, maximum).
[c]Timed urine collections were not feasible among children under 6 participating in protocol HPN-100-012 and therefore recovery of PBA as urinary PAGN could not be calculated. Concentration of PAGN or the PAGN/creatinine ratio was measured/calculated from urine samples, and the results are summarized above.

Example 2

HPN-100-009 is an open-label study consisting of a transition period to HPN-100, followed by a safety extension period for at least 6 months and up to 24 months of treatment with HPN-100, depending on age at enrollment. It is designed to capture information important for evaluating safety, pharmacokinetics and efficacy in young children. Subjects eligible for this study included patients ranging from newborn to <2 years of age with either a diagnosed or clinically suspected UCD. Ten infant and toddler (28 days to 23 months) subjects were enrolled in this study.

Subjects aged 2 months to <2 years received RAVICTI® Oral Liquid administered just prior to breastfeeding or intake of formula or food. The recommended dosing regimen is 3-6 times per day depending on feeding schedule and at the discretion of the Investigator. The starting dose of RAVICTI® was based on UCD status (newly diagnosed, or already stable on sodium phenylbutyrate [NaPBA] and/or sodium benzoate [NaBz]) and whether a hyperammonemic crisis is present. Subsequently, the dose was adjusted based on clinical and/or ammonia results, according to an algorithm provided in the protocol.

TABLE 3

Study subjects. RAVICTI ®: Age 2 Months to <2 Years.

| Group Value | Number |
|---|---|
| Started | 10[a] |
| Completed | 1 |
| Not Completed: | 9 |
| Stopping Rule: Liver Transplant | 2 |
| Adverse Event, Non-Fatal | 1 |
| Ongoing in Study | 6 |
| Age (months)[b] | 9.9 (±5.53) |
| Female | 5 |
| Male | 5 |

[a]Overall in study = 10.
[b]Arithmetic mean (standard deviation).

Percentage of Subjects with Successful Transition to RAVICTI® with Controlled Ammonia (i.e. No Clinical Symptoms and Ammonia <100 µMol/L).

End point description. The percentage of subjects with successful transition was based on Investigator response to the question, "Has transition to 100% RAVICTI® been successful with controlled ammonia?" For subjects 2 months of age and older, after a minimum of 24 hours of ammonia monitoring following the first full dose of RAVICTI® alone, the subject was effectively transitioned when following conditions were met: no signs and symptoms of hyperammonemia; ammonia level less than 100 µmol/L (without normalization of ammonia, i.e., without conversion of values from local laboratories with varying normal ranges to standardized values); and eligible for discharge per Investigator judgment. Safety population: all enrolled subjects who received any amount of study medication. End point timeframe: up to Day 4.

Rate of Hyperammonemic Crises (HACs) During the First 6 Months on RAVICTI®.

End point description. A HAC was defined having signs and symptoms consistent with hyperammonemia (such as but not limited to frequent vomiting, nausea, headache, lethargy, irritability, combativeness, somnolence) associated with high blood ammonia and requiring medical intervention. Rate of HACs prior to enrollment was calculated as sum of (number of HAC)/sum of (subject age in days at the time of enrollment or 365 days, whichever was less) across all subjects in the corresponding group. Rate of HACs per 6 months during the safety extension was calculated as sum of (number of HAC)/sum of (days during first 6 months starting on Day 8 or number days on RAVICTI®, whichever was less) across all subjects in the corresponding group. Safety population: all enrolled subjects who received any amount of study medication. End point timeframe: up to 365 days prior to enrollment, Days 1-7, Day 8 up to Month 6.

TABLE 4

Rate of HACs. RAVICTI ®: Age 2 Months to <2 Years.

| End Point Value | Number |
|---|---|
| Subjects Analyzed | 10[a] |
| Rate Ratio | |
| HACs Prior to Enrollment (n = 10) | 0.11 |
| HACs During Transition (Days 1-7) (n = 10) | 0 |
| HACs During Safety Extension (n = 9) | 0.006 |

[a]Subjects with an assessment at given time point.

Number of Subjects with Treatment-Emergent Adverse Events (TEAEs), Serious TEAEs, Deaths, and Discontinuations Due to TEAEs.

End point description. An adverse event (AE) was any untoward medical occurrence, whether or not the event is considered related to the study drug. A serious AE was any AE that: results in death; was life threatening; requires hospitalization or prolongation of existing hospitalization; resulted in disability/incapacity; was a congenital anomaly/birth defect; was an important medical event. TEAEs were defined as AEs with an onset date on or after the first dose of study medication until study discontinuation. The Investigator assessed the causal relationship of each TEAE to the study drug as not related, possibly related, or probably related. Safety population: all enrolled subjects who received any amount of study medication. End point timeframe: up to 370 days.

TABLE 5

Subjects with TEAEs. RAVICTI ®: Age 2 Months to <2 Years.

| End Point Value | Number |
|---|---|
| Subjects Analyzed | 10 |
| Subjects | |
| ≥1 TEAE | 10 |
| ≥1 Related TEAE | 4 |
| ≥1 Serious TEAE | 6 |
| ≥1 Serious Related TEAE | 0 |
| Fatal Outcome TEAE | 1 |
| ≥1 TEAE Leading to Study Discontinuation | 1 |

Amino Acid Assessment: Baseline and Change from Baseline in Glutamate, Glutamine, and Sum of Glutamate and Glutamine Up to Month 9.

End point description. Safety population: all enrolled subjects who received any amount of study medication and had an assessment. End point timeframe: Baseline, Day 7, Month 2, Month 3, Month 4, Month 5, Month 6, Month 9.

TABLE 6

Amino acid assessment. RAVICTI ®: Age 2 Months to <2 Years.

| End Point Value | Glutamate ($\mu$mol/L)[b] | Glutamine ($\mu$mol/L)[b] | Sum ($\mu$mol/L)[b] |
|---|---|---|---|
| Subjects Analyzed | 7[a] | 7[a] | 7[a] |
| Baseline (n = 7) | 122.4 (±118.62) | 750.4 (±309) | 872.9 (±381) |
| Change from Baseline at Day 7 (n = 6) | −54.5 (±92.63) | −184.3 (±168.66) | −238.8 (±203.57) |
| Change from Baseline at Month 2 (n = 5) | 7.8 (±25.65) | −174.6 (±318.25) | −166.8 (±332.42) |
| Change from Baseline at Month 3 (n = 2) | 2 (±32.53) | −134.5 (±136.47) | −132.5 (±169) |
| Change from Baseline at Month 4 (n = 3) | −32.7 (±5.51) | −292 (±384.81) | −324.7 (±389.32) |
| Change from Baseline at Month 5 (n = 1) | −10 (±n/a)[c] | −240 (±n/a)[c] | −250 (±n/a)[c] |
| Change from Baseline at Month 6 (n = 3) | −3.3 (±48.69) | −114.7 (±734.14) | −118 (±772.5) |
| Change from Baseline at Month 9 (n = 1) | −23 (±n/a)[c] | −859 (±n/a)[c] | −836 (±n/a)[c] |

[a]Subjects with an assessment at given time point.
[b]Arithmetic mean (standard deviation).
[c]Standard deviation not applicable (1 subject in group).

Amino Acid Assessment: Baseline and Change from Baseline in Isoleucine, Leucine, and Valine Up to Month 9.

End point description. Safety population: all enrolled subjects who received any amount of study medication and had an assessment. End point timeframe: Baseline, Day 7, Month 2, Month 3, Month 4, Month 5, Month 6, Month 9.

TABLE 7

Amino acid assessment. RAVICTI ®: Age 2 Months to <2 Years.

| End Point Value | Isoleucine (μmol/L)[b] | Leucine (μmol/L)[b] | Valine (μmol/L)[b] |
|---|---|---|---|
| Subjects Analyzed | 7[a] | 7[a] | 7[a] |
| Baseline (n = 7) | 54.9 (±19.5) | 90.9 (±29.25) | 171.4 (±42.89) |
| Change from Baseline at Day 7 (n = 6) | 2.7 (±19.16) | −0.8 (±32.76) | 4 (±24.13) |
| Change from Baseline at Month 2 (n = 5) | 4.2 (±45.86) | 9.8 (±65.97) | 40.6 (±90.06) |
| Change from Baseline at Month 3 (n = 2) | −30.5 (±20.51) | −35 (±35.36) | −45.5 (±27.58) |
| Change from Baseline at Month 4 (n = 3) | −12.7 (±16.62) | −21.7 (±19.22) | −17 (±8.19) |
| Change from Baseline at Month 5 (n = 1) | −19 (±n/a)[c] | −32 (±n/a)[c] | −29 (±n/a)[c] |
| Change from Baseline at Month 6 (n = 3) | −20.7 (±9.07) | −30.3 (±11.59) | −33.7 (±10.21) |
| Change from Baseline at Month 9 (n = 1) | 8 (±n/a)[c] | −26 (±n/a)[c] | 70 (±n/a)[c] |

[a]Subjects with an assessment at given time point.
[b]Arithmetic mean (standard deviation).
[c]Standard deviation not applicable (1 subject in group).

Assessment of Growth and Development: Baseline and Change from Baseline in Body Mass Index (BMI) Z-Score and Body Surface Area (BSA) Z-Score Up to Month 9.

End point description. To assess any effect of study drug treatment on growth, Z-scores were calculated to express the deviation from a reference population for BMI and BSA. The BMI Z-scores are based on the World Health Organization's Child Growth Standards charts. The BSA Z-Scores are based on weight-for-length charts. Negative Z-scores indicate lower than typical for age and gender while positive scores indicate higher than typical for age and gender. Safety population: all enrolled subjects who received any amount of study medication and had an assessment. End point timeframe: Baseline, Day 7, Month 2, Month 3, Month 4, Month 5, Month 6, Month 9.

TABLE 8

Assessment of growth and development. RAVICTI ®: Age 2 Months to <2 Years.

| End Point Value | BMI (μmol/L)[b] | BSA (μmol/L)[b] |
|---|---|---|
| Subjects Analyzed | 10[a] | 10[a] |
| Baseline (n = 10) | 0.7947 (±2.17872) | 0.6861 (±2.12644) |
| Change from Baseline at Day 7 (n = 9) | −0.2108 (±0.76495) | −0.1847 (±0.7249) |
| Change from Baseline at Month 2 (n = 7) | 0.0021 (±0.74892) | −0.0437 (±0.70353) |
| Change from Baseline at Month 3 (n = 7) | 0.2129 (±0.84159) | 0.1192 (±0.68159) |
| Change from Baseline at Month 4 (n = 6) | 0.4696 (±1.03769) | 0.3808 (±0.85271) |
| Change from Baseline at Month 5 (n = 3) | 0.164 (±1.15709) | 0.1979 (±0.86261) |
| Change from Baseline at Month 6 (n = 3) | 0.4695 (±1.34487) | 0.3981 (±1.06263) |
| Change from Baseline at Month 9 (n = 1) | 9.5444 (±n/a)[c] | 9.4565 (±n/a)[c] |

[a]Subjects with an assessment at given time point.
[b]Arithmetic mean (standard deviation).
[c]Standard deviation not applicable (1 subject in group).

Plasma Phenylbutyrate/Phenylbutyric Acid (PBA) 1) Maximum Plasma Concentration (Cmax); 2) Minimum Plasma Concentration (Cmin); 3) Area Under the Curve from Time Zero to the Time of Last Quantifiable Concentration (AUC [0-Last]); and 4) Time to Cmax (Tmax) on the First Full Day of RAVICTI® Dosing.

End point description. Pharmacokinetic (PK) Evaluable Population: all subjects from the safety population with individual concentration-time profiles that allow computation of meaningful PK parameter values. End point timeframe: Hour 0 and between 4 and 6 hours, 8 hours, and between 12 and 24 hours after the first dose of the day on Day 1 for stable subjects and on Day 2 for subjects in HAC.

TABLE 9

Plasma PBA PK parameters. RAVICTI®: Age 2 Months to <2 Years; 10 Subjects Analyzed.

| Plasma PBA | End Point Value[a] |
|---|---|
| $C_{max}$ | 42.44 (±36.715) (μg/mL) |
| $C_{min}$ | 1.697 (±2.254) (μg/mL) |
| $AUC_{[0-last]}$ | 280.936 (±293.553) (μg * hr/mL) |
| $T_{max}$ | 8.383 (±4.564) (hrs) |

[a]Arithmetic mean (standard deviation).

Plasma Phenylacetate/Phenylacetic Acid (PAA) 1) Maximum Plasma Concentration (Cmax); 2) Minimum Plasma Concentration (Cmin); 3) Area Under the Curve from Time Zero to the Time of Last Quantifiable Concentration (AUC [0-Last]); and 4) Time to Cmax (Tmax) on the First Full Day of RAVICTI® Dosing.

End point description. PK Evaluable Population: all subjects from the safety population with individual concentration-time profiles that allow computation of meaningful PK parameter values. End point timeframe: Hour 0 and between 4 and 6 hours, 8 hours, and between 12 and 24 hours after the first dose of the day on Day 1 for stable subjects and on Day 2 for subjects in HAC.

TABLE 10

Plasma PAA PK parameters. RAVICTI®: Age 2 Months to <2 Years; 10 Subjects Analyzed.

| Plasma PAA | End Point Value[a] |
|---|---|
| $C_{max}$ | 36.52 (±31.784) (μg/mL) |
| $C_{min}$ | 4.197 (±6.434) (μg/mL) |
| $AUC_{[0-last]}$ | 246.126 (±238.547) (μg * hr/mL) |
| $T_{max}$ | 7.422 (±7.351) (hrs) |

[a]Arithmetic mean (standard deviation).

Plasma Phenylacetylglutamine (PAGN) 1) Maximum Plasma Concentration (Cmax); 2) Minimum Plasma Concentration (Cmin); 3) Area Under the Curve from Time Zero to the Time of Last Quantifiable Concentration (AUC[0-Last]); and 4) Time to Cmax (Tmax) on the First Full Day of RAVICTI® Dosing.

End point description. PK Evaluable Population: all subjects from the safety population with individual concentration-time profiles that allow computation of meaningful PK parameter values. End point timeframe: Hour 0 and between 4 and 6 hours, 8 hours, and between 12 and 24 hours after the first dose of the day on Day 1 for stable subjects and on Day 2 for subjects in HAC.

TABLE 11

Plasma PAGN PK parameters. RAVICTI®: Age 2 Months to <2 Years; 10 Subjects Analyzed.

| Plasma PAGN | End Point Value[a] |
|---|---|
| $C_{max}$ | 62.45 (±27.281) (μg/mL) |
| $C_{min}$ | 20.62 (±14.529) (μg/mL) |
| $AUC_{[0-last]}$ | 583.835 (±285.241) (μg * hr/mL) |
| $T_{max}$ | 6.573 (±7.181) (hrs) |

[a]Arithmetic mean (standard deviation).

Assessment of Urinary PAGN Concentrations on the First Full Day of RAVICTI® Dosing.

End point description. Urinary PAGN concentration was measured through urine collection. PK Evaluable Population: all subjects from the safety population with individual concentration-time profiles that allow computation of meaningful PK parameter values. End point timeframe: Hour 0 and between 0.5 and 1 hour, 1.5 and 2.5 hours, 4 and 6 hours, 7.5 and 8.5 hours, and between 12 and 24 hours after the first dose of the day on Day 1 for stable subjects and on Day 2 for subjects in HAC.

TABLE 12

Urinary PAGN assessment. RAVICTI®: Age 2 Months to <2 Years.

| End Point Value | Number |
|---|---|
| Subjects Analyzed | 9[a] |
| (μg/mL)[b] | |
| Hour 0 (n = 6) | 3478.3 (±1775.4) |
| Hour 0.5 to 1 (n = 6) | 4140.2 (±4398.8) |
| Hour 1.5 to 2.5 (n = 9) | 3145.2 (±5044.5) |
| Hour 4 to 6 (n = 9) | 5201.6 (±4546.6) |
| Hour 7.5 to 8.5 (n = 7) | 4290 (±3147.2) |
| Hour 12 to 24 (n = 9) | 7561.1 (±6955.7) |

[a]Subjects with an assessment at given time point.
[b]Arithmetic mean (standard deviation).

Adverse Events Information.

Timeframe for reporting adverse events: From first dose of study treatment up to 370 days (data cutoff); median (full range) duration of treatment was 4.68 (0.2 to 10.9) months. Adverse event reporting additional description: TEAEs (defined as AEs with an onset date on or after the first dose of study medication until study discontinuation) are presented.

TABLE 13

Serious adverse events. RAVICTI®: Age 2 Months to <2 Years.

| End Point Value | Number |
|---|---|
| Total Subjects Affected | |
| Subjects Affected/Exposed | 6/10 (60%) |
| Number of Deaths (All Causes) | 1 |
| Number of Deaths Resulting from AEs | |

TABLE 13-continued

Serious adverse events. RAVICTI ®: Age 2 Months to <2 Years.

| | Subjects Affected/ Exposed | Occurrences Causally Related to Treatment/All | Deaths Causally Related to Treatment/All |
|---|---|---|---|
| Respiratory, Thoracic and Mediastinal Disorders (Apnoeic Attack) | 1/10 (10%) | 0/2 | 0/0 |
| General Disorders and Administration Site Conditions (Pneumatosis) | 1/10 (10%) | 0/1 | 0/1 |
| Hepatobiliary Disorders (Hyperammonaemia) | 4/10 (40%) | 0/8 | 0/0 |
| Infections and Infestations | | | |
| (Gastroenteritis) | 1/10 (10%) | 0/1 | 0/0 |
| (Croup) | 1/10 (10%) | 0/1 | 0/0 |
| (Viral) | 1/10 (10%) | 0/1 | 0/0 |
| (Urinary Tract) | 1/10 (10%) | 0/1 | 0/0 |

TABLE 14

Non-serious adverse events[a]. RAVICTI ®: Age 2 Months to <2 Years.

| End Point Value | Subjects Affected/Exposed | Occurrences (All) |
|---|---|---|
| Total Subjects Affected | 10/10 (100%) | |
| Vascular Disorders (Deep Vein Thrombosis) | 1/10 (10%) | 1 |
| Injury, Poisoning, and Procedural Complications | | |
| (Stoma Site Reaction) | 1/10 (10%) | 1 |
| (Tibia Fracture) | 1/10 (10%) | 1 |
| Respiratory, Thoracic, and Mediastinal Disorders | | |
| (Cough) | 1/10 (10%) | 1 |
| (Rhinorrhoea) | 1/10 (10%) | 1 |
| (Apnoeic Attack) | 1/10 (10%) | 1 |
| Blood and Lymphatic System Disorders (Anaemia) | 1/10 (10%) | 1 |
| Nervous System Disorders (Gross Motor Delay) | 1/10 (10%) | 1 |
| Gastrointestinal Disorders | | |
| (Diarrhoea) | 1/10 (10%) | 1 |
| (Vomiting) | 2/10 (20%) | 3 |
| (Teething) | 1/10 (10%) | 1 |
| Renal and Urinary Disorders (Vesicoureteric Reflux) | 1/10 (10%) | 1 |
| Skin and Subcutaneous Tissue Disorders | | |
| (Nail Ridging) | 1/10 (10%) | 1 |
| (Rash) | 2/10 (20%) | 2 |
| Metabolism and Nutrition Disorders | | |
| (Metabolic Acidosis) | 1/10 (10%) | 1 |
| (Hypophagia) | 1/10 (10%) | 1 |
| Infections and Infestations | | |
| (Gastroenteritis) | 1/10 (10%) | 1 |
| (Upper Respiratory Tract) | 3/10 (30%) | 4 |
| (Urinary Tract) | 1/10 (10%) | 1 |
| (Viral) | 1/10 (10%) | 1 |
| (Nasopharyngitis) | 1/10 (10%) | 1 |

[a]Frequency threshold for reporting non-serious adverse events = 0%.

Example 3

Sixteen newborn infants aged 0 to 27 days, and 10 infants and toddlers aged 28 days to 23 months received RAVICTI Oral Liquid administered just prior to breastfeeding or intake of formula or food. The recommended dosing regimen was 3-6 times per day depending on feeding schedule.

TABLE 15

Number of subjects in study period.

| | RAVICTI: Age 2 months to <2 years (mean 9.87 months ± 5.529) | RAVICTI: Age 0 to <2 months (mean 0.83 months ± 0.697) |
|---|---|---|
| Started | 10 (5 females, 5 males) | 16 (7 females, 9 males) |
| Completed | 6 | 10 |
| Not Completed | 4 | 6 |
| Withdrawal by parent/guardian | 0 | 0 |
| Stopping rule: Liver transplant | 2 | 4 |
| Adverse event | 1 | 1 |
| Lost to follow-up | 1 | 1 |

The number of subjects reported to be in the baseline period are not the same as the worldwide number enrolled in the trial. It is expected that these numbers will be the same. One subject enrolled in the study and prior to taking study drug the parents decided not to be dosed.

The starting dose of RAVICTI was based on UCD status (newly diagnosed, or already stable on sodium phenylbutyrate [NaPBA] and/or sodium benzoate [NaBz]) and whether a hyperammonemic crisis was present. Subsequently, the dose may have been adjusted based on clinical and/or ammonia results, according to an algorithm provided in the protocol. One subject enrolled in the study, and prior to taking study drug the parents decided not to be dosed. Percentage of Subjects with Successful Transition to RAVICTI With Controlled Ammonia (i.e., No Clinical Symptoms and Ammonia <100 µmol/L)

For subjects 2 months of age and older, after a minimum of 24 hours of ammonia monitoring following the first full dose of RAVICTI alone, the subject was effectively transitioned when following conditions were met: no signs and symptoms of hyperammonemia; ammonia level less than 100 µmol/L (without normalization of ammonia, i.e., without conversion of values from local laboratories with varying normal ranges to standardized values); and eligible for discharge.

For subjects 0 to <2 months of age, after a minimum of 24 hours of ammonia monitoring following the first full dose of RAVICTI alone, the subject was effectively transitioned when following conditions were met: no signs and symptoms of hyperammonemia; ammonia level less than 100 µmol/L (without normalization of ammonia, i.e., without conversion of values from local laboratories with varying normal ranges to standardized values); and eligible for discharge.

Rate of Hyperammonemic Crises (HACs)

Hyperammonemic crisis (HAC) was defined as having signs and symptoms consistent with hyperammonemia (such as, but not limited to, frequent vomiting, nausea, headache, lethargy, irritability, combativeness, and/or somnolence) associated with high blood ammonia and requiring medical intervention. Rate of HACs prior to enrollment was calculated as sum of (number of HAC)/sum of (subject age in days at the time of enrollment or 365 days, whichever was less) across all subjects in the corresponding group. Rate of HACs per 6 months during the safety extension was calculated as sum of (number of HAC)/sum of (days during first 6 months starting on Day 8 or number days on RAVICTI, whichever is less) across all subjects in the corresponding group.

For subjects aged 2 months and up to 2 years, 6 subjects were assessed for HACs, and HACs were identified at a ratio of 0.005.

For subjects aged 1 to less than 2 months, 16 subjects were assessed for HACs, and HACs were identified at a ratio of 0.003.

Number of Subjects with Treatment-Emergent Adverse Events (TEAEs), Serious TEAEs, Deaths, and Discontinuations Due to TEAEs An adverse event (AE) is any untoward medical occurrence, whether or not the event is considered related to the study drug. A serious AE is any AE that: results in death; is life threatening; requires hospitalization or prolongation of existing hospitalization; results in disability/incapacity; is a congenital anomaly/birth defect; is an important medical event. TEAEs are defined as AEs with an onset date on or after the first dose of study medication until study discontinuation. The Investigator assessed the causal relationship of each TEAE to the study drug as not related, possibly related, or probably related. From the first dose of study treatment through 30 days after the final dose (mean [SD] duration of treatment was 9.13 [6.838] months).

For subjects aged 2 months and up to 2 years, of the 10 subjects analyzed, all 10 experienced one or more TEAE. Four subjects experienced one or more related TEAE; 6 experienced one or more serious TEAE, and no subjects experienced serious related TEAEs. One subject experienced a fatal outcome TEAE, and one subject experienced a TEAE leading to study discontinuation.

For subjects aged 0 to 2 months, of the 16 subjects analyzed, all 16 experienced one or more TEAE. Ten subjects experienced one or more related TEAE; 11 experienced one or more serious TEAE, and no subjects experienced serious related TEAEs. There were no fatal outcome TEAEs, and one subject experienced a TEAE leading to study discontinuation.

Baseline and Change from Baseline in Glutamate Up to Month 24

Glutamate measurements were taken on day 7, month 2, month 3, month 4, month 5, month 6, month 9, month 12, month 15, and month 24.

TABLE 16

Glutamate baseline and changes (µmol/L).

| | RAVICTI: Age 2 months to <2 years | RAVICTI: Age 0 to <2 months |
|---|---|---|
| Number of subjects analyzed | 10 | 16 |
| Baseline | 122.43 (±118.620); n = 7 | 84.97 (±52.086); n = 15 |
| Day 7 change from baseline | −54.50 (±92.626); n = 6 | 26.81 (±76.417); n = 14 |
| Month 2 change from Baseline | 7.80 (±25.646); n = 5 | 25.16 (±64.474); n = 14 |
| Month 3 change from Baseline | −16.33 (±39.209); n = 3 | 50.05 (±73.988); n = 14 |
| Month 4 change from Baseline | −13.00 (±39.590); n = 4 | 18.77 (±67.561); n = 11 |
| Month 5 change from Baseline | 0.25 (±13.426); n = 4 | 57.43 (±98.550); n = 10 |
| Month 6 change from Baseline | −2.20 (±34.463); m = 5 | 43.65 (±140.985); n = 8 |
| Month 9 change from Baseline | 30.80 (±17.092); n = 3 | 33.41 (±150.273); n = 8 |
| Month 12 change from Baseline | 22.20 (±23.506); n = 3 | 8.75 (±97.329); n = 4 |
| Month 15 change from Baseline | 39.00 (±00000); n = 1 | 25.75 (±62.660); n = 4 |

TABLE 16-continued

Glutamate baseline and changes (μmol/L).

| | RAVICTI: Age 2 months to <2 years | RAVICTI: Age 0 to <2 months |
|---|---|---|
| Month 18 change from Baseline | — | 2.50 (±21.920); n = 2 |
| Month 24 change from Baseline | 48.00 (±53.740); n = 2 | 16.10 (±95.461); n = 8 | n = subjects with an assessment at given time point; 00000 = not applicable (1 subject assessed).

Baseline and Change from Baseline in Glutamine Up to Month 24

Glutamine measurements were taken on day 7, month 2, month 3, month 4, month 5, month 6, month 9, month 12, month 15, month 18, and month 24.

TABLE 17

Glutamine baseline and changes (μmol/L).

| | RAVICTI: Age 2 months to <2 years | RAVICTI: Age 0 to <2 months |
|---|---|---|
| Number of subjects analyzed | 10 | 16 |
| Baseline | 750.43 (±309.000); n = 7 | 508.83 (±337.175); n = 15 |
| Day 7 change from baseline | −184.33 (±168.657); n = 6 | 21.04 (±260.500); n = 14 |
| Month 2 change from Baseline | −174.60 (±318.249); n = 5 | −27.62 (±379.796); n = 14 |
| Month 3 change from Baseline | −374.00 (±425.903); n = 3 | −15.09 (±352.471); n = 14 |
| Month 4 change from Baseline | −252.75 (±323.852); n = 4 | −113.98 (±230.855); n = 11 |
| Month 5 change from Baseline | −370.25 (±377.222); n = 4 | −99.82 (±305.674); n = 10 |
| Month 6 change from Baseline | −113.20 (±519.710); n = 5 | −138.16 (±349.269); n = 8 |
| Month 9 change from Baseline | −446.53 (±360.457); n = 3 | −56.08 (±269.288); n = 8 |
| Month 12 change from Baseline; | −450.50 (±386.699); n = 3 | −181.50 (±118.604); n = 4 |
| Month 15 change from Baseline | −149.00 (±00000); n = 1 | −103.75 (±328.583); n = 4 |
| Month 18 change from Baseline | — | −184.00 (±80.610); n = 2 |
| Month 24 change from Baseline | 195.00 (±554.372); n = 2 | −219.93 (±279.815); n = 8 | n = subjects with an assessment at given time point; 00000 = not applicable (1 subject assessed).

Baseline and Change from Baseline in Sum of Glutamine and Glutamate Up to Month 24

Measurements were taken on day 7, month 2, month 3, month 4, month 5, month 6, month 9, month 12, month 15, month 18, and month 24.

TABLE 18

Sum of glutamine and glutamate baseline and changes (μmol/L).

| | RAVICTI: Age 2 months to <2 years | RAVICTI: Age 0 to <2 months |
|---|---|---|
| Number of subjects analyzed | 10 | 16 |
| Baseline | 872.86 (±381.005); n = 7 | 593.80 (±333.657); n = 15 |
| Day 7 change from baseline | −238.83 (±203.567); n = 6 | 47.85 (±230.343); n = 14 |
| Month 2 change from Baseline | −166.80 (±332.421); n = 5 | −2.46 (±402.919); n = 14 |
| Month 3 change from Baseline | −390.33 (±462.292); n = 3 | 34.96 (±371.522); n = 14 |
| Month 4 change from Baseline | −265.75 (±339.015); n = 4 | −95.21 (±238.136); n = 11 |
| Month 5 change from Baseline | −370.00 (±379.884); n = 4 | −42.39 (±288.782); n = 10 |
| Month 6 change from Baseline | −115.40 (±546.796); n = 5 | −94.51 (±297.378); n = 8 |
| Month 9 change from Baseline | −415.73 (±365.419); n = 3 | −22.66 (±318.034); n = 8 |
| Month 12 change from Baseline | −428.30 (±404.351); n = 3 | −172.75 (±210.202); n = 4 |
| Month 15 change from Baseline | −110.00 (±00000); n = 1 | −78.00 (±297.410); n = 4 |
| Month 18 change from Baseline | — | −181.50 (±102.530); n = 2 |
| Month 24 change from Baseline | 243.00 (±608.112); n = 2 | −203.83 (±255.810); n = 8 | n = subjects with an assessment at given time point; 00000 = not applicable (1 subject assessed).

Baseline and Change from Baseline in Isoleucine Up to Month 24

Isoleucine measurements were taken on day 7, month 2, month 3, month 4, month 5, month 6, month 9, month 12, month 15, month 18, and month 24.

TABLE 19

Isoleucine baseline and changes (μmol/L).

| | RAVICTI: Age 2 months to <2 years | RAVICTI: Age 0 to <2 months |
|---|---|---|
| Number of subjects analyzed | 10 | 16 |
| Baseline | 54.86 (±19.497); n = 7 | 142.68 (±222.694); n = 15 |
| Day 7 change from baseline | 2.67 (±19.159); n = 6 | −49.09 (±198.730); n = 14 |
| Month 2 change from Baseline | 4.20 (±45.861); n = 5 | −1.62 (±233.754); n = 14 |
| Month 3 change from Baseline | −25.67 (±16.743); n = 3 | −20.46 (±216.885); n = 14 |
| Month 4 change from Baseline | −20.25 (±20.353); n = 4 | −67.32 (±173.564); n = 11 |
| Month 5 change from Baseline | −20.00 (±36.341); n = 4 | −75.45 (±221.845); n = 10 |
| Month 6 change from Baseline | −16.40 (±12.137); n = 5 | −35.94 (±78.367); n = 8 |
| Month 9 change from Baseline | −6.73 (±13.342); n = 3 | −73.09 (±245.051); n = 8 |
| Month 12 change from Baseline | −13.33 (±15.885); n = 3 | −178.50 (±335.538); n = 4 |
| Month 15 change from Baseline | −18.00 (±00000); n = 1 | −139.50 (±359.287); n = 4 |
| Month 18 change from Baseline | — | 1.00 (±45.255); n = 2 |
| Month 24 change from Baseline | 1.50 (±10.607); n = 2 | −55.31 (±217.209); n = 8 | n = subjects with an assessment at given time point; 00000 = not applicable (1 subject assessed).

Baseline and Change from Baseline in Leucine Up to Month 24

Leucine measurements were taken on day 7, month 2, month 3, month 4, month 5, month 6, month 9, month 12, month 15, month 18, and month 24.

TABLE 20

Leucine baseline and changes (μmol/L).

|  | RAVICTI: Age 2 months to <2 years | RAVICTI: Age 0 to <2 months |
|---|---|---|
| Number of subjects analyzed | 10 | 16 |
| Baseline | 90.86 (±29.249'); n = 7 | 133.67 (±253.829); n = 15 |
| Day 7 change from baseline | -0.83 (±32.762); n = 6 | -81.91 (±273.127); n = 14 |
| Month 2 change from Baseline | 9.80 (±65.975); n = 5 | -60.80 (±278.083); n = 14 |
| Month 3 change from Baseline | -33.00 (±25.239); n = 3 | -51.66 (±269.558); n = 14 |
| Month 4 change from Baseline | -31.25 (±24.771); n = 4 | -82.82 (±224.269); n = 11 |
| Month 5 change from Baseline | -39.50 (±61.136); n = 4 | -118.55 (±311.125); n = 10 |
| Month 6 change from Baseline | -25.40 (±13.594); n = 5 | -11.85 (±40.693); n = 8 |
| Month 9 change from Baseline | -19.13 (±39.322); n = 3 | -115.09 (±338.186); n = 8 |
| Month 12 change from Baseline | -34.37 (±23.283); n = 3 | -249.50 (±483.776); n = 4 |
| Month 15 change from Baseline | -40.00 (±00000); n = 1 | -195.75 (±496.313); n = 4 |
| Month 18 change from Baseline | — | 6.00 (±62.225); n = 2 |
| Month 24 change from Baseline | -1.50 (±31.820); n = 2 | -82.54 (±228.107); n = 8 | n = subjects with an assessment at given time point; 00000 = not applicable (1 subject assessed).

Baseline and Change from Baseline in Valine Up to Month 24

Valine measurements were taken on day 7, month 2, month 3, month 4, month 5, month 6, month 9, month 12, month 15, month 18, and month 24.

TABLE 21

Valine baseline and changes (μmol/L).

|  | RAVICTI: Age 2 months to <2 years | RAVICTI: Age 0 to <2 months |
|---|---|---|
| Number of subjects analyzed | 10 | 16 |
| Baseline | 171.43 (±42.887); n = 7 | 181.49 (±257.948); n = 15 |
| Day 7 change from baseline | 4.00 (±24.133); n = 6 | -63.96 (±290.312); n = 14 |
| Month 2 change from Baseline | 40.60 (±90.057); n = 5 | -39.04 (±297.634); n = 14 |
| Month 3 change from Baseline | -27.33 (±37.018); n = 3 | -23.86 (±290.128); n = 14 |
| Month 4 change from Baseline | -31.50 (±29.760); n = 4 | -74.41 (±233.538); n = 11 |
| Month 5 change from Baseline | -56.00 (±75.939); n = 4 | -98.67 (±326.300); n = 10 |
| Month 6 change from Baseline | -21.60 (±18.202); n = 5 | 2.64 (±77.843); n = 8 |
| Month 9 change from Baseline | -11.90 (±71.753); n = 3 | -90.40 (±355.316); n = 8 |
| Month 12 change from Baseline | -48.87 (±51.644); n = 3 | -238.25 (±506.435); n = 4 |
| Month 15 change from Baseline | -46.00 (±0000); n = 1 | -137.00 (±519.042); n = 4 |
| Month 18 change from Baseline | — | 38.00 (±67.882); n = 2 |
| Month 24 change from Baseline | 5.00 (±55.154); n = 2 | -72.78 (±258.710); n = 8 | n = subjects with an assessment at given time point; 00000 = not applicable (1 subject assessed).

Baseline and Change from Baseline in Body Mass Index (BMI) Z-Score Up to Month 24

To assess any effect of study drug treatment on growth, Z-scores were calculated to express the deviation from a reference population for BMI. The Z-scores are based on the World Health Organization's Child Growth Standards charts. Negative Z-scores indicate lower than typical for age and gender while positive scores indicate higher than typical for age and gender. BMI measurements were taken on month 1, month 2, month 3, month 4, month 5, month 6, month 9, month 12, month 15, month 18, and month 24.

TABLE 22

Z-Score baseline and changes.

|  | RAVICTI: Age 2 months to <2 years | RAVICTI: Age 0 to <2 months |
|---|---|---|
| Number of subjects analyzed | 10 | 16 |
| Baseline | 0.8107 (±2.17017); n = 10 | -0.0544 (±1.26821); n = 16 |
| Month 1 change from baseline | -0.2385 (±0.77830); n = 9 | -0.2158 (±1.35960); n = 16 |
| Month 2 change from Baseline | -0.0249 (±0.74861); n = 7 | -0.2598 (±1.19544); n = 15 |
| Month 3 change from Baseline | 0.1815 (±0.86056); n = 7 | -0.1617 (±1.02572); n = 15 |
| Month 4 change from Baseline | 0.4434 (±0.94854); n = 7 | -0.0264 (±1.68215); n = 12 |
| Month 5 change from Baseline | 0.1484 (±0.76293); n = 6 | 0.0828 (±1.14206); n = 11 |
| Month 6 change from Baseline | 0.2497 (±0.80923); n = 7 | 0.0136 (±1.72106); n = 10 |
| Month 9 change from Baseline | 0.6407 (±0.98695); n = 5 | 0.4614 (±1.25343); n = 9 |
| Month 12 change from Baseline | 0.4164 (±0.80674); n = 4 | 0.6646 (±0.95334); n = 6 |
| Month 15 change from Baseline | -0.2997 (±0.16959); n = 2 | 0.6830 (±0.55703); n = 4 |
| Month 18 change from Baseline | -0.2038 (±00000); n = 1 | 0.3308 (±0.27572); n = 3 |
| Month 24 change from Baseline | 0.5581 (±1.23993); n = 4 | 0.7743 (±0.64962); n = 10 | n = subjects with an assessment at given time point; 00000 = not applicable (1 subject assessed).

Baseline and Change from Baseline in Body Surface Area (BSA) Z-Score Up to Month 24

To assess any effect of study drug treatment on growth, Z-scores were calculated to express the deviation from a reference population for BSA. The Z-scores are based on weight-for-length charts. Negative Z-scores indicate lower than typical for age and gender while positive scores indicate higher than typical for age and gender. BMI measurements were taken on month 1, month 2, month 3, month 4, month 5, month 6, month 9, month 12, month 15, month 18, and month 24.

TABLE 23

Z-Score baseline and changes.

|  | RAVICTI: Age 2 months to <2 years | RAVICTI: Age 0 to <2 months |
|---|---|---|
| Number of subjects analyzed | 10 | 16 |
| Baseline | 0.7143 (±2.14922); n = 10 | -0.1980 (±2.11774); n = 16 |
| Month 1 change from baseline | -0.2105 (±0.74135); n = 9 | 0.2336 (±1.95603); n = 16 |
| Month 2 change from Baseline | -0.0704 (±0.70393); n = 7 | 0.2006 (±1.72135); n = 15 |

TABLE 23-continued

Z-Score baseline and changes.

|  | RAVICTI: Age 2 months to <2 years | RAVICTI: Age 0 to <2 months |
|---|---|---|
| Month 3 change from Baseline | 0.1065 (±0.70165); n = 7 | 0.2684 (±1.37517); n = 15 |
| Month 4 change from Baseline | 0.3365 (±0.77672); n = 7 | 0.2372 (±2.30831); n = 12 |
| Month 5 change from Baseline | 0.1043 (±0.56747); n = 6 | 0.1810 (±1.70024); n = 11 |
| Month 6 change from Baseline | 0.1842 (±0.62205); n = 7 | 0.2902 (±2.05956); n = 10 |
| Month 9 change from Baseline | 0.4875 (±0.86137); n = 5 | 0.1679 (±1.32407); n = 9 |
| Month 12 change from Baseline | 0.2944 (±0.75133); n = 4 | 0.1308 (±0.50371); n = 6 |
| Month 15 change from Baseline | −0.3661 (±0.00932); n = 2 | 0.1595 (±0.75833); n = 4 |
| Month 18 change from Baseline | −0.2214 (±00000); n = 1 | 0.1050 (±0.73521); n = 3 |
| Month 24 change from Baseline | 0.4310 (±1.13140); n = 4 | 0.7341 (±1.35582); n = 10 | n = subjects with an assessment at given time point; 00000 = not applicable (1 subject assessed).

Plasma Phenylbutyrate/Phenylbutyric Acid (PBA) Maximum Plasma Concentration (Cmax) on the First Full Day of RAVICTI Dosing Pharmacokinetic (PK) Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean Cmax was 42.11 (±36.715) µg/mL.

For subjects aged 0 to 2 months, of the 16 subjects analyzed, the mean Cmax was 46.2 (±49.8) µg/mL.

Plasma PBA Minimum Plasma Concentration (Cmin) on the First Full Day of RAVICTI Dosing PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean Cmin was 1.697 (±2.254) µg/mL.

For subjects aged 0 to 2 months, of the 7 subjects analyzed, the mean Cmin was 4.8 (±4.2) µg/mL.

Plasma PBA Area Under the Curve from Time Zero to the Time of Last Quantifiable Concentration (AUC[0-Last]) on the First Full Day of RAVICTI Dosing PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean AUC[0-last]) was 280.936 (±293.553)µg*hr/mL.

For subjects aged 0 to 2 months, of the 16 subjects analyzed, the mean AUC[0-last]) was 374.53 (±390.48) µg*hr/mL.

Plasma PBA Time to Cmax (Tmax) on the First Full Day of RAVICTI Dosing

PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean Tmax was 8.383 (±4.564) hr.

For subjects aged 0 to 2 months, of the 16 subjects analyzed, the mean Tmax was 9.39 (±7.41) hr.

Plasma Phenylacetate/Phenylacetic Acid (PAA) Cmax on the First Full Day of RAVICTI Dosing PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean plasma PAA Cmax was 36.52 (±31.784) µg/mL.

For subjects aged 0 to 2 months, of the 16 subjects analyzed, the mean plasma PAA Cmax was 115.3 (±102.0) µg/mL.

Plasma PAA Cmin on the First Full Day of RAVICTI Dosing

PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean plasma PAA Cmin was 4.197 (±6.434) µg/mL.

For subjects aged 0 to 2 months, of the 10 subjects analyzed, the mean plasma PAA Cmin was 98.98 (±122.07) µg/mL.

Plasma PAA AUC(0-Last) on the First Full Day of RAVICTI Dosing

PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean plasma PAA AUC(0-last) was 246.126 (±238.547)µg*hr/mL.

For subjects aged 0 to 2 months, of the 16 subjects analyzed, the mean plasma PAA AUC(0-last) was 1321.18 (±1220.52)µg*hr/mL.

Plasma PAA Tmax on the First Full Day of RAVICTI Dosing

PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean plasma PAA Tmax was 7.422 (±7.351) hr.

For subjects aged 0 to 2 months, of the 16 subjects analyzed, the mean plasma PAA Tmax was 9.85 (±9.26) hr.
Plasma Phenylacetylglutamine (PAGN) Cmax on the First Full Day of RAVICTI Dosing PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean PAGN Cmax was 62.45 (±27.281) μg/mL.

For subjects aged 0 to 2 months, of the 16 subjects analyzed, the mean PAGN Cmax was 102.1 (±48.6) μg/mL.
Plasma Phenylacetylglutamine (PAGN) Cmin on the First Full Day of RAVICTI Dosing PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean PAGN Cmin was 20.62 (±14.529) μg/mL.

For subjects aged 0 to 2 months, of the 13 subjects analyzed, the mean PAGN Cmin was 69.39 (±54.03) μg/mL.
Plasma PAGN AUC(0-Last) on the First Full Day of RAVICTI Dosing PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean PAGN AUC(0-last) was 583.835 (±285.241)μg*hr/mL.

For subjects aged 0 to 2 months, of the 16 subjects analyzed, the mean PAGN AUC(0-last) was 1384.12 (±1141.03)μg*hr/mL.
Plasma PAGN Tmax on the First Full Day of RAVICTI Dosing PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean PAGN Tmax was 6.573 (±7.181) hr.

For subjects aged 0 to 2 months, of the 16 subjects analyzed, the mean PAGN Tmax was 11.72 (±8.24) hr.

Urinary PAGN Concentrations on the First Full Day of RAVICTI Dosing

PK Evaluable Population: all subjects from the safety population with individual concentration-time profiles that allow computation of meaningful PK parameter values. Measurements were taken at hour 0, between 0.5 and 1.5 hours, between 1.5 and 2.5 hours, between 4 and 6 hours, between 7.5 and 8.5 hours, and between 12 and 24 hours after the first dose of the day on day 1 for stable subjects and on day 2 for subjects in HAC.

TABLE 24

Urinary PAGN Concentrations (μg/mL).

| | RAVICTI: Age 2 months to <2 years | RAVICTI: Age 0 to <2 months |
|---|---|---|
| Number of subjects analyzed | 10 | 16 |
| Hour 0 | 3273 (±1993); n = 6 | 3530.43 (±3600.4); n = 6 |
| 0.5 to 1.5 hours | 4140 (±4399); n = 6 | 1828 (±2862); n = 8 |
| 1.5 to 2.5 hours | 3145 (±5045); n = 9 | 1746 (±1464); n = 9 |
| 4 to 6 hours | 5202 (±4547); n = 9 | 2260 (±1472); n = 11 |
| 7.5 to 8.5 hours | 3950 (±3068); n = 8 | 3530.43 (±3600.4), n = 14 |
| 12 to 24 hours | 7561 (±6956); n = 9 | 4404 (±3766); n = 16 |

Urinary PAGN Concentrations Up to End of Trial

PK Evaluable Population: all subjects from the safety population with individual concentration-time profiles that allow computation of meaningful PK parameter values. Measurements were taken at day 7, month 1, month 2, month 3, month 4, month 5, month 6, month 9, month 12, month 15, month 18, month 24, and at the end of the trial.

TABLE 25

Urinary PAGN Concentrations (μg/mL).

| | RAVICTI: Age 2 months to <2 years | RAVICTI: Age 0 to <2 months |
|---|---|---|
| Number of subjects analyzed | 10 | 16 |
| Day 7 | 8859 (±10500); n = 8 | 4643 (±2506); n = 10 |
| Month 1 | 6274 (±4802); n = 8 | 4517 (±2485), n = 11 |
| Month 2 | 7386 (±6419); n = 5 | 4116 (±3137); n = 12 |
| Month 3 | 11456 (±14471); n = 6 | 7037 (±4493); n = 9 |
| Month 4 | 21416 (±33695); n = 3 | 2826 (±1543); n = 9 |
| Month 5 | 6129 (±8024); n = 5 | 6973 (±3682); n = 8 |
| Month 6 | 5347 (±3153); n = 3 | 5883 (±3128); n = 3 |
| Month 9 | 9357 (±7286); n = 3 | 7006 (±4289); n = 7 |
| Month 12 | 2580 (±286); n = 3 | 5847 (±2992); n = 3 |
| Month 15 | 6400 (±00000); n = 1 | 3915 (±2584); n = 4 |
| Month 18 | 5250 (±00000); n = 1 | — |
| End of trial | 25333 (±21324); n = 3 | 6939 (±6581); n = 8 |

Plasma PAGN Tmax on the First Full Day of RAVICTI Dosing

PK Evaluable Population: all subjects from the safety population with individual concentration-time profiles that allow computation of meaningful PK parameter values. Measurements were taken at hour 0, between 4 and 6 hours, 8 hours, and between 12 and 24 hours after the first dose of the day on day 1 for stable subjects and on day 2 for subjects in HAC.

For subjects aged 2 months and up to 2 years, of the 10 subjects analyzed, the mean PAGN Tmax was 6.573 (±7.181) hr.

Urinary PAA Concentrations on the First Full Day of RAVICTI Dosing

PK Evaluable Population: all subjects from the safety population with individual concentration-time profiles that allow computation of meaningful PK parameter values. Measurements were taken at hour 0, between 0.5 and 1.5 hours, between 1.5 and 2.5 hours, between 4 and 6 hours, between 7.5 and 8.5 hours, and between 12 and 24 hours after the first dose of the day on day 1 for stable subjects and on day 2 for subjects in HAC.

TABLE 26

Urinary PAA Concentrations (µg/mL).

|  | RAVICTI: Age 2 months to <2 years | RAVICTI: Age 0 to <2 months |
|---|---|---|
| Number of subjects analyzed | 10 | 16 |
| Hour 0 | 18.78 (±27.33); n = 3 | 11.1 (±10.4); n = 3 |
| 0.5 to 1.5 hours | 6.50 (±3.39); n = 4 | 46.2 (±58.6); n = 4 |
| 1.5 to 2.5 hours | 7.29 (±4.10); n = 4 | 62.5 (±42.8); n = 4 |
| 4 to 6 hours | 2.60 (±2.18); n = 6 | 34.6 (±56.2); n = 9 |
| 7.5 to 8.5 hours | 4.48 (±4.38); n = 4 | 22.8 (±25.3); n = 11 |
| 12 to 24 hours | 4.31 (±2.33); n = 4 | 35.2 (±51.0); n = 12 |

Urinary PAA Concentrations Up to End of Trial

PK Evaluable Population: all subjects from the safety population with individual concentration-time profiles that allow computation of meaningful PK parameter values. Measurements were taken at day 7, month 1, month 2, month 3, month 4, month 5, month 6, month 9, month 12, month 15, month 18, month 24, and at the end of the trial.

TABLE 27

Urinary PAA Concentrations (µg/mL).

|  | RAVICTI: Age 2 months to <2 years | RAVICTI: Age 0 to <2 months |
|---|---|---|
| Number of subjects analyzed | 10 | 16 |
| Day 7 | 5.82 (±2.21); n = 2 | 23.7 (±31.2); n = 9 |
| Month 1 | 4.44 (±4.61); n = 6 | 14.6 (±17.2); n = 8 |
| Month 2 | 3.69 (±1.82); n = 3 | 12.3 (±13.3); n = 8 |
| Month 3 | 4.65 (±0.49); n = 2 | 14.4 (±10.7); n = 7 |
| Month 4 | 7.14 (±00000); n = 1 | 6.4 (±7.1); n = 6 |
| Month 5 | 3.27 (±1.96); n = 2 | 13.2 (±14.0); n = 6 |
| Month 6 | 1.59 (±00000); n = 1 | 5.5 (±00000); n = 1 |
| Month 9 | 4.10 (±1.65); n = 3 | 11.8 (±8.5); n = 7 |
| Month 12 | — | 6.0 (±3.8); n = 3 |
| Month 15 | 2.04 (±00000); n = 1 | 4.9 (±0.3); n = 2 |
| Month 18 | 1.64 (±00000); n = 1 | — |
| End of trial | 7.0 (±5.16); n = 3 | 11.6 (±9.0); n = 5 |

TABLE 28

Serious adverse events.

| Serious Adverse Events | RAVICTI: Age 2 Months to <2 Years | RAVICTI: Age 0 to <2 Months |
|---|---|---|
| Total Subjects Affected | | |
| Subjects Affected/Exposed | 6/10 (60%) | 11/16 (68.75%) |
| Number of Deaths (All Causes) | 1 | 0 |
| Number of Deaths Resulting from AEs | | |
| Investigations (Ammonia Increased) | | |
| Subjects Affected/Exposed | 1/10 (10.00%) | 0/16 (0.00%) |
| Occurrences causally related to treatment/all | 0/1 | 0/0 |
| Deaths causally related to treatment/all | 0/0 | 0/0 |
| Cardiac Disorders (Cyanosis) | | |
| Subjects Affected/Exposed | 1/10 (10.00%) | 0/16 (0.00%) |
| Occurrences causally related to treatment/all | 0/2 | 0/0 |
| Deaths causally related to treatment/all | 0/0 | 0/0 |
| Blood and lymphatic system disorders (Neutropenia) | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| Respiratory, Thoracic and Mediastinal Disorders Apnoeic Attack | | |
| Subjects Affected/Exposed | 1/10 (10.00%) | 0/16 (0.00%) |
| Occurrences causally related to treatment/all | 0/2 | 0/0 |
| Deaths causally related to treatment/all | 0/0 | 0/0 |
| Asthma | | |
| Subjects Affected/Exposed | 1/10 (10.00%) | 0/16 (0.00%) |
| Occurrences causally related to treatment/all | 0/1 | 0/0 |
| Deaths causally related to treatment/all | 0/0 | 0/0 |
| Status asthmaticus | | |
| Subjects Affected/Exposed | 1/10 (10.00%) | 0/16 (0.00%) |
| Occurrences causally related to treatment/all | 0/1 | 0/0 |

TABLE 28-continued

Serious adverse events.

| Serious Adverse Events | RAVICTI: Age 2 Months to <2 Years | RAVICTI: Age 0 to <2 Months |
|---|---|---|
| Deaths causally related to treatment/all | 0/0 | 0/0 |
| *Atelectasis* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| *Nervous System Disorders (Lethargy)* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| *General Disorders and Administration Site Conditions (Pyrexia)* | | |
| Subjects Affected/Exposed | 1/10 (10.00%) | 0/16 (0.00%) |
| Occurrences causally related to treatment/all | 0/1 | 0/0 |
| Deaths causally related to treatment/all | 0/0 | 0/0 |
| *Gastrointestinal Disorders Pneumatosis intestinalis* | | |
| Subjects Affected/Exposed | 1/10 (10.00%) | 0/16 (0.00%) |
| Occurrences causally related to treatment/all | 0/1 | 0/0 |
| Deaths causally related to treatment/all | 0/1 | 0/0 |
| *Vomiting* | | |
| Subjects Affected/Exposed | 0/10 (0.00%) | 2/16 (12.50%) |
| Occurrences causally related to treatment/all | 0/0 | 0/2 |
| Deaths causally related to treatment/all | 0/0 | 0/0 |
| *Metabolism and nutrition disorders Hyperammonaemia* | | |
| Subjects Affected/Exposed | 3/10 (30.00%) | 5/16 (31.25%) |
| Occurrences causally related to treatment/all | 0/7 | 0/7 |
| Deaths causally related to treatment/all | 0/0 | 0/0 |
| *Dehydration* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| *Feeding Disorder* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| *Infections and Infestations Croup infectious* | | |
| Subjects Affected/Exposed | 1/10 (10.00%) | 1/16 (6.25%) |
| Occurrences causally related to treatment/all | 0/1 | 0/1 |
| Deaths causally related to treatment/all | 0/0 | 0/0 |
| *Gastroenteritis* | | |
| Subjects Affected/Exposed | 1/10 (10.00%) | 0/16 (0.00%) |
| Occurrences causally related to treatment/all | 0/1 | 0/0 |
| Deaths causally related to treatment/all | 0/0 | 0/0 |
| *Urinary tract infection* | | |
| Subjects Affected/Exposed | 1/10 (10.00%) | 1/16 (6.25%) |
| Occurrences causally related to treatment/all | 0/1 | 0/1 |
| Deaths causally related to treatment/all | 0/0 | 0/0 |
| *Viral infection* | | |
| Subjects Affected/Exposed | 2/10 (20.00%) | 1/16 (6.25%) |
| Occurrences causally related to treatment/all | 0/2 | 0/1 |
| Deaths causally related to treatment/all | 0/0 | 0/0 |
| *Influenza* | | |
| Subjects Affected/Exposed | 1/10 (10.00%) | 0/16 (0.00%) |
| Occurrences causally related to treatment/all | 0/1 | 0/0 |
| Deaths causally related to treatment/all | 0/0 | 0/0 |
| *Peritonitis* | | |
| Subjects Affected/Exposed | 1/10 (10.00%) | 0/16 (0.00%) |
| Occurrences causally related to treatment/all | 0/1 | 0/0 |
| Deaths causally related to treatment/all | 0/1 | 0/0 |
| *Rhinovirus infection* | | |
| Subjects Affected/Exposed | 1/10 (10.00%) | 0/16 (0.00%) |
| Occurrences causally related to treatment/all | 0/1 | 0/0 |
| Deaths causally related to treatment/all | 0/0 | 0/0 |
| *Viral upper respiratory tract infection* | | |
| Subjects Affected/Exposed | 1/10 (10.00%) | 0/16 (0.00%) |
| Occurrences causally related to treatment/all | 0/1 | 0/0 |
| Deaths causally related to treatment/all | 0/0 | 0/0 |
| *Bacteraemia* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| *Cellulitis* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| *Device related infection* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| *Medical device site infection* | | |
| Subjects Affected/Exposed | 0/10 (0.00%) | 1/16 (6.25%) |
| Occurrences causally related to treatment/all | 0/0 | 0/1 |

TABLE 28-continued

Serious adverse events.

| Serious Adverse Events | RAVICTI: Age 2 Months to <2 Years | RAVICTI: Age 0 to <2 Months |
|---|---|---|
| Deaths causally related to treatment/all | 0/0 | 0/0 |
| *Meningitis bacterial* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| *Respiratory syncytial virus infection* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| *Tracheitis* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |
| *Upper respiratory tract infection* | | |
| Subjects Affected/Exposed | 0/10 (0.00%) | 1/16 (6.25%) |
| Occurrences causally related to treatment/all | 0/0 | 0/1 |
| Deaths causally related to treatment/all | 0/0 | 0/0 |

TABLE 29

Non-serious adverse events.

| Non-Serious Adverse Events | RAVICTI: Age 2 Months to <2 Years | RAVICTI: Age 0 to <2 Months |
|---|---|---|
| *Total Subjects Affected* | | |
| Subjects Affected/Exposed | 8/10 (80.00%) | 16/16 (100.00%) |
| *Vascular disorders (Venous thrombosis limb)* | | |
| Subjects Affected/Exposed | 1/10 (10.00%) | 0/16 (0.00%) |
| Occurrences (all) | 2 | 0 |
| *Immune System Disorders (Seasonal allergy)* | | |
| Subjects Affected/Exposed | 1/10 (10.00%) | 0/16 (0.00%) |
| Occurrences (all) | 1 | 0 |
| *General disorders and administration site conditions* | | |
| *Pyrexia* | | |
| Subjects Affected/Exposed | 2/10 (20.00%) | 2/16 (12.50%) |
| Occurrences (all) | 2 | 3 |
| *Catheter site rash* | | |
| Subjects Affected/Exposed | 0/10 (0.00%) | 1/16 (6.25%) |
| Occurrences (all) | 0 | 1 |
| *Device occlusion* | | |
| Subjects Affected/Exposed | 0/10 (0.00%) | 1/16 (6.25%) |
| Occurrences (all) | 0 | 1 |
| *Drug withdrawal syndrome* | | |
| Subjects Affected/Exposed | 0/10 (0.00%) | 1/16 (6.25%) |
| Occurrences (all) | 0 | 1 |
| *Medical device site haemorrhage* | | |
| Subjects Affected/Exposed | 0/10 (0.00%) | 1/16 (6.25%) |
| Occurrences (all) | 0 | 1 |
| *Psychiatric disorders* | | |
| *Agitation* | | |
| Subjects Affected/Exposed | 0/10 (0.00%) | 1/16 (6.25%) |
| Occurrences (all) | 0 | 1 |
| *Irritability* | | |
| Subjects Affected/Exposed | 0/10 (0.00%) | 1/16 (6.25%) |
| Occurrences (all) | 0 | 1 |
| *Injury, poisoning and procedural complications* | | |
| *Stoma site reaction* | | |
| Subjects Affected/Exposed | 1/10 (10.00%) | 1/16 (6.25%) |
| Occurrences (all) | 1 | 1 |
| *Tibia fracture* | | |
| Subjects Affected/Exposed | 1/10 (10.00%) | 0/16 (0.00%) |
| Occurrences (all) | 1 | 0 |
| *Arthropod bite* | | |
| Subjects Affected/Exposed | 0/10 (0.00%) | 1/16 (6.25%) |
| Occurrences (all) | 0 | 1 |
| *Investigations* | | |
| *Amino acid level decreased* | | |
| Subjects Affected/Exposed | 1/10 (10.00%) | 1/16 (6.25%) |
| Occurrences (all) | 1 | 1 |
| *Ammonia increased* | | |
| Subjects Affected/Exposed | 1/10 (10.00%) | 1/16 (6.25%) |
| Occurrences (all) | 1 | 1 |
| *Carbon dioxide decreased* | | |
| Subjects Affected/Exposed | 1/10 (10.00%) | 1/16 (6.25%) |
| Occurrences (all) | 1 | 2 |
| *Hepatic enzyme increased* | | |
| Subjects Affected/Exposed | 0/10 (0.00%) | 2/16 (12.50%) |
| Occurrences (all) | 0 | 2 |
| *Alanine aminotransferase increased* | | |
| Subjects Affected/Exposed | 0/10 (0.00%) | 1/16 (6.25%) |
| Occurrences (all) | 0 | 1 |
| *Amino acid level increased* | | |
| Subjects Affected/Exposed | 0/10 (0.00%) | 1/16 (6.25%) |
| Occurrences (all) | 0 | 2 |
| *Anion gap increased* | | |
| Subjects Affected/Exposed | 0/10 (0.00%) | 1/16 (6.25%) |
| Occurrences (all) | 0 | 1 |
| *Aspartate aminotransferase increased* | | |
| Subjects Affected/Exposed | 0/10 (0.00%) | 1/16 (6.25%) |
| Occurrences (all) | 0 | 1 |
| *Blood bicarbonate decreased* | | |
| Subjects Affected/Exposed | 0/10 (0.00%) | 1/16 (6.25%) |
| Occurrences (all) | 0 | 1 |
| *Blood urea decreased* | | |
| Subjects Affected/Exposed | 0/10 (0.00%) | 1/16 (6.25%) |
| Occurrences (all) | 0 | 1 |
| *Body height below normal* | | |
| Subjects Affected/Exposed | 0/10 (0.00%) | 1/16 (6.25%) |
| Occurrences (all) | 0 | 1 |
| *Gamma-glutamyltransferase increased* | | |
| Subjects Affected/Exposed | 0/10 (0.00%) | 1/16 (6.25%) |
| Occurrences (all) | 0 | 1 |

TABLE 29-continued

Non-serious adverse events.

| Non-Serious Adverse Events | RAVICTI: Age 2 Months to <2 Years | RAVICTI: Age 0 to <2 Months |
|---|---|---|
| Platelet count increased | | |
| Subjects Affected/Exposed | 0/10 (0.00%) | 1/16 (6.25%) |
| Occurrences (all) | 0 | 1 |
| Transaminases increased | | |
| Subjects Affected/Exposed | 0/10 (0.00%) | 1/16 (6.25%) |
| Occurrences (all) | 0 | 1 |
| Weight decreased | | |
| Subjects Affected/Exposed | 0/10 (0.00%) | 1/16 (6.25%) |
| Occurrences (all) | 0 | 1 |
| Cardiac disorders (Tachycardia) | | |
| Subjects Affected/Exposed | 0/10 (0.00%) | 1/16 (6.25%) |
| Occurrences (all) | 0 | 1 |
| Congenital, familial and genetic disorders Dacryostenosis congenital | | |
| Subjects Affected/Exposed | 1/10 (10.00%) | 0/16 (0.00%) |
| Occurrences (all) | 1 | 0 |
| Plagiocephaly | | |
| Subjects Affected/Exposed | 0/10 (0.00%) | 2/16 (12.50%) |
| Occurrences (all) | 0 | 2 |
| Blood and lymphatic system disorders Anaemia | | |
| Subjects Affected/Exposed | 1/10 (10.00%) | 3/16 (18.75%) |
| Occurrences (all) | 1 | 3 |
| Neutropenia | | |
| Subjects Affected/Exposed | 0/10 (0.00%) | 1/16 (6.25%) |
| Occurrences (all) | 0 | 1 |
| Thrombocytopenia | | |
| Subjects Affected/Exposed | 0/10 (0.00%) | 2/16 (12.50%) |
| Occurrences (all) | 0 | 2 |
| Thrombocytosis | | |
| Subjects Affected/Exposed | 0/10 (0.00%) | 2/16 (12.50%) |
| Occurrences (all) | 0 | 2 |
| Leukocytosis | | |
| Subjects Affected/Exposed | 0/10 (0.00%) | 1/16 (6.25%) |
| Occurrences (all) | 0 | 1 |
| Lymphocytosis | | |
| Subjects Affected/Exposed | 0/10 (0.00%) | 1/16 (6.25%) |
| Occurrences (all) | 0 | 1 |
| Microcytic anaemia | | |
| Subjects Affected/Exposed | 0/10 (0.00%) | 1/16 (6.25%) |
| Occurrences (all) | 0 | 1 |
| Respiratory, thoracic and mediastinal disorders Cough | | |
| Subjects Affected/Exposed | 2/10 (20.00%) | 4/16 (25.00%) |
| Occurrences (all) | 2 | 5 |
| Rhinorrhoea | | |
| Subjects Affected/Exposed | 1/10 (10.00%) | 0/16 (0.00%) |
| Occurrences (all) | 1 | 0 |
| Apnoea | | |
| Subjects Affected/Exposed | 1/10 (10.00%) | 0/16 (0.00%) |
| Occurrences (all) | 1 | 0 |
| Nasal congestion | | |
| Subjects Affected/Exposed | 1/10 (10.00%) | 2/16 (12.50%) |
| Occurrences (all) | 1 | 2 |
| Respiratory disorder | | |
| Subjects Affected/Exposed | 1/10 (10.00%) | 0/16 (0.00%) |
| Occurrences (all) | 1 | 0 |
| Oropharyngeal pain | | |
| Subjects Affected/Exposed | 0/10 (0.00%) | 2/16 (12.50%) |
| Occurrences (all) | 0 | 2 |
| Pneumothorax | | |
| Subjects Affected/Exposed | 0/10 (0.00%) | 1/16 (6.25%) |
| Occurrences (all) | 0 | 1 |
| Tachypnoea | | |
| Subjects Affected/Exposed | 0/10 (0.00%) | 1/16 (6.25%) |
| Occurrences (all) | 0 | 1 |
| Use of accessory respiratory muscles | | |
| Subjects Affected/Exposed | 0/10 (0.00%) | 1/16 (6.25%) |
| Occurrences (all) | 0 | 1 |
| Nervous system disorders Gross motor delay | | |
| Subjects Affected/Exposed | 1/10 (10.00%) | 0/16 (0.00%) |
| Occurrences (all) | 1 | 0 |
| Lethargy | | |
| Subjects Affected/Exposed | 0/10 (0.00%) | 1/16 (6.25%) |
| Occurrences (all) | 0 | 1 |
| Tremor | | |
| Subjects Affected/Exposed | 0/10 (0.00%) | 1/16 (6.25%) |
| Occurrences (all) | 0 | 1 |
| Eye disorders Eye discharge | | |
| Subjects Affected/Exposed | 0/10 (0.00%) | 1/16 (6.25%) |
| Occurrences (all) | 0 | 1 |
| Ocular hyperaemia | | |
| Subjects Affected/Exposed | 0/10 (0.00%) | 1/16 (6.25%) |
| Occurrences (all) | 0 | 1 |
| Ear and labyrinth disorders (Excessive cerumen production) | | |
| Subjects Affected/Exposed | 1/10 (10.00%) | 0/16 (0.00%) |
| Occurrences (all) | 1 | 0 |
| Gastrointestinal disorders Diarrhoea | | |
| Subjects Affected/Exposed | 1/10 (10.00%) | 5/16 (31.25%) |
| Occurrences (all) | 1 | 6 |
| Vomiting | | |
| Subjects Affected/Exposed | 4/10 (40.00%) | 5/16 (31.25%) |
| Occurrences (all) | 5 | 12 |
| Teething | | |
| Subjects Affected/Exposed | 1/10 (10.00%) | 3/16 (18.75%) |
| Occurrences (all) | 1 | 3 |
| Constipation | | |
| Subjects Affected/Exposed | 2/10 (20.00%) | 2/16 (12.50%) |
| Occurrences (all) | 2 | 2 |
| Gastrooesophageal reflux disease | | |
| Subjects Affected/Exposed | 0/10 (0.00%) | 6/16 (37.50%) |
| Occurrences (all) | 0 | 6 |
| Flatulence | | |
| Subjects Affected/Exposed | 0/10 (0.00%) | 3/16 (18.75%) |
| Occurrences (all) | 0 | 3 |

TABLE 29-continued

Non-serious adverse events.

| Non-Serious Adverse Events | RAVICTI: Age 2 Months to <2 Years | RAVICTI: Age 0 to <2 Months |
|---|---|---|
| Dysphagia | | |
| Subjects Affected/Exposed | 0/10 (0.00%) | 1/16 (6.25%) |
| Occurrences (all) | 0 | 1 |
| Post-tussive vomiting | | |
| Subjects Affected/Exposed | 0/10 (0.00%) | 1/16 (6.25%) |
| Occurrences (all) | 0 | 1 |
| Hepatobiliary disorders (Hepatic calcification) | | |
| Subjects Affected/Exposed | 0/10 (0.00%) | 1/16 (6.25%) |
| Occurrences (all) | 0 | 1 |
| Renal and urinary disorders Vesicoureteric reflux | | |
| Subjects Affected/Exposed | 1/10 (10.00%) | 0/16 (0.00%) |
| Occurrences (all) | 1 | 0 |
| Nephrolithiasis | | |
| Subjects Affected/Exposed | 0/10 (0.00%) | 1/16 (6.25%) |
| Occurrences (all) | 0 | 1 |
| Skin and subcutaneous tissue disorders Nail ridging | | |
| Subjects Affected/Exposed | 1/10 (10.00%) | 0/16 (0.00%) |
| Occurrences (all) | 1 | 0 |
| Rash | | |
| Subjects Affected/Exposed | 2/10 (20.00%) | 5/16 (31.25%) |
| Occurrences (all) | 3 | 6 |
| Dermatitis diaper | | |
| Subjects Affected/Exposed | 1/10 (10.00%) | 6/16 (37.50%) |
| Occurrences (all) | 1 | 6 |
| Eczema | | |
| Subjects Affected/Exposed | 1/10 (10.00%) | 1/16 (6.25%) |
| Occurrences (all) | 1 | 2 |
| Red man syndrome | | |
| Subjects Affected/Exposed | 0/10 (0.00%) | 1/16 (6.25%) |
| Occurrences (all) | 0 | 1 |
| Seborrhoeic dermatitis | | |
| Subjects Affected/Exposed | 1/10 (10.00%) | 1/16 (6.25%) |
| Occurrences (all) | 1 | 2 |
| Musculoskeletal and connective tissue Disorders (Torticollis) | | |
| Subjects Affected/Exposed | 0/10 (0.00%) | 1/16 (6.25%) |
| Occurrences (all) | 0 | 1 |
| Metabolism and nutrition disorders Metabolic acidosis | | |
| Subjects Affected/Exposed | 2/10 (20.00%) | 2/16 (12.50%) |
| Occurrences (all) | 2 | 2 |
| Hypophagia | | |
| Subjects Affected/Exposed | 2/10 (20.00%) | 1/16 (6.25%) |
| Occurrences (all) | 3 | 1 |
| Hyperammonaemia | | |
| Subjects Affected/Exposed | 0/10 (0.00%) | 2/16 (12.50%) |
| Occurrences (all) | 0 | 3 |
| Dehydration | | |
| Subjects Affected/Exposed | 0/10 (0.00%) | 2/16 (12.50%) |
| Occurrences (all) | 0 | 4 |
| Decreased appetite | | |
| Subjects Affected/Exposed | 0/10 (0.00%) | 1/16 (6.25%) |
| Occurrences (all) | 0 | 2 |

TABLE 29-continued

Non-serious adverse events.

| Non-Serious Adverse Events | RAVICTI: Age 2 Months to <2 Years | RAVICTI: Age 0 to <2 Months |
|---|---|---|
| Feeding disorder of infancy or early childhood | | |
| Subjects Affected/Exposed | 0/10 (0.00%) | 1/16 (6.25%) |
| Occurrences (all) | 0 | 1 |
| Protein deficiency | | |
| Subjects Affected/Exposed | 0/10 (0.00%) | 1/16 (6.25%) |
| Occurrences (all) | 0 | 2 |
| Infections and infestations Gastroenteritis | | |
| Subjects Affected/Exposed | 1/10 (10.00%) | 1/16 (6.25%) |
| Occurrences (all) | 2 | 1 |
| Upper respiratory tract infection | | |
| Subjects Affected/Exposed | 4/10 (40.00%) | 5/16 (31.25%) |
| Occurrences (all) | 6 | 7 |
| Urinary tract infection | | |
| Subjects Affected/Exposed | 1/10 (10.00%) | 2/16 (12.50%) |
| Occurrences (all) | 1 | 2 |
| Viral infection | | |
| Subjects Affected/Exposed | 1/10 (10.00%) | 1/16 (6.25%) |
| Occurrences (all) | 1 | 1 |
| Nasopharyngitis | | |
| Subjects Affected/Exposed | 2/10 (20.00%) | 4/16 (25.00%) |
| Occurrences (all) | 2 | 7 |
| Croup infectious | | |
| Subjects Affected/Exposed | 1/10 (10.00%) | 1/16 (6.25%) |
| Occurrences (all) | 1 | 2 |
| Otitis media | | |
| Subjects Affected/Exposed | 2/10 (20.00%) | 1/16 (6.25%) |
| Occurrences (all) | 2 | 1 |
| Conjunctivitis | | |
| Subjects Affected/Exposed | 1/10 (10.00%) | 0/16 (0.00%) |
| Occurrences (all) | 1 | 0 |
| Pharyngitis | | |
| Subjects Affected/Exposed | 1/10 (10.00%) | 0/16 (0.00%) |
| Occurrences (all) | 1 | 0 |
| Pneumonia | | |
| Subjects Affected/Exposed | 1/10 (10.00%) | 0/16 (0.00%) |
| Occurrences (all) | 1 | 0 |
| Sinusitis | | |
| Subjects Affected/Exposed | 1/10 (10.00%) | 1/16 (6.25%) |
| Occurrences (all) | 2 | 1 |
| Ear infection | | |
| Subjects Affected/Exposed | 0/10 (0.00%) | 3/16 (18.75%) |
| Occurrences (all) | 0 | 3 |
| Oral candidiasis | | |
| Subjects Affected/Exposed | 0/10 (0.00%) | 2/16 (12.50%) |
| Occurrences (all) | 0 | 2 |
| Respiratory syncytial virus infection | | |
| Subjects Affected/Exposed | 0/10 (0.00%) | 1/16 (6.25%) |
| Occurrences (all) | 0 | 1 |
| Angular cheilitis | | |
| Subjects Affected/Exposed | 0/10 (0.00%) | 1/16 (6.25%) |
| Occurrences (all) | 0 | 2 |
| Candida infection | | |
| Subjects Affected/Exposed | 0/10 (0.00%) | 1/16 (6.25%) |
| Occurrences (all) | 0 | 2 |

TABLE 29-continued

Non-serious adverse events.

| Non-Serious Adverse Events | RAVICTI: Age 2 Months to <2 Years | RAVICTI: Age 0 to <2 Months |
|---|---|---|
| Gastrointestinal viral infection | | |
| Subjects Affected/Exposed | 0/10 (0.00%) | 1/16 (6.25%) |
| Occurrences (all) | 0 | 1 |
| Lower respiratory tract infection | | |
| Subjects Affected/Exposed | 0/10 (0.00%) | 1/16 (6.25%) |
| Occurrences (all) | 0 | 1 |
| Otitis media acute | | |
| Subjects Affected/Exposed | 0/10 (0.00%) | 1/16 (6.25%) |
| Occurrences (all) | 0 | 1 |
| Rhinovirus infection | | |
| Subjects Affected/Exposed | 0/10 (0.00%) | 1/16 (6.25%) |
| Occurrences (all) | 0 | 1 |

What is claimed is:

1. A method of treating a urea cycle disorder (UCD) in a patient under 2 years of age comprising
administering glycerol phenylbutyrate to said patient at an initial daily dose which is administered at an initial frequency of administration; and
if after said administration, said patient exhibits neurological symptoms, normal ammonia levels, and a ratio of plasma PAA to plasma PAGN of >2.5 or a level of plasma PAA of >500 μg/mL, then administering said glycerol phenylbutyrate to said patient at a reduced daily dose while maintaining said initial frequency of administration,
wherein the initial frequency of administration is 3 to 6 times daily, and
wherein if said patient is in a hyperammonemic crisis, then said initial daily dose is 11.2 mL/m$^2$/day, if said patient is not in a hyperammonemic crisis, then said initial daily dose is 8.5 mL/m$^2$/day, and if said patient previously had been administered NaPBA or NaBz, then said initial daily dose is equal to 0.81 times the total number of grams of NaPBA powder the patient was receiving, or 0.86 times the total number of grams of in NaPBA tablet form the patient was receiving, or 0.5 times the total number of grams of in NaBz the patient was receiving.

2. A method of treating a urea cycle disorder (UCD) in a patient under 2 years of age comprising
administering glycerol phenylbutyrate to said patient at an initial daily dose which is administered at an initial frequency of administration; and
if after said administration said patient exhibits neurological symptoms, normal ammonia levels, and a ratio of plasma PAA to plasma PAGN of >2.5 or a level of plasma PAA of >500 μg/mL, then administering said glycerol phenylbutyrate to said patient at a lower dose or increased frequency of administration while maintaining said daily dose,
wherein the initial frequency of administration is 3 to 6 times daily, and
wherein if said patient is in a hyperammonemic crisis, then said initial daily dose is 11.2 mL/m$^2$/day, if said patient is not in a hyperammonemic crisis, then said initial daily dose is 8.5 mL/m$^2$/day, and if said patient previously had been administered NaPBA or NaBz, then said initial daily dose is equal to 0.81 times the total number of grams of NaPBA powder the patient was receiving, or 0.86 times the total number of grams of in NaPBA tablet form the patient was receiving, or 0.5 times the total number of grams of in NaBz the patient was receiving.

3. A method of treating a urea cycle disorder (UCD) in a patient under 2 years of age comprising
administering glycerol phenylbutyrate to said patient at an initial daily dose which is administered at an initial frequency of administration; and
if after said administration said patient exhibits neurological symptoms, normal ammonia levels, and a ratio of plasma PAA to plasma PAGN of <2.5, then said glycerol phenylbutyrate to said patient should continue to be administered at the same dose and frequency and the patient evaluated for other causes of his or her neurological symptoms,
wherein the initial frequency of administration is 3 to 6 times daily, and
wherein if said patient is in a hyperammonemic crisis, then said initial daily dose is 11.2 mL/m$^2$/day, if said patient is not in a hyperammonemic crisis, then said initial daily dose is 8.5 mL/m$^2$/day, and if said patient previously had been administered NaPBA or NaBz, then said initial daily dose is equal to 0.81 times the total number of grams of NaPBA powder the patient was receiving, or 0.86 times the total number of grams of in NaPBA tablet form the patient was receiving, or 0.5 times the total number of grams of in NaBz the patient was receiving.

4. The method of claim 1, wherein said patient is less than about one month of age.

5. The method of claim 1, wherein said patient is from 1 month to two years of age.

6. The method of claim 1, wherein said neurological symptoms include headache, confusion, vomiting, lethargy, or any combination thereof.

7. The method of claim 2, wherein said patient is less than about one month of age.

8. The method of claim 2, wherein said patient is from 1 month to two years of age.

9. The method of claim 2, wherein said neurological symptoms include headache, confusion, vomiting, lethargy, or any combination thereof.

10. The method of claim 3, wherein said patient is less than about one month of age.

11. The method of claim 3, wherein said patient is from 1 month to two years of age.

12. The method of claim 3, wherein said neurological symptoms include headache, confusion, vomiting, lethargy, or any combination thereof.

* * * * *